US010864350B2

(12) United States Patent
Chou et al.

(10) Patent No.: US 10,864,350 B2
(45) Date of Patent: Dec. 15, 2020

(54) SINGLE OPERATOR INTRACRANIAL MEDICAL DEVICE DELIVERY SYSTEMS AND METHODS OF USE

(71) Applicant: Route 92 Medical, Inc., San Mateo, CA (US)

(72) Inventors: Tony M. Chou, San Mateo, CA (US); Scott D. Wilson, San Mateo, CA (US); Kirsten Valley, San Mateo, CA (US); Vera Shinsky, San Mateo, CA (US); Philip Evard, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 116 days.

(21) Appl. No.: 15/875,342

(22) Filed: Jan. 19, 2018

(65) Prior Publication Data

US 2018/0207399 A1 Jul. 26, 2018

Related U.S. Application Data

(63) Continuation of application No. 15/875,214, filed on Jan. 19, 2018.
(Continued)

(51) Int. Cl.
*A61M 25/00* (2006.01)
*A61M 25/01* (2006.01)
(Continued)

(52) U.S. Cl.
CPC ..... *A61M 25/0021* (2013.01); *A61B 17/1204* (2013.01); *A61B 17/12109* (2013.01);
(Continued)

(58) Field of Classification Search
CPC .................. A61M 25/0021; A61M 25/0052
See application file for complete search history.

(56) References Cited

U.S. PATENT DOCUMENTS 2,623,520 A 12/1952 Bamford, Jr. et al.
3,612,050 A 10/1971 Sheridan
(Continued)

FOREIGN PATENT DOCUMENTS

CN 103260689 A 8/2013
WO WO-94/02194 A1 2/1994
(Continued)

OTHER PUBLICATIONS

Delgado Almandoz, Josser E., et al. "Comparison of clinical outcomes in patients with acute ischemic strokes treated with mechanical thrombectomy using either Solumbra or ADAPT techniques." *Journal of Neurointerventional Surgery*, vol. 8, 2016, pp. 1123-1128.
(Continued)

*Primary Examiner* — Richard G Louis
(74) *Attorney, Agent, or Firm* — Mintz Levin Cohn Ferris Glovsky and Popeo, P.C.

(57) ABSTRACT

A rapid exchange microcatheter for accessing the intracranial neurovasculature. A side opening through the sidewall is located a first distance proximal to the distal-most tip. A proximal opening located proximal to the side opening is a second distance from the distal-most tip. A distal, reinforced catheter portion extends between a distal end region to a point near the side opening. A proximal, reinforced catheter portion extends a distance from a point near the side opening towards the proximal end of the catheter body. The side opening is positioned within a gap between a proximal end of the distal reinforced catheter portion and a distal end of the proximal reinforced catheter portion. A payload of a cerebral treatment device is housed within the lumen proximal to the side opening. Related devices, systems, and methods are disclosed.

16 Claims, 38 Drawing Sheets

Related U.S. Application Data

(60) Provisional application No. 62/517,005, filed on Jun. 8, 2017, provisional application No. 62/448,678, filed on Jan. 20, 2017.

(51) Int. Cl.
| | |
|---|---|
| *A61M 25/09* | (2006.01) |
| *A61B 17/12* | (2006.01) |
| *A61F 2/95* | (2013.01) |
| *A61F 2/966* | (2013.01) |
| *A61M 25/06* | (2006.01) |
| *A61F 2/06* | (2013.01) |

(52) U.S. Cl.
CPC .......... *A61B 17/12136* (2013.01); *A61F 2/95* (2013.01); *A61F 2/966* (2013.01); *A61M 25/005* (2013.01); *A61M 25/007* (2013.01); *A61M 25/0052* (2013.01); *A61M 25/0097* (2013.01); *A61M 25/01* (2013.01); *A61M 25/0108* (2013.01); *A61M 25/09* (2013.01); *A61F 2002/068* (2013.01); *A61F 2002/9528* (2013.01); *A61M 2025/0042* (2013.01); *A61M 2025/0059* (2013.01); *A61M 2025/0183* (2013.01); *A61M 2025/0681* (2013.01); *A61M 2205/0222* (2013.01); *A61M 2205/0238* (2013.01); *A61M 2205/586* (2013.01); *A61M 2210/0693* (2013.01); *A61M 2210/12* (2013.01)

(56) References Cited

U.S. PATENT DOCUMENTS

| | | | |
|---|---|---|---|
| 3,631,848 | A | 1/1972 | Muller |
| 4,013,080 | A | 3/1977 | Froning |
| 4,406,656 | A | 9/1983 | Hattler et al. |
| 4,946,443 | A | 8/1990 | Hauser et al. |
| 5,207,648 | A | 5/1993 | Gross |
| 5,338,300 | A | 8/1994 | Cox |
| 5,370,623 | A | 12/1994 | Kreamer |
| 5,385,562 | A | 1/1995 | Adams et al. |
| 5,484,407 | A | 1/1996 | Osypka |
| 5,591,194 | A | 1/1997 | Berthiaume |
| 5,658,309 | A | 8/1997 | Berthiaume et al. |
| 5,702,439 | A | 12/1997 | Keith et al. |
| 5,876,386 | A * | 3/1999 | Samson ............... A61L 29/041 600/435 |
| 5,911,725 | A | 6/1999 | Boury |
| 6,120,480 | A | 9/2000 | Zhang et al. |
| 6,165,167 | A | 12/2000 | Delaloye |
| 6,295,989 | B1 | 10/2001 | Connors, III |
| 6,475,195 | B1 | 11/2002 | Voda |
| 6,537,241 | B1 | 3/2003 | Odland |
| 6,676,637 | B1 | 1/2004 | Bonnette et al. |
| 6,689,144 | B2 | 2/2004 | Gerberding |
| 6,692,473 | B2 | 2/2004 | St. Cyr et al. |
| 6,740,104 | B1 | 5/2004 | Solar et al. |
| 6,755,803 | B1 | 6/2004 | Le et al. |
| 6,755,812 | B2 | 6/2004 | Peterson et al. |
| 6,926,658 | B2 | 8/2005 | Farnan |
| 7,033,325 | B1 | 4/2006 | Sullivan |
| 7,235,061 | B2 | 6/2007 | Tsugita |
| 7,316,678 | B2 | 1/2008 | Nash et al. |
| 7,374,560 | B2 | 5/2008 | Ressemann et al. |
| 7,604,612 | B2 | 10/2009 | Ressemann et al. |
| 7,691,121 | B2 | 4/2010 | Rosenbluth et al. |
| 7,717,934 | B2 | 5/2010 | Kusleika |
| 7,736,355 | B2 | 6/2010 | Itou et al. |
| 7,785,286 | B2 | 8/2010 | Magnin et al. |
| 7,850,654 | B2 | 12/2010 | Belhe et al. |
| 7,854,746 | B2 | 12/2010 | Dorn et al. |
| 7,967,789 | B2 | 6/2011 | Solar et al. |
| 7,972,294 | B2 | 7/2011 | Nash et al. |
| 8,048,032 | B2 | 11/2011 | Root et al. |
| 8,157,760 | B2 | 4/2012 | Criado et al. |
| 8,172,831 | B2 | 5/2012 | Webler, Jr. |
| 8,251,978 | B2 | 8/2012 | Nash et al. |
| 8,361,105 | B2 | 1/2013 | Adams et al. |
| 8,425,549 | B2 | 4/2013 | Lenker et al. |
| 8,523,801 | B2 | 9/2013 | Nash et al. |
| 8,535,272 | B2 | 9/2013 | Wang et al. |
| 8,540,759 | B2 | 9/2013 | Porter |
| 8,636,714 | B2 | 1/2014 | McFerran |
| 8,708,954 | B2 | 4/2014 | Webler |
| 8,758,325 | B2 | 6/2014 | Webster et al. |
| 8,801,749 | B2 | 8/2014 | Adams et al. |
| 8,876,776 | B2 | 11/2014 | Kassab et al. |
| RE45,380 | E | 2/2015 | Root et al. |
| 8,996,095 | B2 | 3/2015 | Anderson et al. |
| 9,144,662 | B2 | 9/2015 | Di Caprio et al. |
| RE45,760 | E | 10/2015 | Root et al. |
| RE45,776 | E | 10/2015 | Root et al. |
| 9,220,562 | B2 | 12/2015 | Brannan et al. |
| 9,233,230 | B2 | 1/2016 | Puhasmagi et al. |
| 9,352,123 | B2 | 5/2016 | Zhou et al. |
| 9,486,611 | B2 | 11/2016 | Petersen et al. |
| 9,820,761 | B2 | 11/2017 | Garrison et al. |
| 2002/0091407 | A1 | 7/2002 | Zadno-Azizi et al. |
| 2002/0138094 | A1 | 9/2002 | Borillo et al. |
| 2002/0165574 | A1 | 11/2002 | Ressemann et al. |
| 2002/0173785 | A1 | 11/2002 | Spear et al. |
| 2003/0050600 | A1 | 3/2003 | Ressemann et al. |
| 2003/0233038 | A1 | 12/2003 | Hassett |
| 2004/0019322 | A1 | 1/2004 | Hoffmann |
| 2004/0193177 | A1* | 9/2004 | Houghton ............... A61F 2/958 606/108 |
| 2004/0254602 | A1 | 12/2004 | Lehe et al. |
| 2005/0065498 | A1* | 3/2005 | McFerran ........... A61M 25/007 604/528 |
| 2005/0209674 | A1 | 9/2005 | Kutscher et al. |
| 2005/0209675 | A1* | 9/2005 | Ton ........................ A61F 2/95 623/1.11 |
| 2006/0079787 | A1 | 4/2006 | Whiting et al. |
| 2006/0258987 | A1 | 11/2006 | Lentz et al. |
| 2007/0185521 | A1 | 8/2007 | Bui et al. |
| 2007/0208302 | A1 | 9/2007 | Webster et al. |
| 2008/0033525 | A1 | 2/2008 | Shaked et al. |
| 2008/0119890 | A1 | 5/2008 | Adams et al. |
| 2008/0188888 | A1 | 8/2008 | Adams et al. |
| 2008/0195140 | A1 | 8/2008 | Myla et al. |
| 2009/0264865 | A1 | 10/2009 | Kawai |
| 2010/0004607 | A1 | 1/2010 | Wilson et al. |
| 2010/0030141 | A1 | 2/2010 | Chermoni |
| 2010/0114017 | A1 | 5/2010 | Lenker et al. |
| 2010/0204684 | A1 | 8/2010 | Garrison et al. |
| 2011/0034986 | A1 | 2/2011 | Chou et al. |
| 2011/0264133 | A1 | 10/2011 | Hanlon et al. |
| 2012/0095485 | A1 | 4/2012 | Cully et al. |
| 2012/0101561 | A1 | 4/2012 | Porter |
| 2012/0116350 | A1 | 5/2012 | Strauss et al. |
| 2013/0035628 | A1 | 2/2013 | Garrison et al. |
| 2013/0116701 | A1 | 5/2013 | Wang et al. |
| 2013/0281788 | A1 | 10/2013 | Garrison |
| 2014/0018773 | A1 | 1/2014 | Wang et al. |
| 2014/0039461 | A1 | 2/2014 | Anderson et al. |
| 2014/0088510 | A1 | 3/2014 | Nimkar et al. |
| 2014/0371709 | A1 | 12/2014 | Allen et al. |
| 2015/0080939 | A1 | 3/2015 | Adams et al. |
| 2015/0173782 | A1 | 6/2015 | Garrison et al. |
| 2015/0174368 | A1 | 6/2015 | Garrison et al. |
| 2016/0121081 | A1 | 5/2016 | Iwano et al. |
| 2016/0220741 | A1 | 8/2016 | Garrison et al. |
| 2016/0346502 | A1 | 12/2016 | Fuller et al. |
| 2016/0346508 | A1 | 12/2016 | Williams et al. |
| 2016/0346509 | A1 | 12/2016 | Anderson et al. |
| 2016/0367272 | A1 | 12/2016 | Garrison et al. |
| 2017/0020540 | A1 | 1/2017 | Chou et al. |
| 2017/0238950 | A1 | 8/2017 | Yang et al. |
| 2017/0252043 | A1 | 9/2017 | Fuller et al. |
| 2017/0274180 | A1 | 9/2017 | Garrison et al. |
| 2017/0281204 | A1 | 10/2017 | Garrison et al. |
| 2017/0368309 | A1 | 12/2017 | Garrison et al. |

(56) References Cited

U.S. PATENT DOCUMENTS

| | | | |
|---|---|---|---|
| 2018/0028205 | A1 | 2/2018 | Chou et al. |
| 2018/0064453 | A1 | 3/2018 | Garrison et al. |
| 2018/0116684 | A1 | 5/2018 | Garrison et al. |
| 2018/0133436 | A1 | 5/2018 | Garrison et al. |
| 2018/0193042 | A1 | 7/2018 | Wilson et al. |
| 2018/0207399 | A1 | 7/2018 | Chou et al. |
| 2018/0242978 | A1 | 8/2018 | Chou et al. |
| 2019/0008534 | A1 | 1/2019 | Garrison et al. |
| 2019/0046218 | A1 | 2/2019 | Garrison et al. |
| 2019/0366042 | A1 | 12/2019 | Garrison et al. |
| 2019/0366043 | A1 | 12/2019 | Garrison et al. |
| 2020/0016369 | A1 | 1/2020 | Garrison et al. |

FOREIGN PATENT DOCUMENTS

| | | | |
|---|---|---|---|
| WO | WO-2006/111944 | A1 | 10/2006 |
| WO | WO-2006/127929 | A2 | 11/2006 |
| WO | WO-2008/006111 | A2 | 1/2008 |
| WO | WO-2008006111 | A2 | 1/2008 |

OTHER PUBLICATIONS

Friedrich, Benjamin, et al. "Distance to Thrombus in Acute Middle Cerebral Artery Occlusion." *Stroke*, vol. 46, No. 3, 2015, pp. 692-696.

Jankowitz, Brian, et al. "Manual Aspiration Thrombectomy Adjunctive Endovascular Recanalization Technique in Acute Stroke Interventions." *Stroke*, vol. 43, No. 5, 2012, pp. 1408-1411.

Mokin, Maxim, et al. "Primary stentriever versus combined stentriever plus aspiration thrombectomy approaches: in vitro stroke model comparison." *Journal of NeuroInterventional Surgery*, vol. 7, 2015, pp. 453-457.

Request for Ex Parte Reexamination Transmittal Form and Request for Ex Parte Reexamination pursuant to 37 CFR 1.150 of U.S. Pat. No. 9,820,761 issued Nov. 21, 2017. Request filed May 11, 2018 and assigned U.S. Appl. No. 90/014,136. 35 pages.

"2012 Buyer's Guide: Microcatheters." Endovascular Today, 2012, pp. 48-51.

"2017 Buyer's Guide: Microcatheters." Endovascular Today, http://evtoday.com/buyers-guide/chart.asp?id=25. Accessed on Oct. 10, 2017. 11 pages.

"Trevo ProVue Retriever." Stryker Trevo® ProVue™ Retrieval System (by Concentric Medical®). (2016) Web. Apr. 13, 2018. 2 pages.

Farooq, Vasim et al. "Forward and Back Aspiration during ST-Elevation Myocardial Infarction: a Feasibility Study." EuroIntervention, vol. 11, No. 14, 2016, pp. 1639-1648.

Farooq, Vasim et al. "The Use of a Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.

Pena, Carlos. "Letter to Sequent Medical Inc Re: K150894, Trade/Device Name: VIA™ 21 Microcatheter." Department of Health & Human Services, Aug. 28, 2015, 14 pages.

Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-E259. 6 pages. (http://www.invasivecardiology.com/issue/4284).

Zuckerman, Bram. "Letter to Cathera Inc: Re K151638, Trade/Device Name: Phenom™ Catheters." Department of Health & Human Services, Nov. 13, 2015, 6 pages.

U.S. Appl. No. 13/921,165, filed Jun. 18, 2013, US 2013-0281788.
U.S. Appl. No. 15/699,401, filed Sep. 8, 2017, US 2017-0368309.
U.S. Appl. No. 15/727,373, filed Oct. 6, 2017, US 2018-0028205.
U.S. Appl. No. 15/747,089, filed Jan. 23, 2018, US 2018-0242978.
U.S. Appl. No. 15/866,012, filed Jan. 9, 2018, US 2018-0193042.
U.S. Appl. No. 15/875,214, filed Jan. 19, 2018, US 2018-0361114.
U.S. Appl. No. 15/875,342, filed Jan. 19, 2018, US 2018-0207399.
U.S. Appl. No. 16/117,741, filed Aug. 30, 2018, US 2019-0008534.
U.S. Appl. No. 16/117,753, filed Aug. 30, 2018, US 2019-0046218.
U.S. Appl. No. 16/414,532, filed May 16, 2019, US 2019-0351182.
U.S. Appl. No. 16/530,845, filed Aug. 2, 2019, US 2020-0023160.
U.S. Appl. No. 16/530,845, filed Aug. 16, 2019, US 2019-0366042.
U.S. Appl. No. 16/543,215, filed Aug. 16, 2019, US 2019-0366043.
U.S. Appl. No. 16/584,220, filed Sep. 26, 2019, US 2020-0016369.
U.S. Appl. No. 16/584,351, filed Sep. 26, 2019, US 2020-0038628.
U.S. Appl. No. 16/596,531, filed Oct. 8, 2019, US 2020-0046939.
U.S. Appl. No. 16/596,535, filed Oct. 8, 2019, US 2020-0046940.
U.S. Appl. No. 16/775,105, filed Jan. 28, 2020, US 2020-0164178.
PCT/US2019/032694, filed May 16, 2019, WO 2019/222518.

* cited by examiner

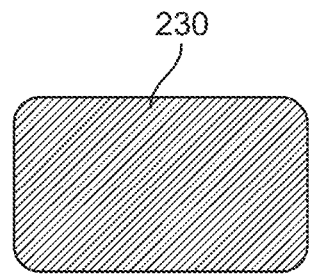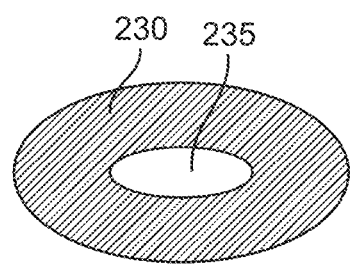
FIG. 4A  FIG. 4B
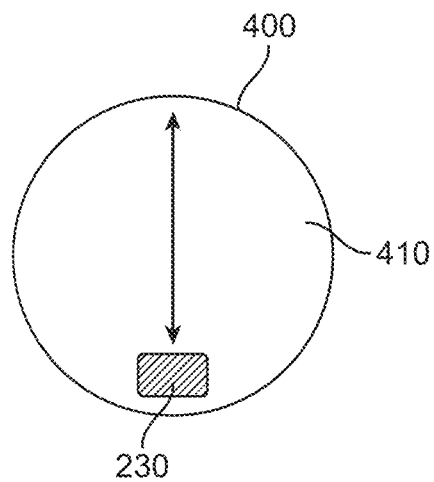
FIG. 4C
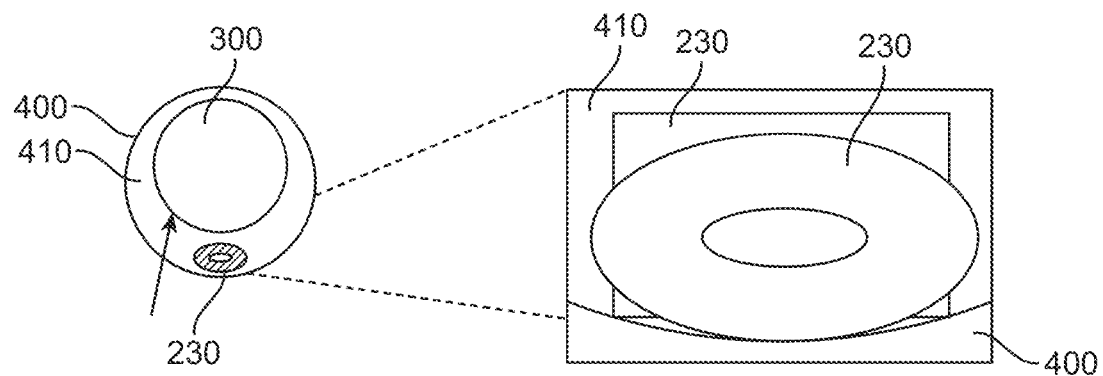
FIG. 4D  FIG. 4E

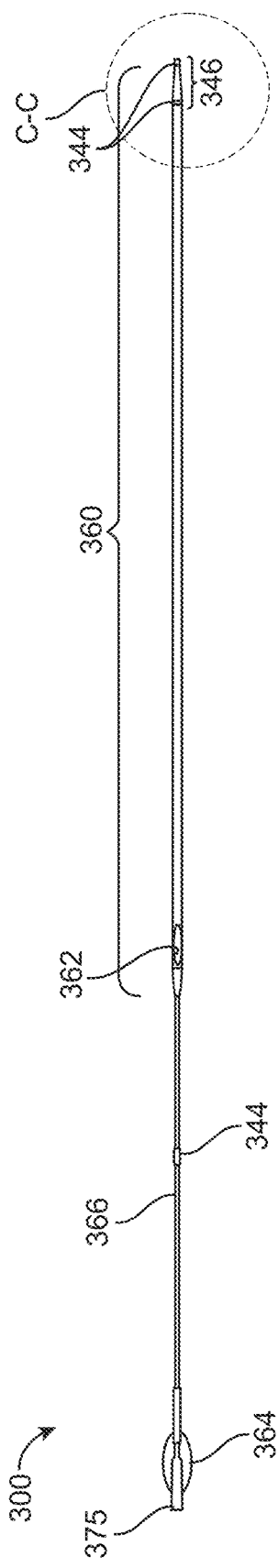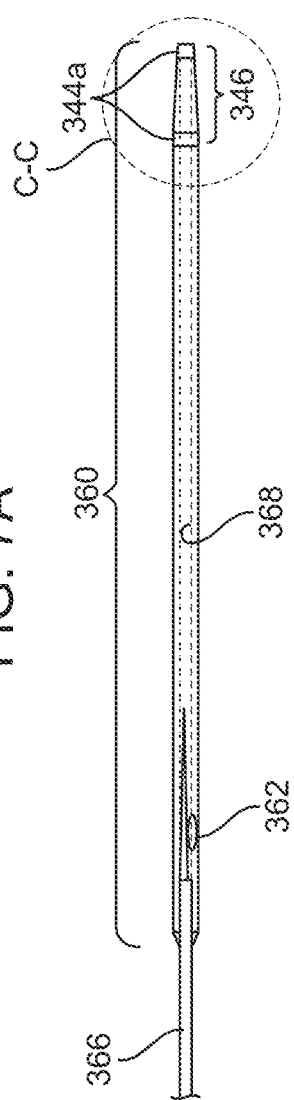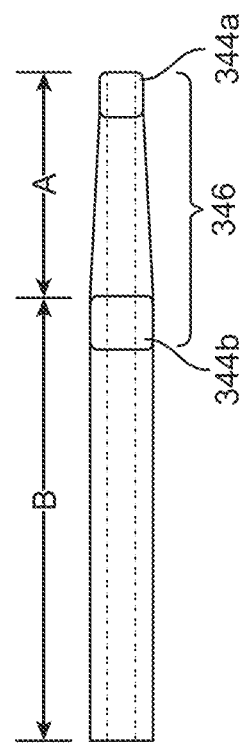
FIG. 7A
FIG. 7B
FIG. 7C

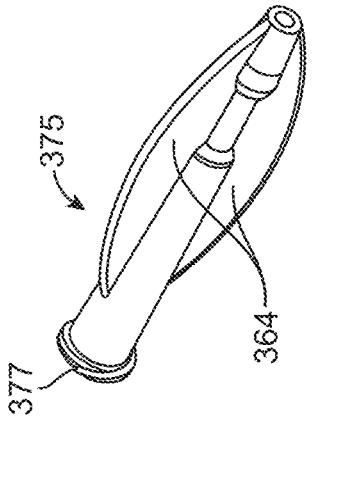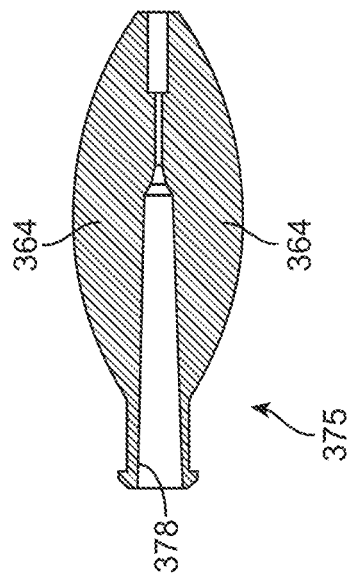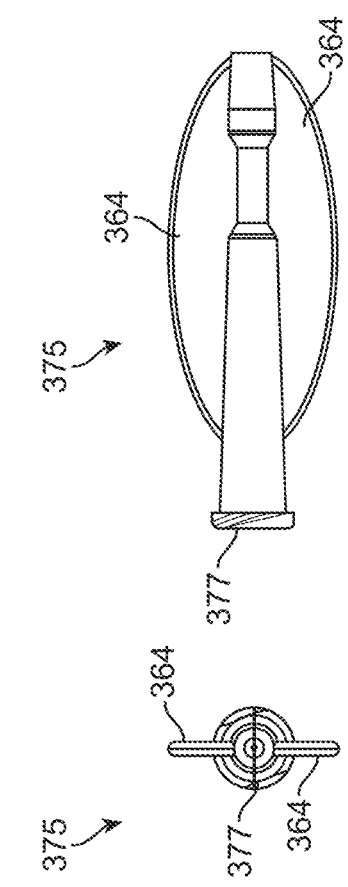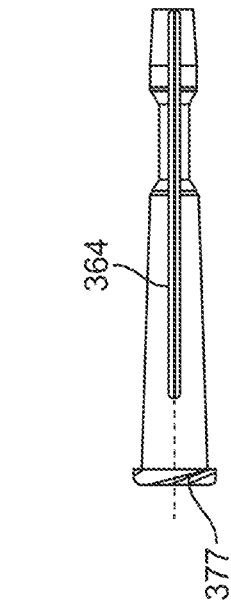

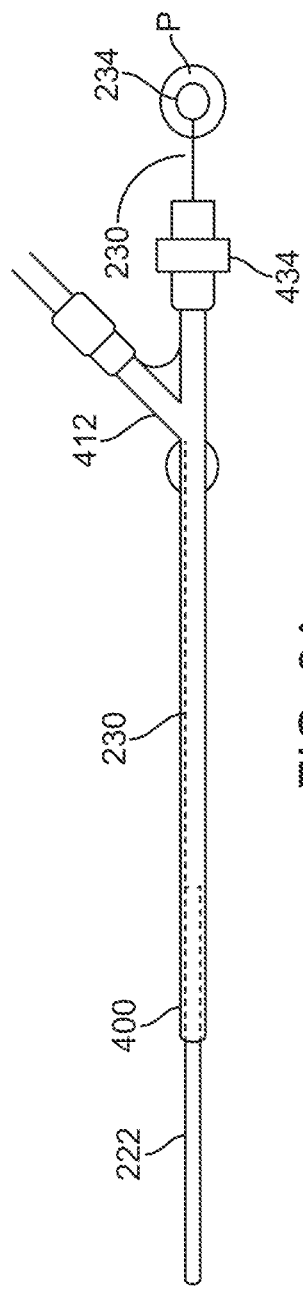
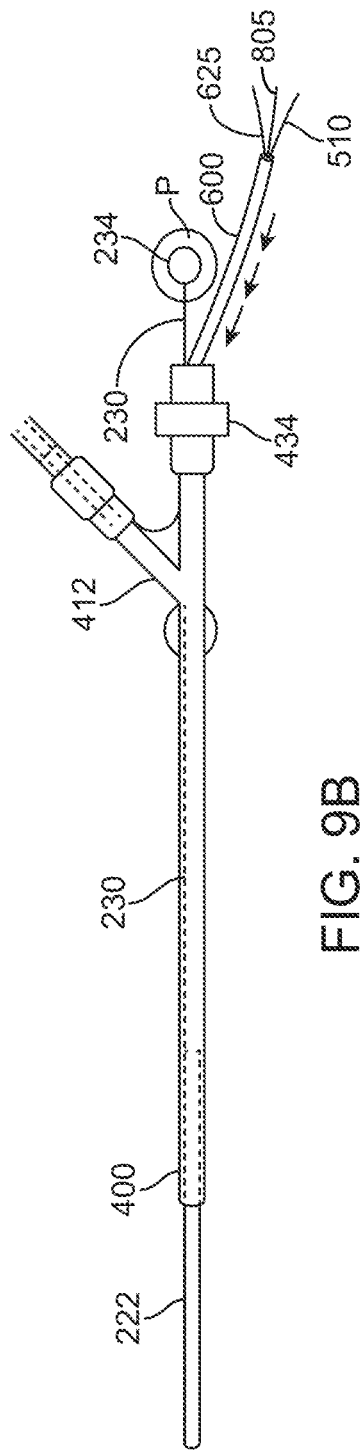

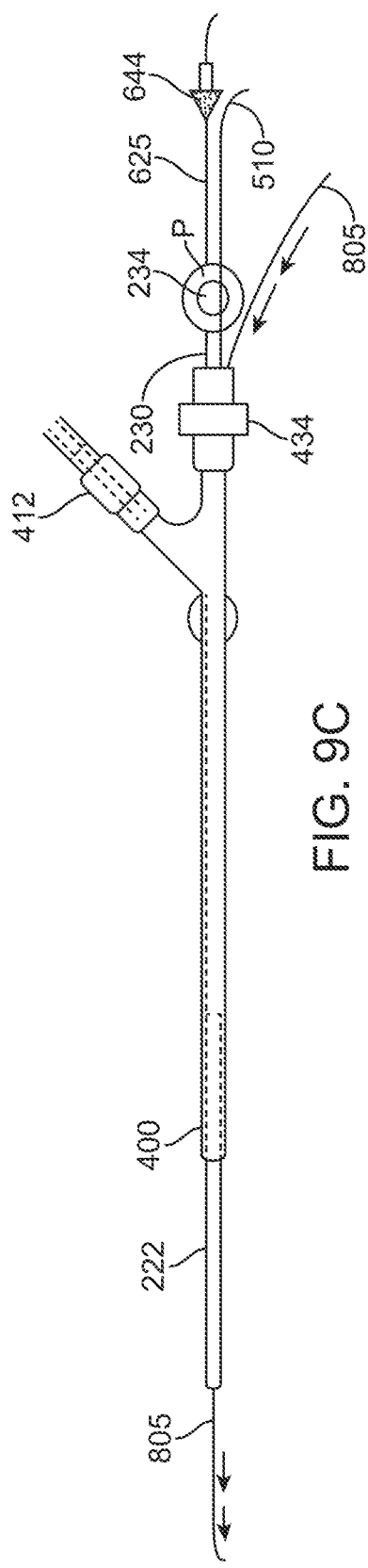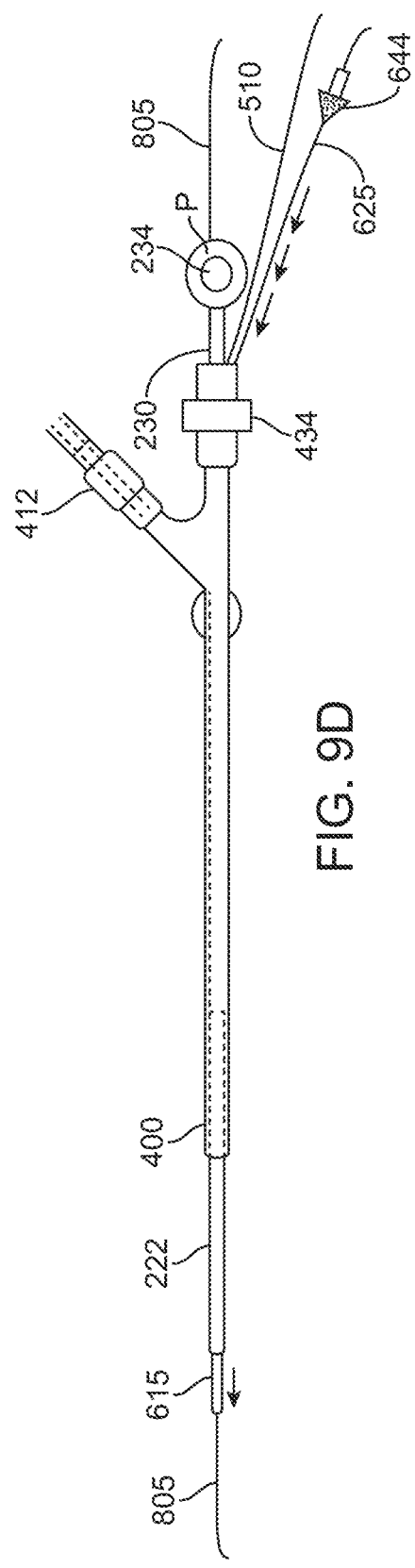

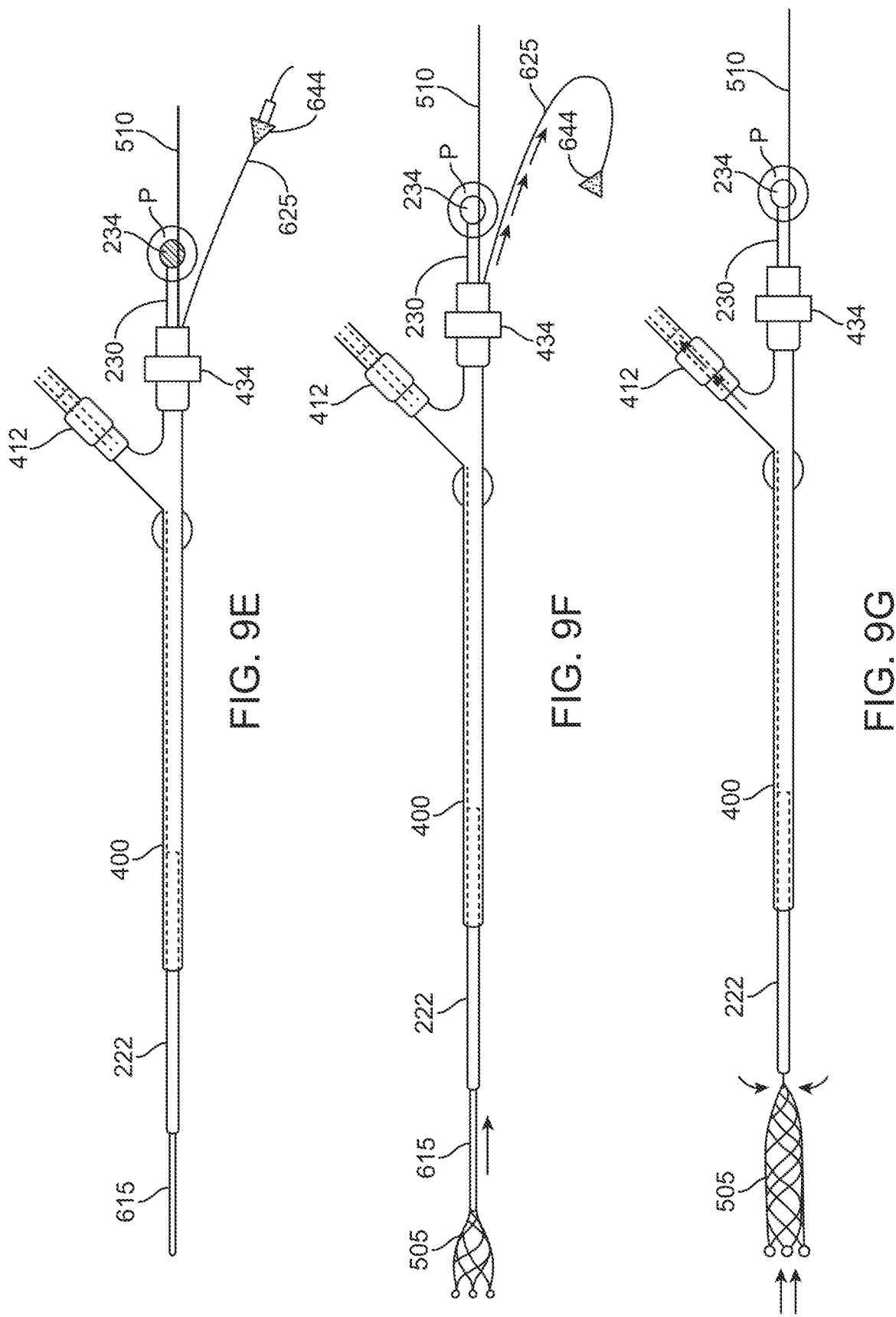

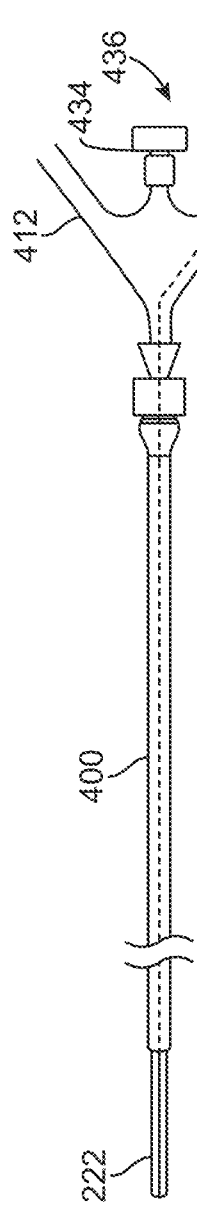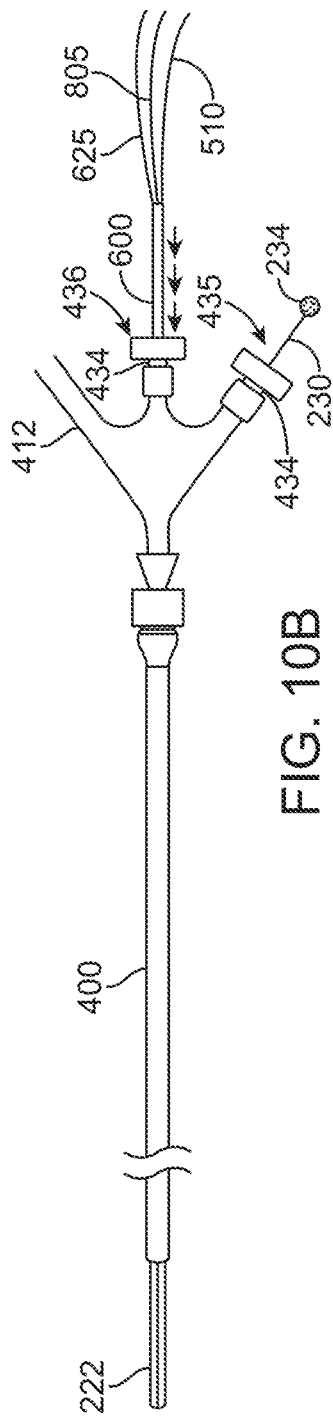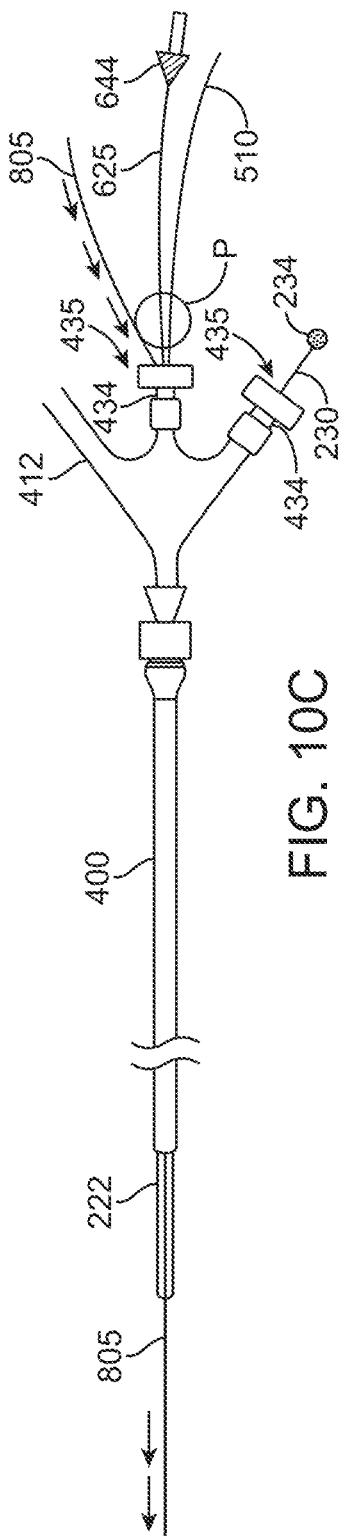

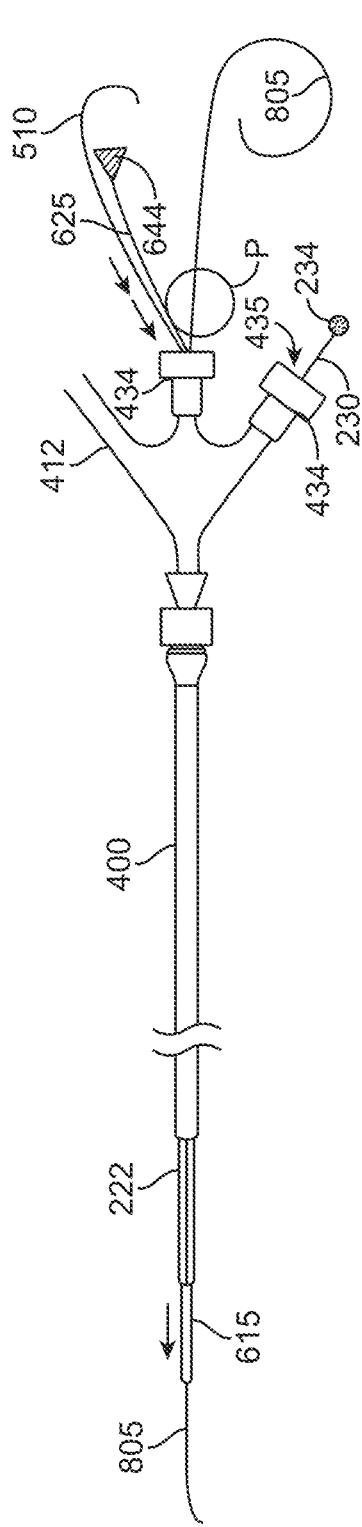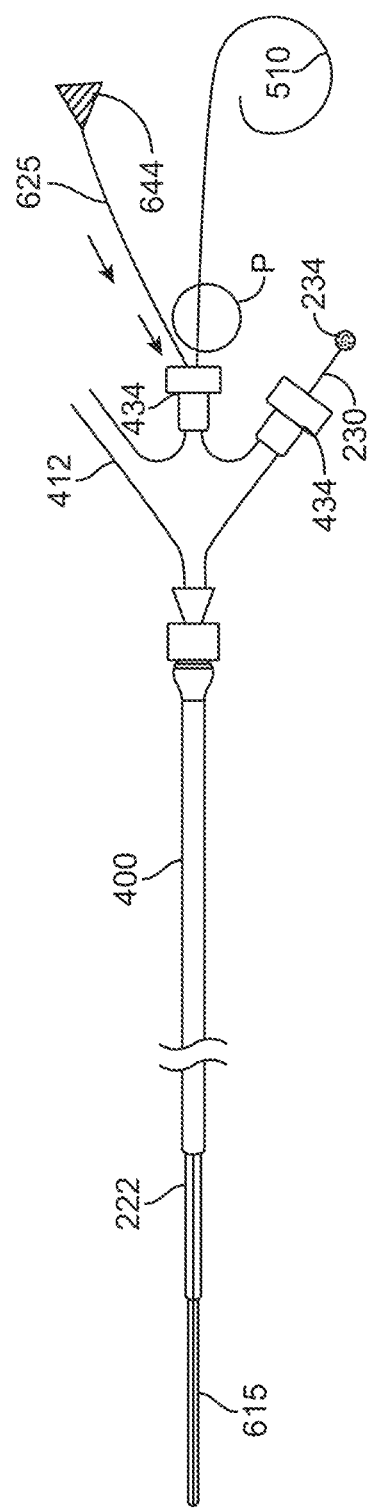
FIG. 10E
FIG. 10F

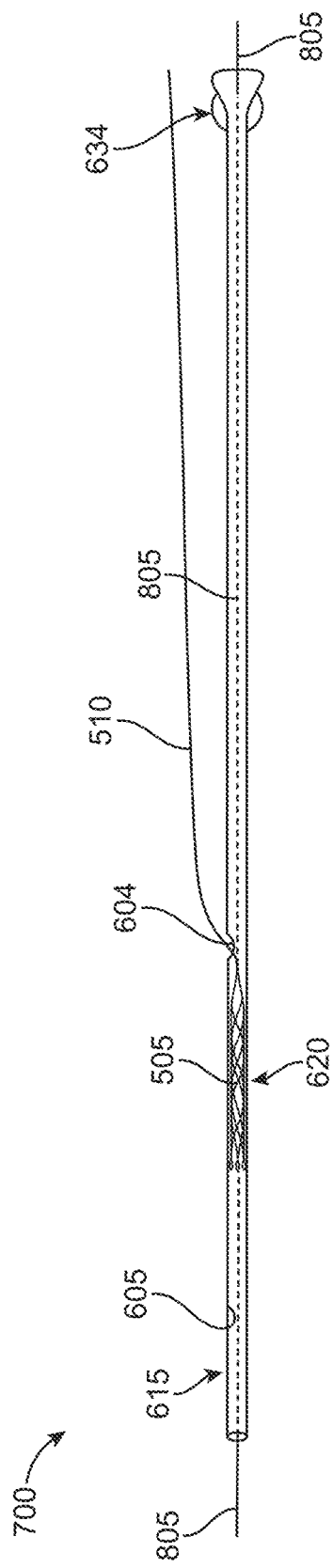
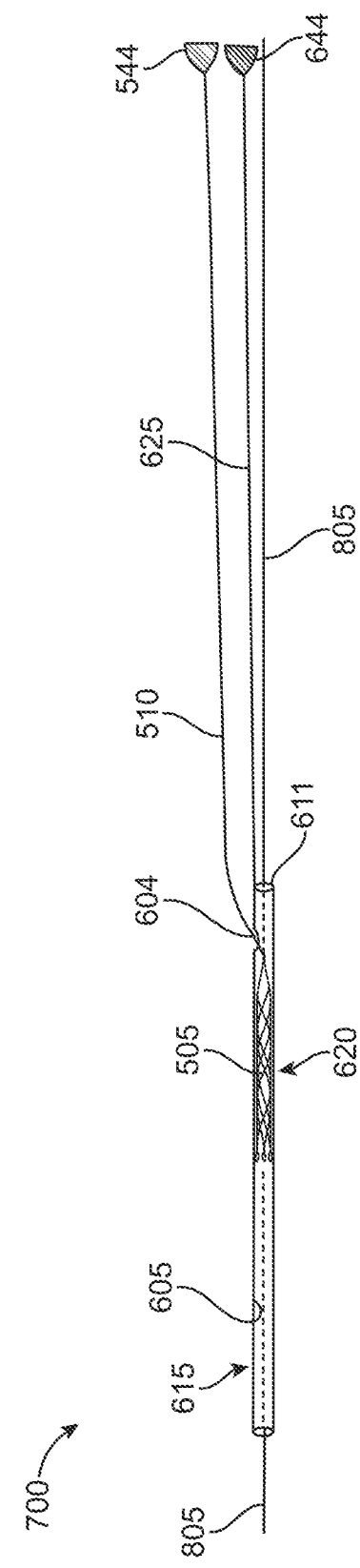

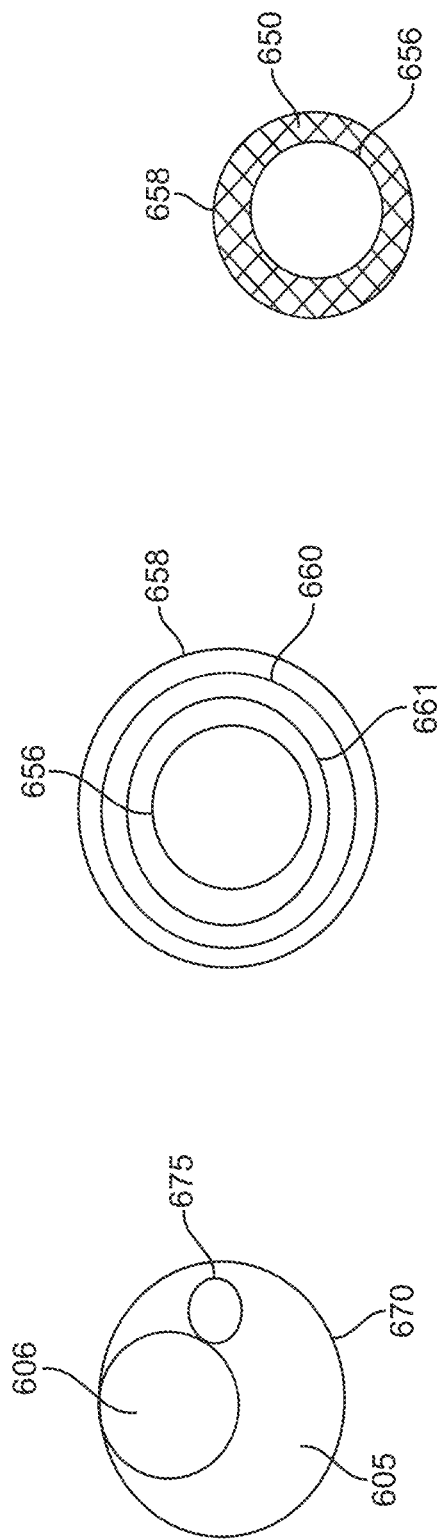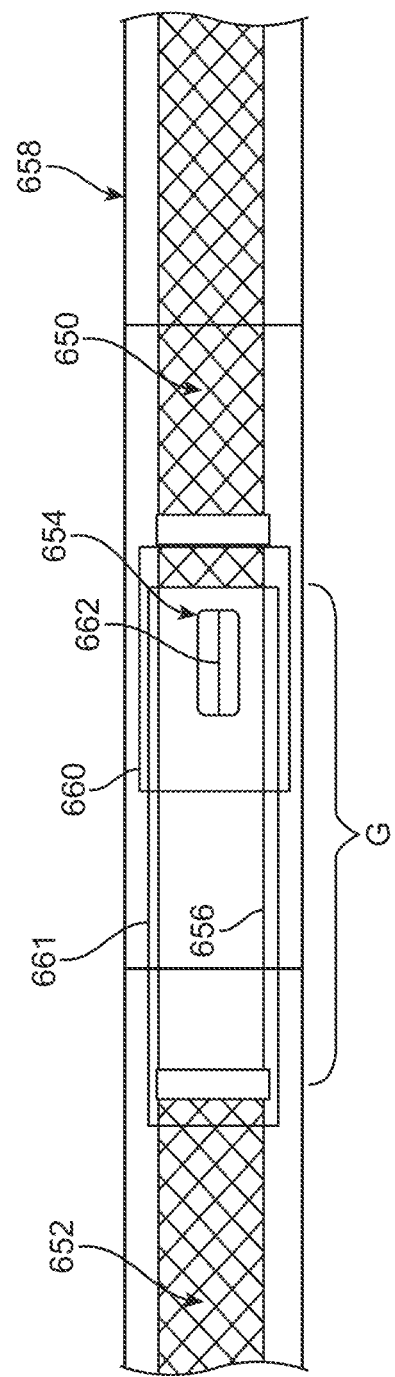

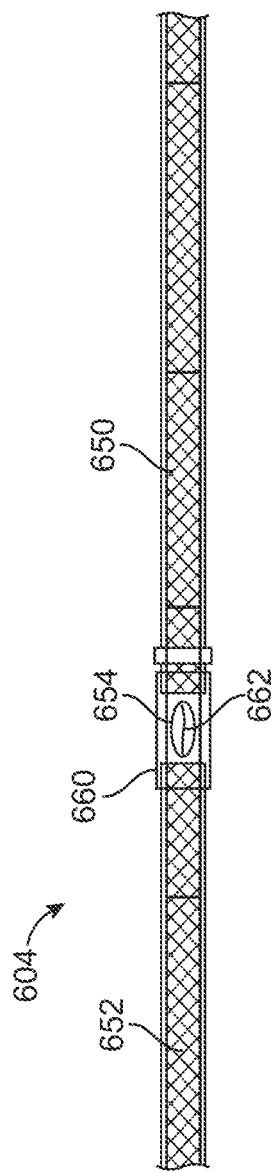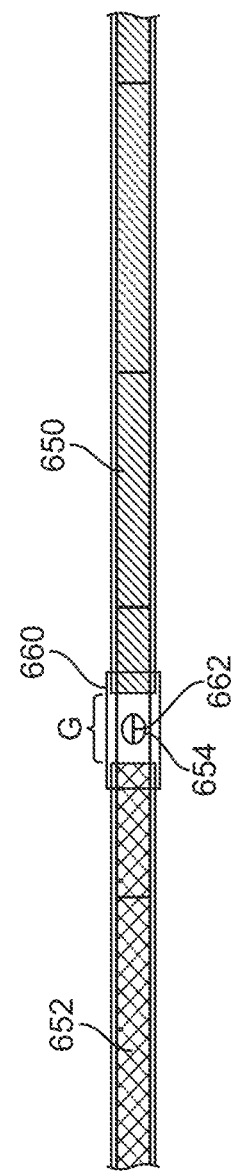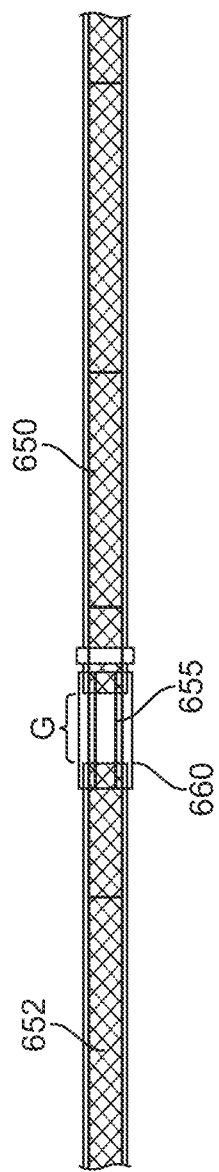

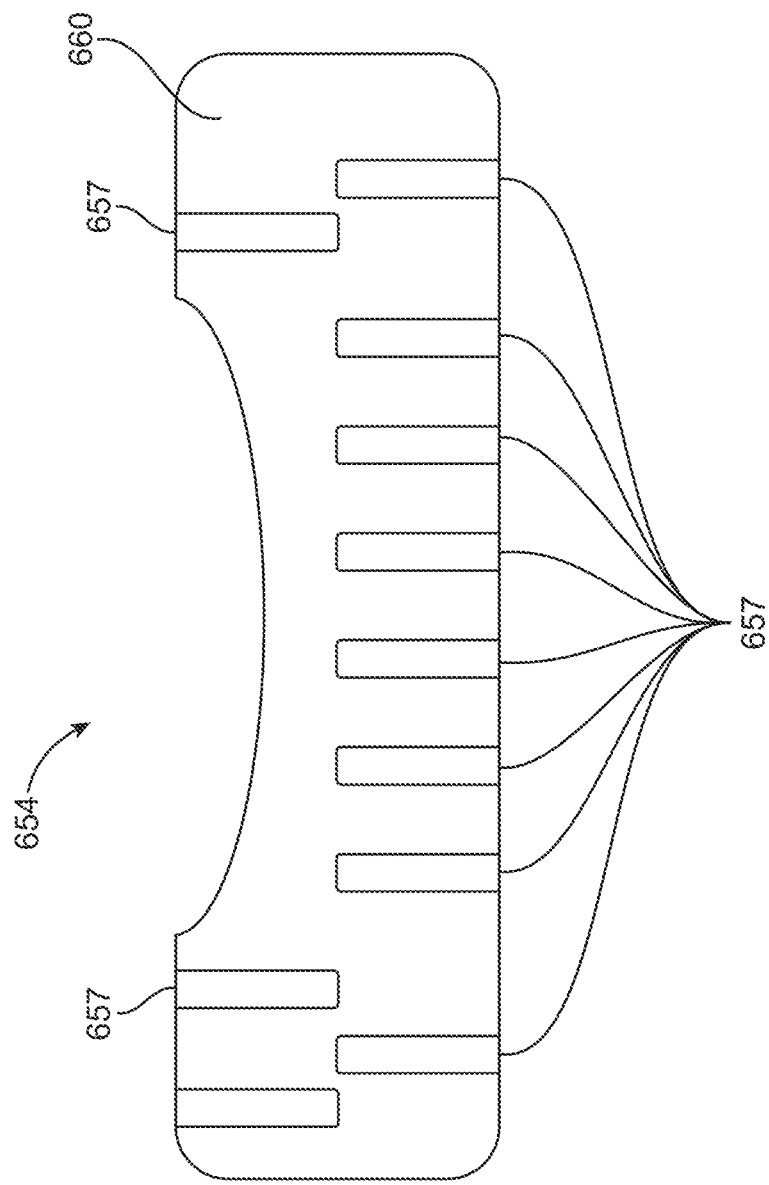

SINGLE OPERATOR INTRACRANIAL MEDICAL DEVICE DELIVERY SYSTEMS AND METHODS OF USE

CROSS-REFERENCE TO RELATED APPLICATIONS

This application is a continuation of co-pending U.S. patent application Ser. No. 15/875,214, filed Jan. 19, 2018, which claims the benefit of priority under 35 U.S.C. § 119(e) to U.S. Provisional Patent Application Ser. Nos. 62/448,678, filed Jan. 20, 2017, and 62/517,005, filed Jun. 8, 2017. The disclosures of the applications are hereby incorporated by reference in their entireties.

FIELD

The present technology relates generally to medical devices and methods, and more particularly, to single operator intracranial medical device delivery systems and their methods of use.

BACKGROUND

Acute ischemic stroke (AIS) usually occurs when an artery to the brain is occluded, preventing delivery of fresh oxygenated blood from the heart and lungs to the brain. These occlusions are typically caused by a thrombus or an embolus lodging in the artery and blocking the artery that feeds a territory of brain tissue. If an artery is blocked, ischemia then injury follows, and brain cells may stop working. Furthermore, if the artery remains blocked for more than a few minutes, the brain cells may die, leading to permanent neurological deficit or death. Therefore, immediate treatment is critical.

Two principal therapies are employed for treating ischemic stroke: thrombolytic therapy and endovascular treatment. The most common treatment used to reestablish flow or re-perfuse the stroke territory is the use of intravenous (IV) thrombolytic therapy. The timeframe to enact thrombolytic therapy is within 3 hours of symptom onset for IV infusion (4.5 hours in selected patients) or within 6 hours for site-directed intra-arterial infusion. Instituting therapy at later times has no proven benefit and may expose the patient to greater risk of bleeding due to the thrombolytic effect. Endovascular treatment most commonly uses a set of tools to mechanically remove the embolus, with our without the use of thrombolytic therapy.

The gamut of endovascular treatments include mechanical embolectomy, which utilizes a retrievable structure, e.g., a coil-tipped retrievable stent (also known as a stent retriever or a Stentriever®), a woven wire stent, or a laser cut stent with struts that can be opened within a clot in the cerebral anatomy to engage the clot with the stent struts, create a channel in the emboli to restore a certain amount of blood flow, and to subsequently retrieve the retrievable structure by pulling it out of the anatomy, along with aspiration techniques. Other endovascular techniques to mechanically remove AIS-associated embolus include Manual Aspiration Thrombectomy (MAT) (also known as the "ADAPT" technique). MAT is an endovascular procedure where large bore catheters are inserted through the transfemoral artery and maneuvered through complex anatomy to the level of the embolus, which may be in the extracranial carotids, vertebral arteries, or intracranial arteries. Aspiration techniques may be used to remove the embolus through the large bore catheters. Another endovascular procedure is Stentriever-Mediated Manual Aspiration Thrombectomy (SMAT) (similar to the Stentriever-assisted "Solumbra" technique). SMAT, like MAT, involves accessing the embolus through the transfemoral artery. After access is achieved, however, a retrievable structure is utilized to pull the embolus back into a large bore catheter.

To access the cerebral anatomy, guide catheters or guide sheaths are used to guide interventional devices to the target anatomy from an arterial access site, typically the femoral artery. The length of the guide is determined by the distance between the access site and the desired location of the guide distal tip. Interventional devices such as guidewires, microcatheters, and intermediate catheters used for sub-selective guides and aspiration, are inserted through the guide and advanced to the target site. Often, devices are used in a co-axial fashion, namely, a guidewire inside a microcatheter inside an intermediate catheter is advanced as an assembly to the target site in a stepwise fashion with the inner, most atraumatic elements, advancing distally first and providing support for advancement of the outer elements. The length of each element of the coaxial assemblage takes into account the length of the guide, the length of proximal connectors on the catheters, and the length needed to extend from the distal end.

Typical tri-axial systems such as for aspiration or delivery of stent retrievers and other interventional devices require overlapped series of catheters, each with their own rotating hemostatic valves (RHV). For example, a guidewire can be inserted through a Penumbra Velocity microcatheter having a first proximal RHV, which can be inserted through a Penumbra ACE68 having a second proximal RHV, which can be inserted through a Penumbra NeuronMAX 088 access catheter having a third proximal RHV positioned in the high carotid via a femoral introducer. Maintaining the coaxial relationships between these catheters can be technically challenging. The three RHVs must be constantly adjusted with two hands or, more commonly, four hands. Further, the working area of typical tri-axial systems for aspiration and/or intracranial device delivery can require working area of 3-5 feet at the base of the operating table.

The time required to access the site of the occlusion and restore even partially flow to the vessel is crucial in determining a successful outcome of such procedures. Similarly, the occurrence of distal emboli during the procedure and the potentially negative neurologic effect and procedural complications such as perforation and intracerebral hemorrhage are limits to success of the procedure. There is a need for a system of devices and methods that allow for rapid access, optimized catheter aspiration and treatment to fully restore flow to the blocked cerebral vessel.

SUMMARY

According to a first aspect, disclosed is a rapid exchange microcatheter for accessing the intracranial neurovasculature. The microcatheter includes a catheter body having a sidewall extending between a proximal end to a distal-most tip, the sidewall defining an internal lumen having an inner diameter sized to house a payload of a cerebral treatment device. The microcatheter includes a distal opening from the internal lumen near the distal-most tip, a side opening through the sidewall of the catheter body and a proximal opening located proximal to the side opening. The side opening is located a first distance proximal to the distal-most tip of the catheter body. The proximal opening is located a second distance from the distal-most tip of the catheter body. The microcatheter includes a distal, reinforced catheter portion extending between a distal end region of the catheter body to a point near the side opening; and a proximal, reinforced catheter portion extending a distance from a point near the side opening towards the proximal end of the catheter body. The side opening is positioned within a gap between a proximal end of the distal reinforced catheter portion and a distal end of the proximal, reinforced catheter portion. The payload of the cerebral treatment device is housed within the lumen proximal to the side opening.

The first distance can be between about 10 cm to about 20 cm. The second distance can be greater than about 20 cm. The distal opening can be located at the distal-most tip of the catheter. The side opening can be sized to pass a guidewire having an outer diameter that is equal to or less than about 0.018". The proximal, reinforced catheter portion can be less flexible than the distal, reinforced catheter portion. The distal, reinforced catheter portion can have a first reinforcement structure. The proximal, reinforced catheter portion can have a second reinforcement structure. The first reinforcement structure can be coupled to the second reinforcement structure by a rigid coupler. The rigid coupler can form a reinforcement structure that is different from the first reinforcement structure or the second reinforcement structure. The first and second reinforcement structures can be similar in structure to one another or different structure. The first reinforcement structure can be less rigid than the second reinforcement structure and the second reinforcement structure can be less rigid than the rigid coupler. The first reinforcement structure can be a coil and the second reinforcement structure can be a coil, wherein a pitch of the coil of the first reinforcement structure is greater than a pitch of the coil of the second reinforcement structure. The first reinforcement structure can be a coil and the second reinforcement structure can be a braid.

The coupler can have a window aligned with the side opening. The side opening can be configured to allow a guidewire to pass into or out of the internal lumen while preventing the payload from engaging or snagging on the side opening as it is moved through the internal lumen during deployment. The sidewall of the microcatheter can further include a lubricious, tubular liner and a reinforcement layer positioned over the tubular liner that is more rigid than the tubular liner. The reinforcement layer can include a first reinforcement structure extending within the distal, reinforced catheter portion. The second reinforcement structure extending within the proximal, reinforced catheter portion can have a distal end, the proximal end of the first reinforcement structure separated from the distal end of the second reinforcement structure creating the gap. A short, tubular rigid coupler can be positioned over the proximal end of the first reinforcement structure and over the distal end of the second reinforcement structure. The coupler can have an elongate window extending through a sidewall of the coupler. An outer jacket can be positioned over the coupler and the reinforcement layer. The coupler can be sized to span the gap such that the elongate window of the coupler is aligned with the gap while at least a first portion of the coupler is positioned over the proximal end the first reinforcement structure and at least a second portion of the coupler is positioned over the distal end of the second reinforcement structure. The tubular liner and the outer jacket can seal together at the elongate window forming a dual-laminate membrane encapsulating the side opening of the microcatheter. A slit can extend through the membrane allowing for the guidewire to pass through the side opening.

The inner diameter of the microcatheter can be less than about 0.035" to about 0.0165". An outer diameter of the catheter body can be less than about 0.050" to about 0.023".

In an interrelated aspect, disclosed is a system including the rapid exchange microcatheter and a distal access catheter having a flexible distal luminal portion having a proximal end, a proximal end region, a proximal opening, a distal end, and a lumen extending between the proximal end and the distal end. The lumen of the distal access catheter is sized to receive the catheter body of the rapid exchange microcatheter.

The distal access catheter can further include a proximal extension that is less flexible than the flexible distal luminal portion and is configured to control movement of the distal access catheter. The proximal extension can extend proximally from a point of attachment with the flexible distal luminal portion adjacent the proximal opening. The flexible distal luminal portion can have an outer diameter at the point of attachment that is larger than an outer diameter of the proximal extension at the point of attachment. The proximal extension of the distal access catheter can be solid or hollow.

The distal access catheter can be assembled with a tapered inner member forming an assembled coaxial catheter system. The tapered inner member can include a flexible elongate body having a proximal end region, an outer diameter, a tapered distal tip portion, a distal opening, and a single lumen extending longitudinally through the flexible elongate body to the distal opening. The tapered inner member can include a proximal portion extending proximally from the proximal end region to a proximal-most end of the tapered inner member. When assembled, the tapered inner member can extend through the lumen of the distal access catheter and the tapered distal tip portion extends distal to the distal end of the distal access catheter. The flexible elongate body of the tapered inner member can include a proximal opening sized to accommodate a guidewire. The proximal opening can be located through a sidewall of the proximal end region of the flexible elongate body. The proximal portion can be a hypotube having an opening in fluid communication with the single lumen of the flexible elongate body.

The system can further include a guide sheath having a working lumen extending between a proximal end region and a distal end region, the distal end region of the guide sheath having at least one opening in communication with the working lumen of the guide sheath. The guide sheath can have a working length sufficient to have the distal end region of the guide sheath positioned within a portion of a carotid artery and the proximal end region positioned near a femoral access site. The flexible distal luminal portion of the distal access catheter can be sized to extend coaxially through the working lumen of the guide sheath and pass through the at least one opening of the guide sheath telescopically extending the distal end of the flexible distal luminal portion beyond the distal end region of the guide sheath. The catheter body of the rapid exchange microcatheter can be sized to extend coaxially through the lumen of the distal access catheter extending coaxially through the working lumen of the guide sheath such that the distal-most tip of the microcatheter passes through an opening at the distal end of the distal access catheter. The distal end region of the guide sheath can further include an occlusion balloon on an outer surface configured to arrest flow through a vessel upon expansion of the sealing element. The cerebral treatment device can be a stent, stent retriever or a flow diverter.

In an interrelated aspect, disclosed is a method of accessing the intracranial neurovasculature using a catheter system. The method includes positioning within a vessel of a patient a guide sheath having a working lumen in communication with a port at a proximal end. A distal end of the guide sheath is advanced at least to an internal carotid artery. The method includes inserting a distal access catheter through the port into the working lumen of the guide sheath, the distal access catheter having a lumen and a distal end. The method includes positioning the distal end of the distal access catheter beyond the distal end of the guide sheath. The method includes inserting a microcatheter loaded with a payload of a cerebral treatment device through the lumen of the distal access catheter. The microcatheter includes a lumen, a distal end region having a distal opening from the lumen, and a side opening from the lumen located a distance proximal to the distal opening. The payload, when loaded, is housed within the lumen proximal to the side opening. The method includes advancing the microcatheter loaded with the payload through the lumen of the distal access catheter until the distal end region of the microcatheter is advanced at least to the distal end of the distal access catheter. The method includes deploying the payload of the cerebral treatment device within the intracranial neurovasculature.

The distal access catheter can include a flexible distal luminal portion having a proximal end, a proximal end region, a proximal opening, the lumen extending between the proximal end and the distal end; and a proximal extension extending proximally from a point of attachment adjacent the proximal opening. The proximal extension can be less flexible than the flexible distal luminal portion and is configured to control movement of the distal access catheter. The flexible distal luminal portion can have an outer diameter at the point of attachment that is larger than an outer diameter of the proximal extension at the point of attachment.

The distal access catheter can be assembled with a tapered inner member forming an assembled coaxial catheter system. The tapered inner member can include a flexible elongate body having a proximal end region, an outer diameter, a tapered distal tip portion, a distal opening, and a single lumen extending longitudinally through the flexible elongate body to the distal opening; and a proximal portion extending proximally from the proximal end region to a proximal-most end of the tapered inner member. When assembled, the tapered inner member extends through the lumen of the distal access catheter and the tapered distal tip portion extends distal to the distal end of the distal access catheter. The proximal portion of the tapered inner member can be a hypotube having an opening in fluid communication with the single lumen of the flexible elongate body. The flexible elongate body of the tapered inner member can include a proximal opening sized to accommodate a guidewire. The proximal opening can be located through a sidewall of the proximal end region of the flexible elongate body.

The method can further include arresting blood flow by expanding an occlusion balloon on an outer surface of a distal end region of the guide sheath.

In an interrelated aspect, disclosed is a method of accessing the intracranial neurovasculature using a catheter system including loading a guidewire within a microcatheter. The microcatheter including a lumen; a distal end region having a distal opening from the lumen; and a side opening from the lumen located a distance proximal to the distal opening. The guidewire, when loaded, is positioned within the lumen of the microcatheter such that a distal end of the guidewire extends out the distal opening and a proximal end of the guidewire exits the lumen at the side opening. A payload is housed within the lumen proximal to the side opening. The method includes inserting into a vessel of a patient the microcatheter loaded with the guidewire and the payload until the distal end region of the microcatheter is advanced into the intracranial neurovasculature.

The method can further include positioning within the vessel of the patient a guide sheath having a working lumen in communication with a port, the working lumen having a distal end. The method can further include inserting a distal access catheter through the port into the working lumen of the guide sheath, the distal access catheter having a lumen and a distal end, the distal end of the distal access catheter extending beyond the distal end of the guide sheath to at least a level of the internal carotid artery. The distal access catheter can further include a flexible distal luminal element having a proximal end, a proximal end region, a proximal opening; and a proximal extension extending proximally from a point of attachment adjacent the proximal opening. The proximal extension can be less flexible than the distal luminal element and configured to control movement of the distal access catheter. The proximal extension can have an outer diameter at the point of attachment that is smaller than an outer diameter of the distal luminal element at the point of attachment.

The method can further include positioning within the vessel of the patient a guide sheath having a working lumen in communication with a port. A distal end region of the guide sheath can further include an occlusion balloon on an outer surface configured to arrest flow through a vessel upon expansion of the sealing element.

The distal access catheter can be assembled with a tapered inner member forming an assembled coaxial catheter system. The tapered inner member can include a flexible elongate body having a proximal end region, an outer diameter, a tapered distal tip portion, a distal opening, and a single lumen extending longitudinally through the flexible elongate body to the distal opening; and a proximal portion extending proximally from the proximal end region to a proximal-most end of the tapered inner member. When assembled, the tapered inner member can extend through the lumen of the distal access catheter and the tapered distal tip portion extends distal to the distal end of the distal access catheter. The proximal portion of the tapered inner member can be a hypotube having an opening in fluid communication with the single lumen of the flexible elongate body. The flexible elongate body of the tapered inner member can include a proximal opening sized to accommodate a guidewire. The proximal opening can be located through a sidewall of the proximal end region of the flexible elongate body.

In an interrelated aspect, disclosed is a method of accessing the intracranial neurovasculature using a catheter system including inserting into a vessel of a patient a distal access catheter assembled with a tapered inner member forming an assembled coaxial catheter system. The distal access catheter includes a flexible distal luminal element having a proximal opening into a lumen extending between a proximal end and a distal end; and a proximal extension extending proximally from a point of attachment adjacent the proximal opening. The proximal extension is less flexible than the distal luminal element and configured to control movement of the distal access catheter. The proximal extension has an outer diameter at the point of attachment that is smaller than an outer diameter of the distal luminal element at the point of attachment. The tapered inner member includes a flexible elongate body having a proximal end region, an outer diameter, a tapered distal tip portion, a distal opening, and a single lumen extending longitudinally through the flexible elongate body to the distal opening; and a proximal portion extending proximally from the proximal end region to a proximal-most end of the tapered inner member. When assembled, the tapered inner member extends through the lumen of the distal access catheter and the tapered distal tip portion extends distal to the distal end of the distal access catheter. The method further includes removing the tapered inner member from the lumen of the distal access catheter; inserting a microcatheter into the lumen of the flexible distal luminal element. The microcatheter includes a lumen; a distal end region having a distal opening from the lumen; and a side opening from the lumen located a distance proximal to the distal opening. A payload is housed within the lumen proximal to the side opening. The method further includes advancing the microcatheter through the lumen of the distal access catheter until the distal end region of the microcatheter extends at least to the distal end of the distal access catheter.

The proximal portion of the tapered inner member can be a hypotube having an opening in fluid communication with the single lumen of the flexible elongate body. The method can further include inserting a second distal access catheter through the lumen of the first distal access catheter until the second distal access catheter extends distal to the first distal access catheter, wherein inserting the microcatheter into the lumen of the flexible distal luminal element further include inserting the microcatheter into the lumen of the second distal access catheter.

In an interrelated aspect, disclosed is a rapid exchange microcatheter system for accessing the intracranial neurovasculature including a catheter body having an outer diameter, an inner diameter, and a distal-most tip, an internal lumen defined by the inner diameter. The catheter body is adapted to carry a payload within the internal lumen and deliver the payload from the internal lumen to a target location in the intracranial neurovasculature. The inner diameter is sized to allow passage of a guidewire and the outer diameter has a maximum size of less than 0.048 inch. A guidewire side opening into the internal lumen is sized to allow passage of a guidewire. The guidewire side opening is located a distance between 10-20 cm from the distal-most tip of the catheter body. A proximal opening into the internal lumen that is different and distinct from the guidewire side opening is located a distance greater than 20 cm from the distal-most tip. A distal, reinforced catheter portion extends between a distal end region of the catheter body to a point near the guidewire side opening. A proximal, reinforced catheter portion extends a distance from a point near the guidewire side opening towards the proximal end of the catheter body. The guidewire side opening is positioned within a gap between a proximal end of the distal reinforced catheter portion and a distal end of the proximal, reinforced catheter portion. The system includes instructions for use that instruct that the payload be loaded in the internal lumen at a location proximal to the guidewire side opening prior to use of the catheter body.

In an interrelated aspect, disclosed is a rapid exchange microcatheter system for accessing the intracranial neurovasculature including a catheter body having an outer diameter, an inner diameter, and a distal-most tip. An internal lumen is defined by the inner diameter. The catheter body is adapted to carry a payload within the internal lumen and deliver the payload from the internal lumen to a target location in the intracranial neurovasculature. The inner diameter is sized to allow passage of a guidewire and the outer diameter body has a maximum size of less than 0.048 inch. A guidewire side opening into the internal lumen sized to allow passage of a guidewire is located a distance between 10-20 cm from the distal-most tip of the catheter body. A proximal opening into the internal lumen that is different and distinct from the guidewire side opening is located a distance greater than 20 cm from the distal-most tip. A distal, reinforced catheter portion extends between a distal end region of the catheter body to a point near the guidewire side opening. A proximal, reinforced catheter portion extends a distance from a point near the guidewire side opening towards the proximal end of the catheter body. The guidewire side opening is positioned within a gap between a proximal end of the distal reinforced catheter portion and a distal end of the proximal, reinforced catheter portion. The payload is loaded in the internal lumen at a location proximal to the guidewire side opening such that the payload can be carried within and delivered from the internal lumen to a target location in the intracranial neurovasculature.

In some variations, one or more of the following can optionally be included in any feasible combination in the above methods, apparatus, devices, and systems. More details of the devices, systems, apparatus, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

FIG. 4A is a cross-sectional view of first implementation of a proximal control element of a spined distal access catheter;

FIG. 4B is a cross-sectional view of another implementation of a proximal control element of a spined distal access catheter;

FIG. 4C is a cross-sectional view of the proximal control element of FIG. 4A within a working lumen of an access sheath;

FIG. 4D is a cross-sectional view of the proximal control element of FIG. 4B within a working lumen of an access sheath having a catheter advancement element extending therethrough;

FIG. 4E is a cross-sectional, schematic view comparing the surface area of the proximal control element of FIG. 4A and the proximal control element of FIG. 4B within the working lumen of an access sheath of FIG. 4D;

FIG. 7A is a side view of an implementation of a catheter advancement element;

FIG. 7B is a cross-sectional view of the catheter advancement element of FIG. 7A;

FIG. 7C is a detail view of FIG. 7B taken along circle C-C;

FIGS. 7F-7J are various views of an implementation of a proximal hub for coupling to the proximal portion shown in FIG. 7E;

FIGS. 9A-9I illustrate an implementation of a method of delivering a stent retriever using a single operator delivery system through a distal access system;

FIGS. 10A-10H illustrate an implementation of a method using a dual-headed rotating hemostatic valve;

FIGS. 13A-13B illustrate implementations of single operator working device delivery systems in a coaxial arrangement with a procedural guidewire;

FIG. 15B is a cross-sectional view of the microcatheter of FIG. 15A taken along line B-B;

FIG. 15C is a cross-sectional view of the microcatheter of FIG. 15A taken along line C-C;

FIG. 15D is a cross-sectional view of the microcatheter of FIG. 15A taken along line D-D;

FIG. 15E is a detail view of the microcatheter of FIG. 15A taken at circle E-E;

FIGS. 16A-16C illustrate top-down partial views of implementations of a rapid exchange microcatheter for delivering a working device to the neurovasculature for the treatment of stroke;

FIG. 20 illustrates an implementation of a coupler for the microcatheter of FIG. 16A-16C;

It should be appreciated that the drawings are for example only and are not meant to be to scale. It is to be understood that devices described herein may include features not necessarily depicted in each figure.

DETAILED DESCRIPTION

Figure 1A:
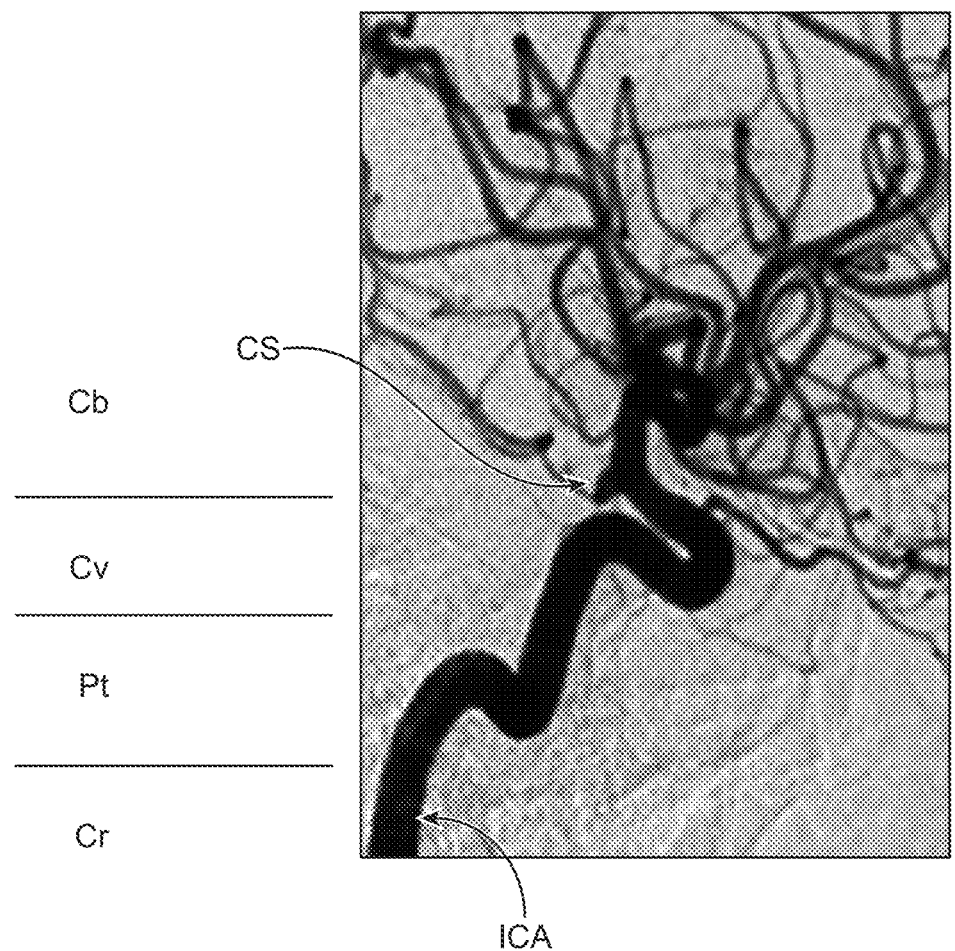
FIGS. 1A-1B illustrate the course of the terminal internal carotid artery through to the cerebral vasculature.

Navigating the carotid anatomy in order to treat various neurovascular pathologies at the level of the cerebral arteries, such as acute ischemic stroke (AIS), requires catheter systems having superior flexibility and deliverability. The internal carotid artery (ICA) arises from the bifurcation of the common carotid artery (CCA) at the level of the intervertebral disc between C3 and C4 vertebrae. As shown in FIG. 1A, the course of the ICA is divided into four parts—cervical Cr, petrous Pt, cavernous Cv and cerebral Cb parts. In the anterior circulation, the consistent tortuous terminal carotid is locked into its position by bony elements. The cervical carotid Cr enters the petrous bone and is locked into a set of turns as it is encased in bone. The cavernous carotid is an artery that passes through a venous bed, the cavernous sinus, and while flexible, is locked as it exits the cavernous sinus by another bony element, which surrounds and fixes the entry into the cranial cavity. Because of these bony points of fixation, the petrous carotid Pt and above are relatively consistent in their tortuosity. The carotid siphon CS is an S-shaped part of the terminal ICA. The carotid siphon CS begins at the posterior bend of the cavernous ICA and ends at the ICA bifurcation into the anterior cerebral artery ACA and middle cerebral artery MCA. The ophthalmic artery arises from the cerebral ICA, which represents a common point of catheter hang up in accessing the anterior circulation. These points of catheter hang up can significantly increase the amount of time needed to restore blood perfusion to the brain, which in the treatment of AIS is a disadvantage with severe consequences.

With advancing age, the large vessels often enlarge and lengthen. Fixed proximally and distally, the carotid often becomes tortuous. The common carotid artery CCA is relatively fixed in the thoracic cavity as it exits into the cervical area by the clavicle. The external and internal carotid arteries ECA, ICA are not fixed relative to the common carotid artery CCA, and thus they develop tortuosity with advancing age with lengthening of the entire carotid system. This can cause them to elongate and develop kinks and tortuosity or, in worst case, a complete loop or so-called "cervical loop". If catheters used to cross these kinked or curved areas are too stiff or inflexible, these areas can undergo a straightening that can cause the vessel to wrap around or "barbershop pole" causing focused kinking and folding of the vessel. These sorts of extreme tortuosity also can significantly increase the amount of time needed to restore blood perfusion to the brain, particularly in the aging population. In certain circumstances, the twisting of vessels upon themselves or if the untwisted artery is kinked, normal antegrade flow may be reduced to a standstill creating ischemia. Managing the unkinking or unlooping the vessels such as the cervical ICA can also increase the time it takes to perform a procedure.

A major drawback of current catheter systems for stroke intervention procedures is the amount of time required to restore blood perfusion to the brain, including the time it takes to access the occlusive site or sites in the cerebral artery and the time it takes to completely remove the occlusion in the artery. Because it is often the case that more than one attempt must be made to completely remove the occlusion, reducing the number of attempts as well as reducing the time required to exchange devices for additional attempts is an important factor in minimizing the overall time. Additionally, each attempt is associated with potential procedural risk due to device advancement in the delicate cerebral vasculature. Another limitation is the need for multiple operators to deliver and effectively manipulate long tri-axial systems typically used with conventional guide and distal access catheters.

Described herein are catheter systems for treating various neurovascular pathologies, such as acute ischemic stroke (AIS). The systems described herein provide quick and simple single-operator access to distal target anatomy, in particular tortuous anatomy of the cerebral vasculature. The medical methods, devices and systems described herein allow for navigating complex, tortuous anatomy to perform rapid and safe delivery of intracranial medical devices, with or without aspiration for the removal of cerebral occlusions in the treatment of acute ischemic stroke. The systems described herein can be particularly useful for the treatment of AIS whether a user intends to perform stent retriever delivery alone, aspiration alone, or a combination of aspiration and stent retriever delivery as a frontline treatment for AIS. Further, the extreme flexibility and deliverability of the distal access catheter systems described herein allow the catheters to take the shape of the tortuous anatomy rather than exert straightening forces creating new anatomy. The distal access catheter systems described herein can pass through tortuous loops while maintaining the natural curves of the anatomy therein decreasing the risk of vessel straightening. The distal access catheter systems described herein can thereby create a safe conduit through the neurovasculature maintaining the natural tortuosity of the anatomy for other catheters to traverse (e.g. interventional device delivery catheters). The catheters traversing the conduit need not have the same degree of flexibility and deliverability such that if they were delivered directly to the same anatomy rather than through the conduit, would lead to straightening, kinking, or folding of the anterior circulation.

It should be appreciated that while some implementations are described herein with specific regard to accessing a neurovascular anatomy or delivery of an expandable cerebral treatment device, the systems and methods described herein should not be limited to this and may also be applicable to other uses. For example, the catheter systems described herein may be used to deliver working devices to a target vessel of a coronary anatomy or other vasculature anatomy. It should also be appreciated that where the phrase "aspiration catheter" is used herein that such a catheter may be used for other purposes besides or in addition to aspiration, such as the delivery of fluids to a treatment site or as a support catheter or distal access catheter providing a conduit that facilitates and guides the delivery or exchange of other devices such as a guidewire or interventional devices such as stent retrievers. Alternatively, the access systems described herein may also be useful for access to other parts of the body outside the vasculature. Similarly, where the working device is described as being an expandable cerebral treatment device, stent retriever or self-expanding stent other interventional devices can be delivered using the delivery systems described herein.

Figure 2A:
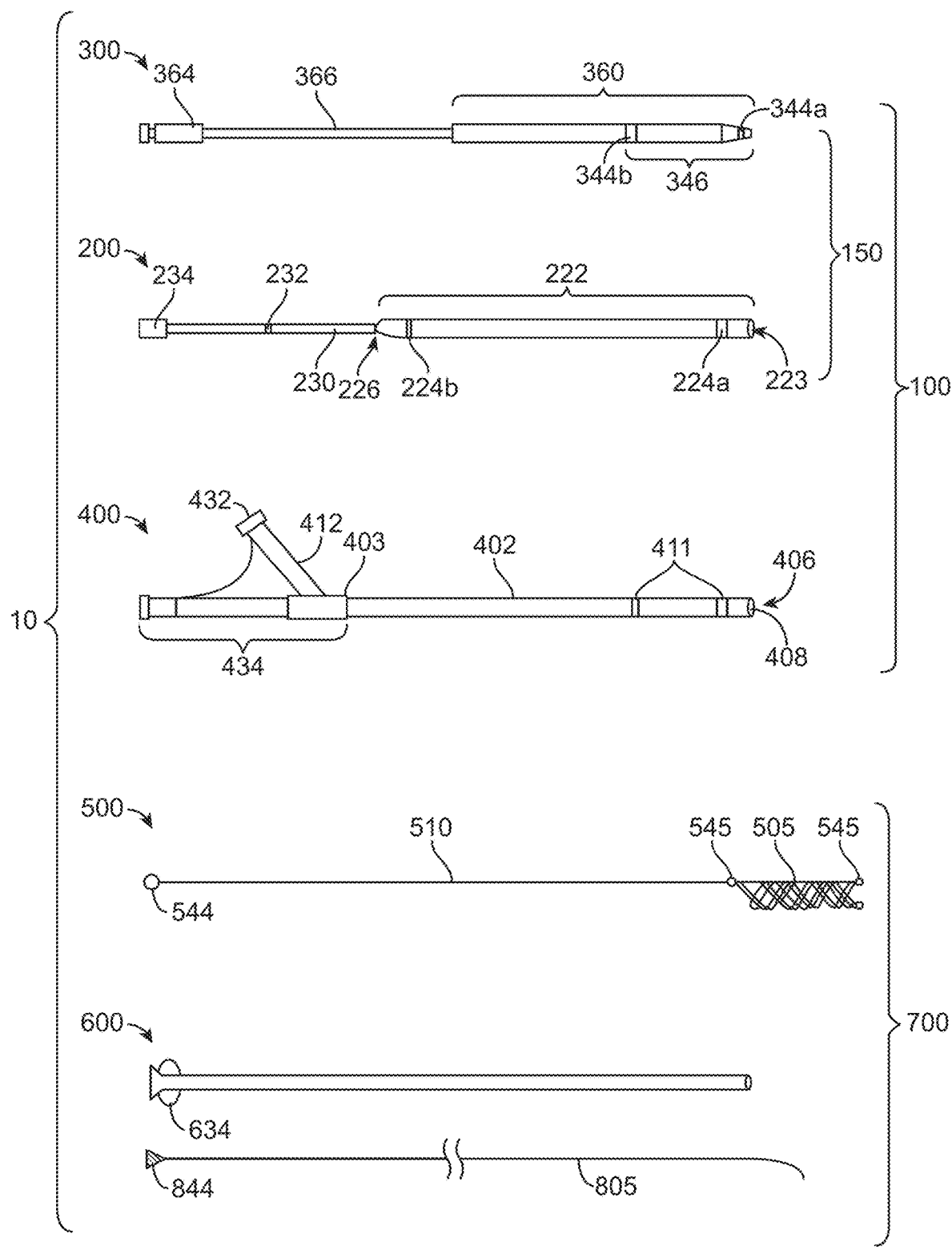
FIG. 2A is an exploded view of an implementation of a single operator delivery system including a distal access system and a working device delivery system.
Figure 2B:
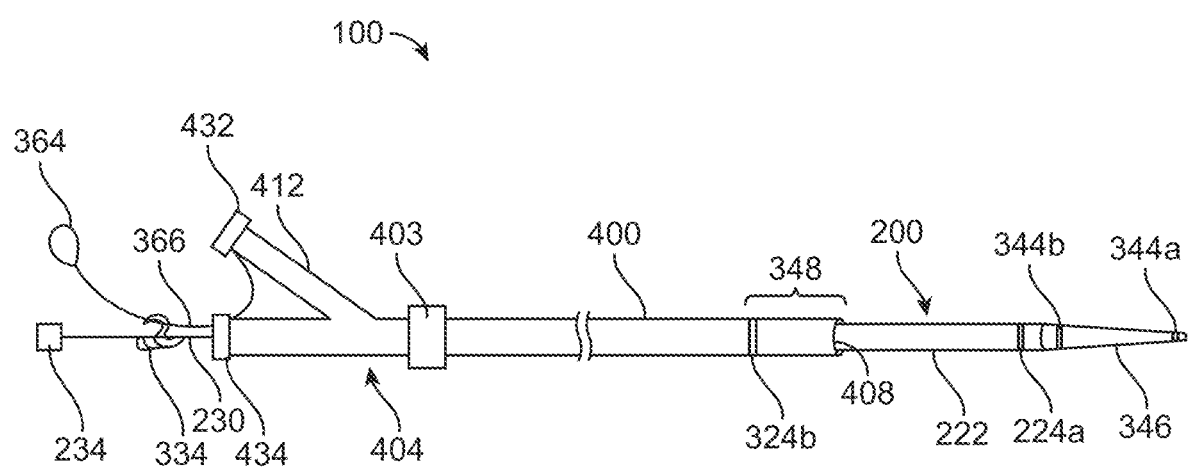
FIG. 2B is an assembled view of the distal access system of FIG. 2A.

Referring now to the drawings, FIGS. 2A-2B illustrate a system 10 including devices for accessing and removing a cerebral occlusion to treat acute ischemic stroke from an access site. The system 10 can be a single operator system such that each of the components and systems can be delivered and used together by one operator using minimal hand movements. As will be described in more detail below, all wire and catheter manipulations can occur at or in close proximity to a single rotating hemostatic valve (RHV) 434 or more than a single RHV co-located in the same device. The system 10 can include a distal access system 100 and an intracranial delivery system 700 each of which will be described in more detail below. The distal access system 100 can include a catheter 200 configured to be received through a guide sheath 400, the catheter 200 designed to have exceptional deliverability. The catheter 200 can be a spined, distal access catheter co-axial with a lumen of the guide sheath 400 thereby providing a step-up in inner diameter within the conduit. The catheter 200 can be delivered using a catheter advancement element 300 inserted through a lumen 223 of the catheter 200 forming a catheter delivery system 150. The intracranial delivery system 700 can include a cerebral treatment device or working device 500 for treatment of the cerebral occlusion. The working device 500 can have a distal expanding payload 505 and a proximal control element 510. The payload 505 is configured to be housed within an introducer sheath or microcatheter 600. The intracranial delivery system 700 can further include a procedural guidewire 805.

The distal access system 100 can create a variable length from point of entry at the percutaneous arteriotomy (e.g. the femoral artery) to the target control point of the distal catheter. Conventional distal access systems for stroke intervention typically include a long guide sheath or guide catheter placed through a shorter "introducer" sheath (e.g. 11-30 cm in length) at the groin. The long guide sheath is typically positioned in the ICA to support neurovascular interventions including stroke thrombectomy. For added support, these can be advanced up to the bony terminal petrous and rarely into the cavernous or clinoid or supraclinoid terminal ICA when possible. To reach targets in the M1 or M2 distribution for ADAPT/MAT or Solumbra/SMAT approaches, an additional catheter is inserted through the long guide catheter. These catheters are typically large-bore aspiration catheters that can be 130 cm in length or longer. As will be described in more detail below, the distal access systems 100 described herein can be shorter, for example, only 115 cm in length, allowing for a shorter intracranial working device delivery system 700 to be used with the distal access system 100 providing an ease of use advantage more suitable for a single operator. Additionally, the single operator can use the systems described herein by inserting them through a single rotating hemostatic valve (RHV) 434 on the guide sheath 400 or more than one RHV co-located in the same device such as a dual-headed RHV. Thus, what was once a two-person procedure can be a one-person procedure.

Each of the various components of the various systems will now be described in more detail.

Distal Access System

Again with respect to FIGS. 2A-2D (as well as FIGS. 8A-8C, 9A-9I, and 10A-10H), the distal access system 100 can include an access guide sheath 400 having a body 402 through which a working lumen 410 extends from a proximal hemostasis valve 434 coupled to a proximal end region 403 of the body 402 to a distal opening 408 of a distal end region. The working lumen 410 is configured to receive the support catheter 200 of the distal access system 100 therethrough such that a distal end of the catheter 200 extends beyond a distal end of the sheath 400 through the distal opening 408. The guide sheath 400 can be used to deliver the catheters described herein as well as any of a variety of working devices known in the art. For example, the working devices can be configured to provide thrombotic treatments and can include large-bore catheters, aspiration thrombectomy, advanced catheters, wires, balloons, retrievable structures such as coil-tipped retrievable stents "Stentriever". The guide sheath 400 in combination with the support catheter 200 can also be used to apply distal aspiration as will be described in more detail below.

The guide sheath 400 can be any of a variety of commercially available guide sheaths. For example, the guide sheath 400 can have an internal diameter (ID) between 0.087"-0.089" such as the Cook SHUTTLE 6 F (Cook Medical, Inc., Bloomington, Ind.), Terumo DESTINATION 6 F (Terumo Europe NV), Cordis VISTA BRITE TIP (Cordis Corp., Hialeah, Fla.), and Penumbra NEURON MAX 088 (Penumbra, Inc., Alameda, Calif.), or comparable commercially available guiding sheath. Generally, sheath sizes are described herein using the French (F) scale. For example, where a sheath is described as being 6 French, it should be appreciated that the inner diameter of that sheath is able to receive a catheter having a 6 F outer diameter, which is about 1.98 mm or 0.078". It should be appreciated, therefore, that a catheter may be described herein as having a particular size in French to refer to the compatibility of its inner diameter to receive an outer diameter of another catheter. A catheter may also be described herein as having a particular size in French to refer to its outer diameter being compatible with another catheter having a particular inner diameter.

Again with respect to FIGS. 2A-2D, the elongated body 402 can extend from a proximal furcation or rotating hemostatic valve (RHV) 434 at a proximal end region 403 to a tip 406 at a distal end of the body 402. The proximal RHV 434 may include one or more lumens molded into a connector body to connect to the working lumen 410 of the body 402 of the guide sheath 400. As described above, the working lumen 410 can receive the catheter 200 and/or any of a variety of working devices for delivery to a target anatomy. The RHV 434 can be constructed of thick-walled polymer tubing or reinforced polymer tubing. The RHV 434 allows for the introduction of devices through the guide sheath 400 into the vasculature, while preventing or minimizing blood loss and preventing air introduction into the guide sheath 400. The RHV 434 can be integral to the guide sheath 400 or the guide sheath 400 can terminate on a proximal end in a female Luer adaptor to which a separate hemostasis valve component, such as a passive seal valve, a Tuohy-Borst valve or rotating hemostasis valve may be attached. The RHV 434 can have an adjustable opening that is open large enough to allow removal of devices that have adherent clot on the tip without causing the clot to dislodge at the RHV 434 during removal. Alternately, the RHV 434 can be removable such as when a device is being removed from the sheath 400 to prevent clot dislodgement at the RHV 434. The RHV 434 can be a dual RHV.

The RHV 434 can form a Y-connector on the proximal end 403 of the sheath 400 such that the first port of the RHV 434 can be used for insertion of a working catheter into the working lumen 410 of the sheath 400 and a second port into arm 412 can be used for another purpose. For example, a syringe or other device can be connected at arm 412 via a connector 432 to deliver a forward drip, a flush line for contrast or saline injections through the body 402 toward the tip 406 and into the target anatomy. Arm 412 can also connect to a large-bore aspiration line and an aspiration source (not shown) such as a syringe or pump to draw suction through the working lumen 410. The arm 412 can also allow the guide sheath 400 to be flushed with saline or radiopaque contrast during a procedure. The working lumen 410 can extend from a distal end to a working proximal port of the proximal end region 403 of the elongated body 402.

The length of the elongated body 402 is configured to allow the distal tip 406 of the body 402 to be positioned as far distal in the internal carotid artery (ICA), for example, from a transfemoral approach with additional length providing for adjustments if needed. In some implementations, the length of the body 402 can be in the range of 80 to 90 cm although it should be appreciated that the of the body 402 can be longer, for example, up to about 100 cm or up to about 105 cm. In implementations, the body 402 length is suitable for a transcarotid approach to the bifurcation of the carotid artery, in the range of 20-25 cm. In further implementations, the body 402 length is suitable for a transcarotid approach to the CCA or proximal ICA, and is in the range of 10-15 cm. The body 402 is configured to assume and navigate the bends of the vasculature without kinking, collapsing, or causing vascular trauma, even, for example, when subjected to high aspiration forces.

The tip 406 of the guide sheath 400 can have a same or similar outer diameter as a section of the body 402 leading up to the distal end. Accordingly, the tip 406 may have a distal face orthogonal to a longitudinal axis passing through the body 402 and the distal face may have an outer diameter substantially equal to a cross-sectional outer dimension of the body 402. In an implementation, the tip 406 includes a chamfer, fillet, or taper, making the distal face diameter slightly less than the cross-sectional dimension of the body 402. In a further implementation, the tip 406 may be an elongated tubular portion extending distal to a region of the body 402 having a uniform outer diameter such that the elongated tubular portion has a reduced diameter compared to the uniform outer diameter of the body 402. Thus, the tip 406 can be elongated or can be more bluntly shaped. Accordingly, the tip 406 may be configured to smoothly track through a vasculature and/or to dilate vascular restrictions as it tracks through the vasculature. The working lumen 410 may have a distal end forming a distal opening 408.

The guide sheath 400 may include a tip 406 that tapers from a section of the body 402 leading up to the distal end. That is, an outer surface of the body 402 may have a diameter that reduces from a larger dimension to a smaller dimension at a distal end. For example, the tip 406 can taper from an outer diameter of approximately 0.114" to about 0.035". The angle of the taper of the tip 406 can vary depending on the length of the tapered tip 406. For example, in some implementations, the tip 406 tapers from 0.110" to 0.035" over a length of approximately 50 mm.

In an implementation, the guide sheath 400 includes one or more radiopaque markers 411. The radiopaque markers 411 can be disposed near the distal tip 406. For example, a pair of radiopaque bands may be swaged, painted, embedded, or otherwise disposed in or on the body 402. In some implementations, the radiopaque markers 411 include a barium polymer, tungsten polymer blend, tungsten-filled or platinum-filled marker that maintains flexibility of the distal end of the device and improves transition along the length of the guide sheath 400 and its resistance to kinking. In some implementations, the radiopaque marker 411 is a tungsten-loaded PEBAX or polyurethane that is heat welded to the body 402. The markers 411 are shown in the figures as rings around a circumference of one or more regions of the body 402. However, the markers 411 can have other shapes or create a variety of patterns that provide orientation to an operator regarding the position of the distal opening 408 within the vessel. Accordingly, an operator may visualize a location of the distal opening 408 under fluoroscopy to confirm that the distal opening 408 is directed toward a target anatomy where a catheter 200 is to be delivered. For example, radiopaque marker(s) 411 allow an operator to rotate the body 402 of the guide sheath 400 at an anatomical access point, e.g., a groin of a patient, such that the distal opening provides access to an ICA by subsequent working device(s), e.g., catheters and wires advanced to the ICA. In some implementations, the radiopaque marker(s) 411 include platinum, gold, tantalum, tungsten or any other substance visible under an x-ray fluoroscope. It should be appreciated that any of the various components of the systems described herein can incorporate radiopaque markers as described above.

In some implementations, the guide sheath 400 will have performance characteristics similar to other sheaths used in carotid access and AIS procedures in terms of kinkability, radiopacity, column strength, and flexibility. The inner liners can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liners and can be constructed from materials such as PEBAX, thermoplastic polyurethane, polyethylene, nylon, or the like. A third layer can be incorporated that can provide reinforcement between the inner liner and the outer jacket. The reinforcement layer can prevent flattening or kinking of the inner lumen of the body 402 to allow unimpeded device navigation through bends in the vasculature as well as aspiration or reverse flow. The body 402 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another implementation, the reinforcement layer can be a cut hypotube such as a Nitinol hypotube or cut rigid polymer, or the like. The outer jacket of the body 402 can be formed of increasingly softer materials towards the distal end. For example, proximal region of the body 402 can be formed of a material such as Nylon, a region of the body 402 distal to the proximal region of the body 402 can have a hardness of 72D whereas areas more distal can be increasingly more flexible and formed of materials having a hardness of 55D, 45D, 35D extending towards the distal tip 406, which can be formed of a material having a hardness of 35D, for example. The body 402 can include a hydrophilic coating.

The flexibility of the body 402 can vary over its length, with increasing flexibility towards the distal portion of the body 402. The variability in flexibility may be achieved in various ways. For example, the outer jacket may change in durometer and/or material at various sections. A lower durometer outer jacket material can be used in a distal section of the guide sheath compared to other sections of the guide sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the elongate body 402. In another implementation, there is a transition section between the distal-most flexible section and the proximal section, with one or more sections of varying flexibilities between the distal-most section and the remainder of the elongate body 402. In this implementation, the distal-most section is about 2 cm to about 5 cm, the transition section is about 2 cm to about 10 cm and the proximal section takes up the remainder of the sheath length.

The different inner diameters of the guide sheaths 400 can be used to receive different outer diameter catheters 200. In some implementations, the working lumen 410 of a first guide sheath 400 can have an inner diameter sized to receive a 6 F catheter and the working lumen 410 of a second guide sheath 400 can have an inner diameter sized to receive a 8 F catheter. In some implementations, the distal region of the guide sheath 400 can have an inner diameter of about 0.087" to 0.088". The guide sheaths 400 can receive catheters having an outer diameter that is snug to these inner diameter dimensions. It should be appreciated that the guide sheath 400 (as well as any of the variety of components used in combination with the sheath 400) can be an over-the-wire (OTW) or rapid exchange type device, which will be described in more detail below.

In some instances it is desirable for the sheath body 402 to also be able to occlude the artery in which it is positioned, for example, during procedures that may create distal emboli. Occluding the artery stops antegrade blood flow and thereby reduces the risk of distal emboli that may lead to neurologic symptoms such as TIA or stroke. FIG. 2D shows an arterial access device or sheath 400 that has a distal occlusion balloon 440 that upon inflation occludes the artery at the position of the sheath distal tip 406. At any point in a procedure, for example, during removal of an occlusion by aspiration and/or delivery of a stentriever or other interventional device, the occlusion balloon 440 can be inflated to occlude the vessel to reduce the risk of distal emboli to cerebral vessels. The sheath 400 can include an inflation lumen configured to deliver a fluid for inflation of the occlusion balloon 440 in addition to the working lumen of the sheath 400. The inflation lumen can fluidly connect the balloon 440, for example, to arm 412 on the proximal adaptor. This arm 412 can be attached to an inflation device such as a syringe to inflate the balloon 440 with a fluid when vascular occlusion is desired. The arm 412 may be connected to a passive or active aspiration source to further reduce the risk of distal emboli.

According to some implementations, the length of the guide sheath 400 is long enough to access the target anatomy and exit the arterial access site with extra length outside of a patient's body for adjustments. For example, the guide sheath 400 (whether having a distal occlusion balloon 440 or not) can be long enough to access the petrous ICA from the femoral artery such that an extra length is still available for adjustment. The guide sheath 400 can be a variety of sizes to accept various working devices and can be accommodated to the operator's preference. For example, current MAT and SMAT techniques describe delivering aspiration catheters having inside diameters of 0.054"-0.072" to an embolus during AIS. Accordingly, the working lumen 410 of the guide sheath 400 can be configured to receive the catheter 200 as well as other catheters or working devices known in the art. For example, the working lumen 410 can have an inner diameter sized to accommodate at least 6 French catheters (1.98 mm or 0.078" OD), or preferably at least 6.3 French catheters (2.079 mm or 0.082" OD). The inner diameter of the guide sheath 400, however, may be smaller or larger to be compatible with other catheter sizes. In some implementations, the working lumen 410 can have an inner diameter sized to accommodate 7 French (2.31 mm or 0.091" OD) catheters or 8 French (2.64 mm or 0.104" OD) or larger catheters. In some implementations, the working lumen 410 can have an inner diameter that is at least about 0.054" up to about 0.070", 0.071", 0.074", 0.087", 0.088", or 0.100" and thus, is configured to receive a catheter 200 having an outer diameter that fits snug with these dimensions. Regardless of the length and inner diameter, the guide sheath 400 is resistant to kinking during distal advancement through the vasculature.

The working lumen 410 included in the sheath 400 can be sized to receive its respective working devices in a sliding fit. The working lumen 410 may have an inner diameter that is at least 0.001 inch larger than an outer diameter of any catheter 200 it is intended to receive, particularly if the catheter 200 is to be used for aspiration as will be described in more detail below. As described in more detail below, the catheter 200 can include a slit 236 in the luminal portion 222 configured to widen slightly upon application of suction from an aspiration source and improve sealing between the catheter 200 and the guide sheath 400. The strength of the seal achieved allows for a continuous aspiration lumen from the distal tip of the catheter 200 to a proximal end 403 of the guide sheath 400 where it is connected to an aspiration source, even in the presence of lower suction forces with minimal to no leakage. Generally, when there is enough overlap between the catheter 200 and the guide sheath 400 there is no substantial leakage. However, when trying to reach distal anatomy, the catheter 200 may be advanced to its limit and the overlap between the catheter 200 and the guide sheath 400 is minimal. Thus, additional sealing can be desirable to prevent leakage around the catheter 200 into the sheath 400. The sealing between the catheter 200 and the guide sheath 400 can prevent this leakage upon maximal extension of catheter 200 relative to sheath 400.

Distal Access Catheter

Figure 1B:
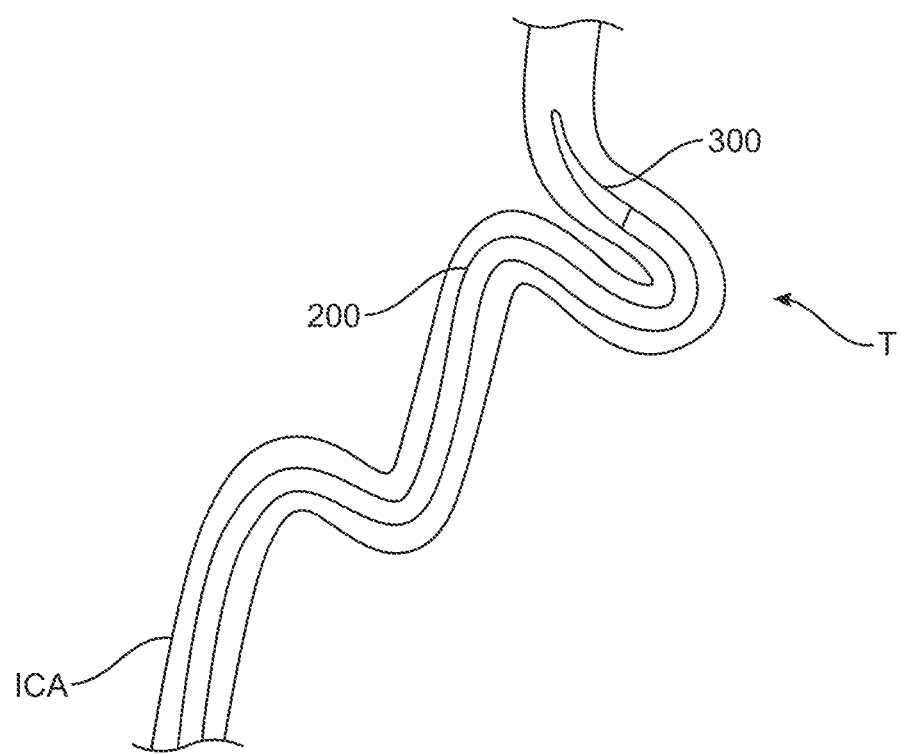
Figure 2C:
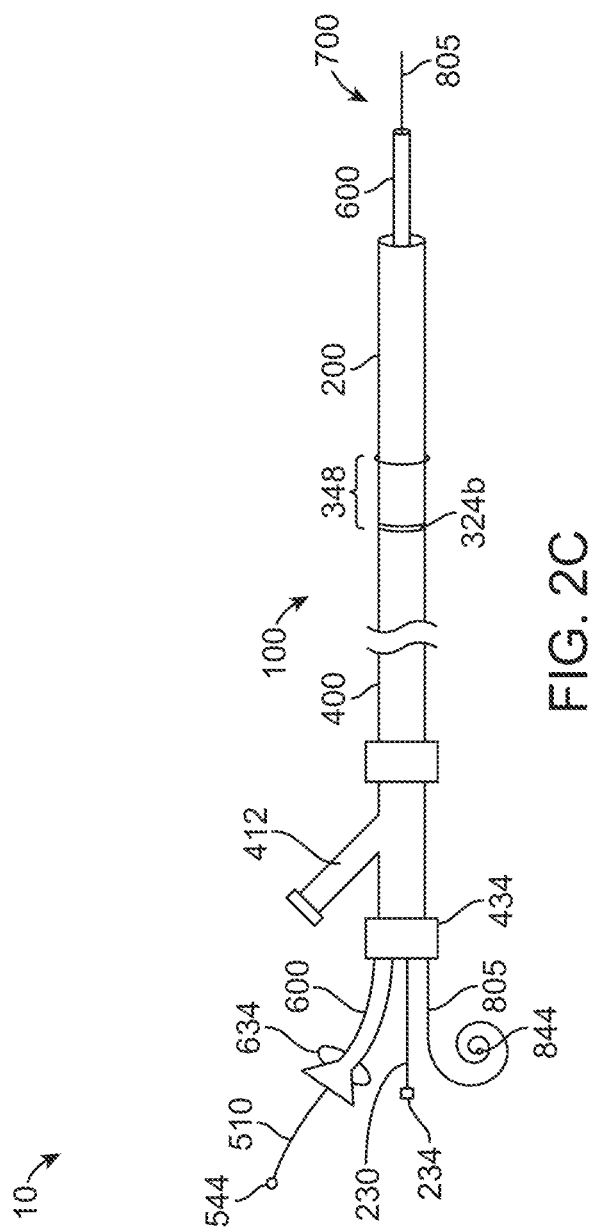
FIG. 2C is an assembled view of the working device delivery system extending through the distal access system of FIG. 2A.
Figure 3:
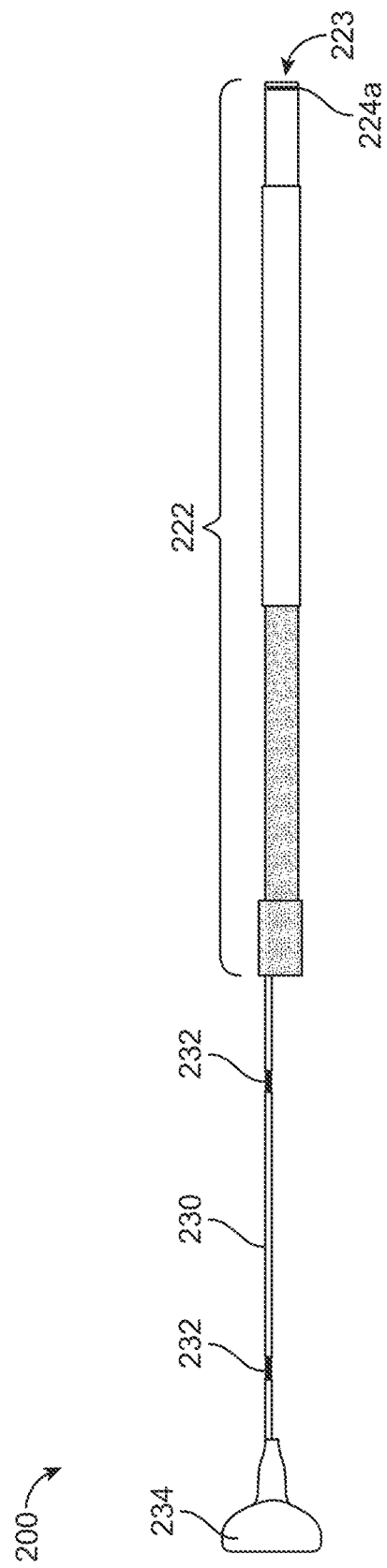
FIG. 3 is a side view of an implementation of a spined distal access catheter.

Again with respect to FIGS. 2A-2C and also FIG. 3, the distal access system 100 can include a distal access or support catheter 200 configured to extend through and out the distal end of the guide sheath 400. FIG. 3 illustrates a side elevational view of an implementation of the support catheter 200. The catheter 200 can include a relatively flexible, distal luminal portion 222 coupled to a more rigid, kink-resistant proximal control element 230. The support catheter 200 provides a quick way to access stroke locations with simplicity even through the extreme tortuosity of the cerebral vasculature. The support catheters described herein have a degree of flexibility and deliverability that makes them optimally suitable to be advanced through the cerebral vascular anatomy without kinking or ovalizing even when navigating hairpin turns. For example, the distal luminal portion 222 can perform a 180 degree turn (see turn T shown in FIG. 1B near the carotid siphon) and maintain a folded width across of 4.0 mm without kinking or ovalizing. Further, the distal luminal portion 222 has a degree of flexibility that maintains the natural tortuosity of the vessels through which it is advanced without applying straightening forces such that the natural shape and curvature of the anatomy is maintained during use. The support catheter 200, particularly in combination with a catheter advancement element 300, which will be described in more detail below, provides an extended conduit beyond the guide sheath 400 having exceptional deliverability through convoluted anatomy that allows for delivering aspirational forces to a target stroke site as well as for the delivery of stroke interventional devices such as a stent retriever, stent, flow diverter or other working devices.

An inner lumen 223 extends through the luminal portion 222 between a proximal end and a distal end of the luminal portion 222. The inner lumen 223 of the catheter 200 can have a first inner diameter and the working lumen 410 of the guide sheath 400 can have a second, larger inner diameter. Upon insertion of the catheter 200 through the working lumen 410 of the sheath 400, the lumen 223 of the catheter 200 can be configured to be fluidly connected and contiguous with the working lumen 410 of the sheath 400 such that fluid flow into and/or out of the system 100 is possible, such as by applying suction from an aspiration source coupled to the system 100 at a proximal end. The combination of sheath 400 and catheter 200 can be continuously in communication with the bloodstream during aspiration at the proximal end with advancement and withdrawal of catheter 200.

The spined catheter system can create advantages for distal access over conventional catheters particularly in terms of aspiration. The step change in the internal diameter of the catheter column creates a great advantage in aspiration flow and force that can be generated by the spined catheter 200 in combination with the conventional guide catheter. For example, where a spined catheter 200 with a 0.070" internal diameter is paired with a standard 6 F outer diameter/0.088" internal diameter guide catheter (e.g. Penumbra Neuron MAX 088) can create aspiration physics where the 0.088" catheter diameter will predominate and create a 0.080 equivalent flow in the entire system.

In addition to aspiration procedures, the support catheter 200 and distal access system 100 can be used for delivery of tools and interventional working devices. As will be described in more detail below, a typical stent retriever to be delivered through the support catheter 200 can have a push wire control element of 180 cm. The distal access system 100 having a spined support catheter 200 allows for reaching distal stroke sites using much shorter lengths (e.g. 120 cm-150 cm). The overall length can be as important as diameter and radius on aspiration through the catheter. The shorter lengths in combination with the elimination of the multiple RHVs typical in tri-axial systems allows for a single-operator use.

It should be appreciated that where the distal access catheter is described herein as an aspiration catheter it should not be limited to only aspiration. Similarly, where the catheter is described herein as a way to deliver a stent retriever or other working device 500 it should not be limited as such. It should also be appreciated that the systems described herein can be used to perform procedures that incorporate a combination of treatments. For example, the support catheter 200 can be used for the delivery of a stent retriever delivery system, optionally in the presence of aspiration through the support catheter 200. As another example, a user may start out performing a first interventional procedure using the systems described herein, such as aspiration thrombectomy, and switch to another interventional procedure, such as delivery of a stent retriever or implant.

It should also be appreciated that the catheter 200 need not be spined or include the proximal control element 230 and instead can be a non-spined, conventional catheter having a uniform diameter. The terms "support catheter", "spined catheter", "distal access catheter", and "intermediate catheter" may be used interchangeably herein.

It is desirable to have a catheter 200 having an inner diameter that is as large as possible that can be navigated safely to the site of the occlusion, in order to optimize the aspiration force in the case of aspiration and/or provide ample clearance for delivery of a working device. A suitable size for the inner diameter of the distal luminal portion 222 may range between 0.040" and 0.100", depending on the patient anatomy and the clot size and composition. The outer diameter of the distal luminal portion 222 can be sized for navigation into cerebral arteries, for example, at the level of the M1 segment or M2 segment of the cerebral vessels. The outer diameter (OD) should be as small as possible while still maintaining the mechanical integrity of the catheter 200. In an implementation, the difference between the OD of distal luminal portion 222 of the catheter 200 and the inner diameter of the working lumen 410 of the guide sheath 400 is between 0.001" and 0.002". In another implementation, the difference is between 0.001" and 0.004".

In some implementations, the distal luminal portion 222 of the catheter 200 has an outer diameter (OD) configured to fit through a 6 F introducer sheath (0.071") and the lumen 223 has an inner diameter (ID) that is sized to receive a 0.054" catheter. In some implementations, the distal luminal portion 222 of the catheter 200 has an OD configured to fit through an 8 F introducer sheath (0.088") and the lumen 223 has an ID that is sized to receive a 0.070" or 0.071" catheter. In some implementations, the OD of the distal luminal portion 222 is 2.1 mm and the lumen 223 has an ID that is 0.071". In some implementations, the lumen 223 has an ID that is 0.070" to 0.073". The outer diameter of the guide sheath 400 can be suitable for insertion into at least the carotid artery, with a working lumen 410 suitably sized for providing a passageway for the catheter 200 to treat an occlusion distal to the carotid artery towards the brain. In some implementations, the ID of the working lumen 410 can be about 0.074" and the OD of the body of the guide sheath 400 can be about 0.090", corresponding to a 5 French sheath size. In some implementations, the ID of the working lumen 410 can be about 0.087" and the OD of the body of the guide sheath 400 can be about 0.104", corresponding to a 6 French sheath size. In some implementations, the ID of the working lumen 410 can be about 0.100" and the OD of the body of the guide sheath 400 can be about 0.117", corresponding to a 7 French sheath size. In some implementations, the guide sheath 400 ID is between 0.087" and 0.088" and the OD of the distal luminal portion 222 of the catheter 200 is approximately 0.082" and 0.086" such that the difference in diameters is between 0.001" and 0.005".

In an implementation, the luminal portion 222 of the catheter 200 has a uniform diameter from a proximal end to a distal end. In other implementations, the luminal portion 222 of the catheter 200 is tapered and/or has a step-down towards the distal end of the distal luminal portion 222 such that the distal-most end of the catheter 200 has a smaller outer diameter compared to a more proximal region of the catheter 200, for example near where the distal luminal portion 222 seals with the guide sheath 400. In another implementation, the luminal portion 222 of the catheter OD steps up at or near an overlap portion to more closely match the sheath inner diameter as will be described in more detail below. This implementation is especially useful in a system with more than one catheter suitable for use with a single access sheath size. It should be appreciated that smaller or larger sheath sizes are considered herein.

Figure 2D:
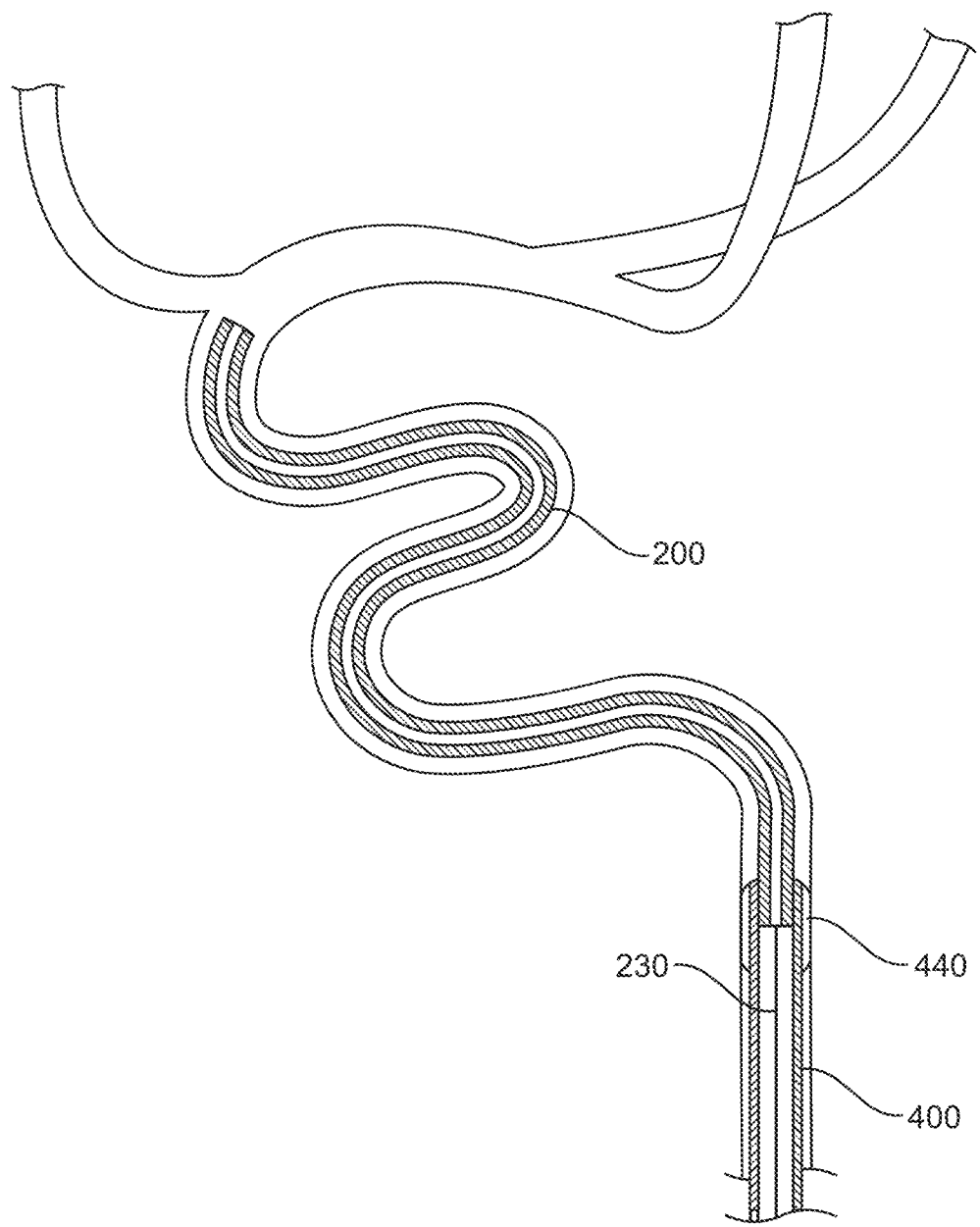
FIG. 2D illustrates an implementation of an arterial access device having a distal occlusion balloon.

The length of the luminal portion 222 can be shorter than a length of the working lumen 410 of the guide sheath 400 such that upon advancement of the luminal portion 222 towards the target location results in a short overlap region 348 between the luminal portion 222 and the working lumen 410 remains (see FIGS. 2B-2C). Taking into account the variation in occlusion sites and sites where the guide sheath 400 distal tip 406 may be positioned, the length of the luminal portion 222 may range from about 10 cm to about 40 cm. In some implementations, the distal luminal portion 222 of the catheter 200 can be between 20-40 cm and the control element 230 of the catheter 200 can be between about 90-100 cm such that the catheter 200 can have a total working length that is approximately 115 cm. The body 402 of the guide sheath 400 can be between 80-90 cm. In other implementations, the working length of the catheter 200 between a proximal end of the catheter to a distal end of the catheter can be greater than 115 cm up to about 130 cm. In some implementations, the catheter 200 can have a working length of 133 cm between a proximal tab 234 (or proximal hub) and the distal tip, the distal luminal portion 222 can have a shaft length of about 38.7 mm.

The length of the luminal portion 222 can be less than the length of the body 402 of the guide sheath 400 such that as the catheter 200 is extended from the working lumen 410 there remains a seal between the overlap region 348 of the catheter 200 and the inner diameter of the working lumen 410. In some implementations, the length of the luminal portion 222 is sufficient to reach a region of the M1 segment of the middle cerebral artery (MCA) and other major vessels from a region of the internal carotid artery such that the proximal end region of the luminal portion 222 of the catheter 200 avoids extending within the aortic arch. This limits the number of severe angulations the luminal portion 222 of the catheter 200 must navigate while still reaching target sites in the more distal cerebral anatomy. Used in conjunction with a guide sheath 400 having a sheath body 402 and a working lumen 410, in an implementation where the catheter 200 reaches the ICA and the distance to embolus can be less than 20 cm.

The distal luminal portion 222 having a length of approximately 25 cm can allow for an overlap region 348 with the body 402 to create a seal. The overlap region 348 can be maintained between the working lumen 410 of the guide sheath 400 near a distal end region of the sheath body 402 and the luminal portion 222 of the catheter 200 upon extension of the luminal portion 222 into the target anatomy. It should be appreciated where the OD of the catheter 200 along at least a portion of the distal luminal portion 222 substantially matches the inner diameter of the guide sheath 400 or the difference can be between 0.001"-0.002", a seal to fluid being injected or aspirated can be achieved by the overlap region 348. The difference between the catheter OD and the inner diameter of the guide sheath 400 can vary, for example, between 1-2 thousandths of an inch, or between 1-4 thousandths of an inch, or between 1-12 thousandths of an inch. A seal to fluid being injected or aspirated between the catheter and the sheath can be achieved by the overlap 348 between their substantially similar dimensions without incorporating any separate sealing structure or seal feature.

The overlap region 348 can have a length of a few centimeters and may vary depending on the distance from the embolus to the distal end of the distal luminal portion 222, e.g., depending on how far the catheter 200 is advanced relative to the guide sheath 400. The overlap region 348 is sized and configured to create a seal that allows for a continuous aspiration lumen from the distal tip region of the catheter 200 to a proximal end region 403 of the guide sheath 400 where it can be connected to an aspiration source. The strength of the seal achieved can be a function of the difference between the outer diameter of the catheter 200 and the inner diameter of the working lumen 410 as well as the length of the overlap region 348, the force of the suction applied, and the materials of the components. For example, the sealing can be improved by increasing the length of the overlap region 348. However, increasing the length of the overlap region 348 can result in a greater length through which aspiration is pulled through the smaller diameter of the luminal portion 222 rather than the larger diameter of the working lumen 410. As another example, higher suction forces applied by the aspiration source can create a stronger seal between the luminal portion 222 and the working lumen 410 even in the presence of a shorter overlap region 348. Further, a relatively softer material forming the luminal portion and/or the body 402 can still provide a sufficient seal even if the suction forces are less and the overlap region 348 is shorter. In an implementation, the overlap region 348 is configured to enable sealing against a vacuum of up to 28 inHg. In an implementation, the overlap region 348 is configured to enable sealing against a pressure of up to 300 mmHg or up to 600 mmHg or up to 700 mmHg with minimal to no leakage.

It should be appreciated that sealing at the overlap region can be due to the small difference in inner and outer diameters and/or can be due to an additional sealing element positioned on an external surface of the distal luminal portion or an inner surface of the sheath body. A sealing element can include a stepped up diameter or protruding feature in the overlap region. The sealing element can include one or more external ridge features. The one or more ridge features can be compressible when the luminal portion is inserted into the lumen of the sheath body. The ridge geometry can be such that the sealing element behaves as an O-ring, quad ring, or other piston seal design. The sealing element can include one or more inclined surfaces biased against an inner surface of the sheath body lumen. The sealing element can include one or more expandable members actuated to seal. The inflatable or expandable member can be a balloon or covered braid structure that can be inflated or expanded and provide sealing between the two devices at any time, including after the catheter is positioned at the desired site. Thus, no sealing force need be exerted on the catheter during positioning, but rather applied or actuated to seal after the catheter is positioned. The sealing element can be positioned on the external surface of the distal luminal portion, for example, near the proximal end region of the distal luminal portion and may be located within the overlap region. More than a single sealing element can be positioned on a length of the catheter.

In some implementations, the additional sealing element can be a cup seal, a balloon seal, or a disc seal formed of a soft polymer positioned around the exterior of the distal luminal portion near the overlap region to provide additional sealing. The sealing element can be a thin-wall tubing with an outer diameter that substantially matches the inner diameter of the sheath body lumen. The tubing can be sealed on one end to create a cup seal or on both ends to create a disc or balloon seal. The balloon seal can include trapped air that creates a collapsible space. One or more slits can be formed through the wall tubing such that the balloon seal can be collapsible and more easily passed through an RHV. The balloon seal need not include slits for a less collapsible sealing element that maintains the trapped air. The sealing element can be tunable for sheath fit and collapse achieved.

Again with respect to FIG. 3, the proximal control element 230 is configured to move the distal luminal portion 222 in a bidirectional manner through the working lumen 410 of the guide sheath 400 such that the distal luminal portion 222 can be advanced out of the guide sheath 400 into a target location for treatment within the target vessel. In some implementations and as shown in FIG. 3, the proximal control element 230 of the catheter 200 can have a smaller outer diameter than the outer diameter of the distal luminal portion 222 forming a proximal spine or tether to the catheter 200. A smaller outer diameter for the proximal control element 230 than the outer diameter of the distal luminal portion 222 allows for the larger diameter working lumen 410 of the sheath 400 to maintain greater aspiration forces than would otherwise be provided by the smaller diameter luminal portion 222 of the catheter 200 or allow for the delivery of working devices through the lumen with less frictional forces. The markedly shorter length of the luminal portion 222 results in a step-up in luminal diameter between the luminal portion 222 contiguous with the working lumen 410 providing a markedly increased radius and luminal area for delivery of a working device and/or aspiration of the clot, particularly in comparison to other systems where the aspiration lumen runs along the entire inner diameter of the aspiration catheter. More particularly, the combined volume of the luminal area of the catheter 200 and the luminal area of the working lumen 410 proximal to the distal luminal portion 222 is greater than the luminal area of the large bore catheter along the entire length of the system. Thus, the likelihood of removing the embolus during a single aspiration attempt may be increased. More particularly, the stepped up luminal diameter along the proximal control element 230 may enable a greater aspiration force to be achieved resulting in improved aspiration of the embolus. Further, this configuration of the catheter 200 and proximal control element 230 greatly speeds up the time required to retract and re-advance the catheter 200 and/or working devices 500 through the working lumen 410 out the distal lumen 408. The proximal control element 230 of the catheter 200 has a length and structure that extends through the working lumen 410 of the sheath-guide 400 to a proximal end of the system 100 such that the proximal control element 230 can be used to advance and retract the catheter 200 through the working lumen 410. The proximal control element 230 of the catheter 200, however, takes up only a fraction of the luminal space of the system 100 resulting in increased luminal area for aspiration and/or delivery of working devices. The stepped up luminal diameter also increases the annular area available for forward flushing of contrast, saline, or other solutions while devices such as microcatheters or other devices may be coaxially positioned in the luminal portion 222 of the catheter 200 and/or the working lumen 410. This can increase the ease and ability to perform angiograms during device navigation.

In an implementation, the distal luminal portion 222 of the catheter 200 is constructed to be flexible and lubricious, so as to be able to safely navigate to the target location. The distal luminal portion 222 can be kink resistant and collapse resistant when subjected to high aspiration forces so as to be able to effectively aspirate a clot. The luminal portion 222 can have increasing flexibility towards the distal end with smooth material transitions along its length to prevent any kinks, angulations or sharp bends in its structure, for example, during navigation of severe angulations such as those having 90° or greater to 180° turns, for example at the aorto-iliac junction, the left subclavian take-off from the aorta, the takeoff of the brachiocephalic (innominate) artery from the ascending aorta and many other peripheral locations just as in the carotid siphon. For example, a first portion of the distal luminal portion 222 can be formed of a material having a hardness of 72D along a first length, a second portion can be formed of a material having a hardness of 55D along a second length, a third portion can be formed of a material such as Pebax MX1205 (40D) along a third length, a fourth portion can be formed of a material having a hardness of 35D along a fourth length, a fifth portion can be formed of a material having a hardness of 25D along a fifth length, a sixth portion can be formed of a material such as Tecoflex having a hardness of 85A along a sixth length, and a final distal portion of the catheter can be formed of a material such as Tecoflex having a hardness of 80A. Thus, the distal luminal portion 222 transition from being less flexible near its junction with the proximal control element 230 to being more flexible at the distal-most end where, for example, a distal tip of the catheter advancement element 300 can extend from. It should be appreciated that other procedural catheters described herein can have a similar construction providing a variable relative stiffness that transitions from the proximal end towards the distal end of the catheter as will be described elsewhere herein.

In some implementations, the distal luminal portion 222 can transition from being less flexible near its junction with the proximal control element 230 to being more flexible at the distal-most end. The change in flexibility from proximal to distal end of the distal luminal portion 222 can be achieved by any of a variety of methods as described herein. In some implementations, the distal luminal portion 222 has a reinforcement structure that is a nitinol ribbon wrapped into a coil. The coil can be heat-set prior to transferring the coil onto the catheter. The pitch of the coil can increase from proximal end towards distal end of the distal luminal portion 222. For example, the ribbon coils can have gaps in between them and the size of the gaps can increase moving towards the distal end of the distal luminal portion 222. For example, the size of the gap between the ribbon coils can be approximately 0.016" gap near the proximal end of the distal luminal portion 222 and the size of the gap between the ribbon coils near the distal end can be larger such as 0.036" gap. This change in pitch provides for increasing flexibility near the distal-most end of the distal luminal portion 222.

In an implementation, the distal-most end of the distal luminal portion 222 has a flexural stiffness (E*I) in the range of 1500 to 3000 N-mm$^2$ and the remaining portion of the distal luminal portion 222 has a higher flexural stiffness, where E is the elastic modulus and I is the area moment of inertia of the device. These bending stiffness ranges in N-mm$^2$ can be measured by assessing the grams of force generated upon deflecting the device a certain distance using a particular length gauge. For example, using a 3 mm length force gauge and deflecting a tip of the catheter 2 mm, 30-60 grams of force can be generated or can range in bending stiffness between 1500-3000 N-mm$^2$. The flexibility of the distal luminal portion 222 can be based on deflection measurements and the related calculations. As a comparison, the flexibility of the catheter advancement element 300 based on similar deflection measurements and calculations can be as follows. Upon 2 mm deflection and force gauge length of 3 mm, the catheter advancement element 300 can range in gram-force between 1-5 or can range in bending stiffness between 50-200 N-mm$^2$. It should be appreciated that other procedural catheters described herein can have a similar flexibility ranges providing a variable relative stiffness that transitions from the proximal end towards the distal end of the catheter as will be described elsewhere herein.

In some implementations, the distal luminal portion 222 includes two or more layers. In some implementations, the distal luminal portion 222 includes an inner lubricious liner, a reinforcement layer, and an outer jacket layer. The outer jacket layer may be composed of discreet sections of polymer with different durometers, composition, and/or thickness to vary the flexibility along the length of the distal luminal portion 222. In an implementation, the lubricious inner liner is a PTFE liner, with one or more thicknesses along variable sections of flexibility. In an implementation, the reinforcement layer is a generally tubular structure formed of, for example, a wound ribbon or wire coil or braid. The material for the reinforcement structure may be stainless steel, for example 304 stainless steel, nitinol, cobalt chromium alloy, or other metal alloy that provides the desired combination of strengths, flexibility, and resistance to crush. In an implementation, the reinforcement structure includes multiple materials and/or designs, again to vary the flexibility along the length of the distal luminal portion 222. In an implementation, the outer surface of the catheter 200 is coated with a lubricious coating such as a hydrophilic coating. In some implementations the coating may be on an inner surface and/or an outer surface to reduce friction during tracking. The coating may include a variety of materials as is known in the art. The proximal control element 230 may also be coated to improve tracking through the working lumen 410. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

Again with respect to FIGS. 2A-2C, the distal luminal portion 222 of the catheter 200 can have a radiopaque marker 224a at the distal tip region to aid in navigation and proper positioning of the tip under fluoroscopy. Additionally, a proximal region of the catheter 200 may have one or more proximal radiopaque markers 224b so that the overlap region 348 can be visualized as the relationship between a radiopaque marker 411 on the guide sheath 400 and the radiopaque marker 224b on the catheter 200. In an implementation, the two radiopaque markers (marker 224a at distal tip and a more proximal marker 224b) are distinct so as to minimize confusion of the fluoroscopic image, for example the catheter proximal marker 224b may be a single band and the marker 411 on the guide sheath 400 may be a double band and any markers on a working device delivered through the distal access system can have another type of band or mark. The radiopaque markers 224 of the distal luminal portion 222, particularly those near the distal tip region navigating extremely tortuous anatomy, can be relatively flexible such that they do not affect the overall flexibility of the distal luminal portion 222 near the distal tip region. The radiopaque markers 224 can be tungsten-loaded or platinum-loaded markers that are relatively flexible compared to other types of radiopaque markers used in devices where flexibility is not paramount.

As mentioned previously, the control element 230 is configured to allow distal advancement and proximal retraction of the catheter 200 through the working lumen 410 of the guide sheath 400 including passage out the distal lumen 408. In an implementation, the length of the proximal control element 230 is longer than the entire length of the guide sheath 400 (from distal tip to proximal valve), such as by about 5 cm to 15 cm. The length of the body 402 can be in the range of 80 to 90 cm or up to about 100 cm or up to about 105 cm and the length of the proximal control element 230 can be between 90-100 cm.

Again with respect to FIG. 3, the proximal control element 230 can include one or more markers 232 to indicate the overlap between the distal luminal portion 222 of the catheter 200 and the sheath body 402 as well as the overlap between the distal luminal portion 222 of the catheter 200 and other interventional devices that may extend through the distal luminal portion 222. At least a first mark 232 can be an RHV proximity marker positioned so that when the mark 232 is aligned with the sheath proximal hemostasis valve 434 during insertion of the catheter 200 through the guide sheath 400, the catheter 200 is positioned at the distal-most position with the minimal overlap length needed to create the seal between the catheter 200 and the working lumen 410. At least a second mark 232 can be a Fluoro-saver marker that can be positioned on the control element 230 and located a distance away from the distal tip of the distal luminal portion 222. In some implementations, a mark 232 can be positioned about 100 cm away from the distal tip of the distal luminal portion 222.

The proximal control element 230 can include a gripping feature such as a tab 234 on the proximal end to make the proximal control element 230 easy to grasp and advance or retract. The tab 234 can couple with one or more other components of the system as will be described in more detail below. The proximal tab 234 can be designed to be easily identifiable amongst any other devices that may be inserted in the sheath proximal valve 434, such as guidewires or retrievable stent device wires. A portion of the proximal control element 230 and/or tab 234 can be colored a bright color, or marked with a bright color, to make it easily distinguishable from guidewire, retrievable stent tethers, or the like. Where multiple catheters 200 are used together in a nesting fashion to reach more distal locations within the brain, each proximal control element 230 and/or tab 234 can be color-coded or otherwise labeled to clearly show to an operator which proximal control element 230 of which catheter 200 it is coupled to.

The tab 234 can be integrated with or in addition to a proximal hub coupled to a proximal end of the control element 230. For example, as will be described in more detail below, the proximal control element 230 can be a hypotube having a lumen. The lumen of the hypotube can be in fluid communication with the proximal hub at a proximal end of the control element 230 such that aspiration forces and/or fluids can be delivered through the hypotube via the proximal hub.

The proximal control element 230 can be configured with sufficient stiffness to allow advancement and retraction of the distal luminal portion 222 of the catheter 200, yet also be flexible enough to navigate through the cerebral anatomy as needed without kinking. The configuration of the proximal control element 230 can vary. In some implementations, the proximal control element 230 can be a tubular element having an outer diameter that is substantially identical to the outer diameter of the distal luminal portion 222 similar to a typical catheter device. In other implementations, the outer diameter of the proximal control element 230 is sized to avoid taking up too much luminal area in the lumen 410 of the guide sheath 400 as described above.

The proximal control element 230 can be a solid metal wire that is round or oval cross-sectional shape. The proximal control element 230 can be a flattened ribbon of wire having a rectangular cross-sectional shape as shown in FIG. 4A. The flattened ribbon of wire can also have square, rectangular, or other cross-sectional shape. The ribbon of wire can be curved into a circular, oval, c-shape, or quarter circle or other cross-sectional area along an arc. The proximal control element 230 can be a hollow wire having a lumen 235 extending through it, such as a hypotube as shown in FIG. 4B. The hypotube can have an oval or circular shape. In an implementation, the proximal control element 230 is a ribbon of stainless steel having dimensions of about 0.012"×0.020". In an implementation, the proximal control element 230 is a round wire, with dimensions from 0.014" to 0.018". In another implementation, the proximal control element 230 is a ribbon with dimensions ranging from 0.010" to 0.015" thick, and 0.015" thick to 0.025" thick. In an implementation, the proximal control element 230 is a hypotube formed from a flattened ribbon of stiff material rolled into a tubular shape to have a lumen 235. In some implementations, the proximal control element 230 can be formed of a flattened ribbon of stainless steel and rolled into a hypotube such that the proximal control element 230 has a wall thickness of about 0.007", an inner diameter of about 0.004" and an outer diameter of about 0.018" before the hypotube is modified into an oval cross-sectional shape. The ovalized hypotube can maintain an inner diameter that is at least 0.001" along at least a first dimension and an outer diameter that is at least 0.015" along at least a first dimension. In an implementation, the proximal control element 230 material is a metal such as a stainless steel or nitinol as well as a plastic such as any of a variety of polymers.

In an implementation, the proximal control element 230 is a stainless steel hypotube having an oval cross-sectional shape (see FIG. 4B). The oval tubular shape can increase the column strength, pushability and kink resistance of the proximal control element 230 for improved advancement through tortuous anatomy. The cross-sectional area of an oval hypotube minimizes the impact of the catheter 200 on movement of other tools through the working lumen 410 of the sheath 400. FIG. 4C illustrates a cross-sectional view of the working lumen 410 of the sheath 400 having a proximal portion 230 extending therethrough. The proximal portion 230 has a rectangular cross-sectional shape. FIG. 4D illustrates a cross-sectional view of the working lumen 410 having an ovalized hypotube proximal portion 230 and a catheter advancement element 300 extending therethrough. FIG. 4E illustrates the comparison of surface area between the rectangular-shaped ribbon and the oval hypotube. The oval hypotube has less surface area compared to the rectangular-shaped ribbon allowing for a greater flow rate through the working lumen 410, for example, during application of aspirating forces.

Now with respect to FIGS. 5A-5F, the junction between the distal luminal portion 222 of the catheter 200 and the proximal control element 230 can be configured to allow a smooth transition of flexibility between the two portions so as not to create a kink or weak point. The smooth transition at the joint between the distal luminal portion 222 and the proximal control element 230 also allows for smooth passage of devices through the contiguous inner lumen created by the working lumen 410 of the guide sheath 400 and the lumen 223 of the luminal portion 222 of the catheter 200. In an implementation, the distal luminal portion 222 has a transition section 226 near where the luminal portion 222 couples to the proximal control element 230 (see FIG. 5A). The transition section 226 can have an angled cut such that there is no abrupt step transition from the working lumen 410 of the guide sheath 400 to the inner lumen 223 of the catheter 200. The angled cut can be generally planer. In an alternate implementation, the angled cut is curved or stepped to provide a more gradual transition zone. It should be appreciated that the proximal end region of the distal luminal portion 222 can be angled in an oblique manner relative to a longitudinal axis of the catheter 200 such that the proximal end and proximal opening into the lumen are at an angle other than 90° to the longitudinal axis of the catheter 200, for example between approximately 0°, 5°, 10°, 15°, 20°, 25°, 30°, 35°, 40°, or 45° up to less than 90°. The proximal end region of the distal luminal portion 222 can also be aligned substantially perpendicular to the longitudinal axis of the catheter 200 such that the proximal end and proximal opening into the lumen are substantially 90° to the longitudinal axis of the catheter 200. Similarly, the distal end region of the distal luminal portion 222 can be angled in an oblique manner relative to a longitudinal axis of the catheter 200 such that the distal end and distal opening from the lumen 223 are at an angle other than 90° to the longitudinal axis of the catheter 200, for example between approximately 0°, 5°, 10°, 15°, 20°, 25°, 30°, 35°, 40°, or 45° up to less than 90°. The distal end region of the distal luminal portion 222 can also be aligned substantially perpendicular to the longitudinal axis of the catheter 200 such that the distal end and distal opening into the lumen are substantially 90° to the longitudinal axis of the catheter 200.

The proximal control element 230 can be coupled to a proximal end region of the catheter 200 and/or may extend along at least a portion of the distal luminal portion 222 such that the proximal control element 230 couples to the distal luminal portion 222 a distance away from the proximal end. The proximal control element 230 can be coupled to the distal luminal portion 222 by a variety of mechanisms including bonding, welding, gluing, sandwiching, stringing, tethering, or tying one or more components making up the proximal control element 230 and/or portion 222. The distal luminal portion 222 and the proximal control element 230 may be joined by a weld bond, a mechanical bond, an adhesive bond, or some combination thereof. In some implementations, the proximal control element 230 and luminal portion 222 are coupled together by sandwiching the proximal control element 230 between layers of the distal luminal portion 222. For example, the proximal control element 230 can be a hypotube or rod having a distal end that is skived, ground or cut such that the distal end can be laminated or otherwise attached to the layers of the catheter portion 222 near a proximal end region. The region of overlap between the distal end of the proximal control element 230 and the portion 222 can be at least about 1 cm. This type of coupling allows for a smooth and even transition from the proximal control element 230 to the luminal portion 222.

Still with respect to FIGS. 5A-5F, the transition section 226 of the distal luminal portion 222 can open up into a trough 238 extending a length proximal to the transition section 226. In some implementations, the trough 238 has a cross-sectional geometry that is substantially curved. For example, the trough 238 can extend along an arc of the longitudinal axis of the catheter 200 between about 20 to about 90 degrees. In other implementations, the edges of the trough 238 curve such that the trough 238 is not substantially flat. In other implementations, the trough 238 is substantially flat. The trough 238 can provide a smooth transition between distal luminal portion 222 and proximal control element 230 when the device is forced to bend. This can reduce the likelihood of kinking and facilitate pushing against resistance.

The distal end of the proximal control element 230 and/or the distal luminal portion 222 may have features that facilitate a mechanical joint during a weld, such as a textured surface, protruding features, or cut-out features. During a heat weld process, the features would facilitate a mechanical bond between the polymer distal luminal portion 222 and the proximal control element 230. For example, as shown in FIGS. 6A-6F the proximal end of the distal luminal portion 222 can include a short mating sleeve 240 coupled to a proximal edge 221 of the distal luminal portion 222. The sleeve 240 can include an inner lumen extending between a proximal opening 242 and a distal opening 241. The distal end of the proximal control element 230 can insert through the proximal opening 242 and within the inner lumen of the sleeve 240 to couple the proximal control element 230 to the distal luminal portion 222. In some implementations, the proximal control element 230 can couple with the distal luminal portion 222 such that a distal opening 231 of the hypotube forming the proximal control element 230 can communicate with the lumen 223 of the distal luminal portion 222, for example, through the distal opening 241 of the sleeve 240. The sleeve 240 can also provide transition between distal luminal portion 222 and proximal control element 230 similar to the trough 238. The distal luminal portion 222 need not include a mating sleeve 240 to couple with the proximal control element 230. For example, the distal end of the proximal control element 230 can insert through a wall of the trough 238 at the proximal end of the distal luminal portion 222 (see FIG. 5A, 5E-5F). The distal end of the proximal control element 230 can extend along the length of the trough 238 and along at least a length of the wall of the distal luminal portion 222.

Figure 5A:
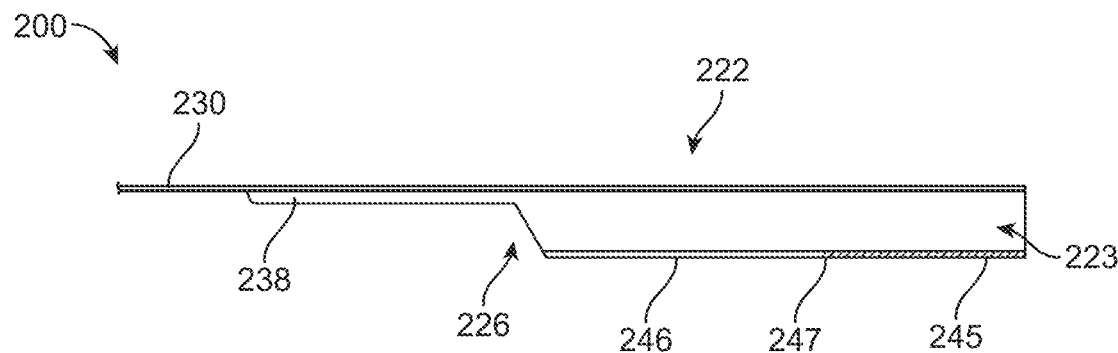
FIG. 5A is a side elevational view of an implementation of a spined distal access catheter.
Figure 5B:
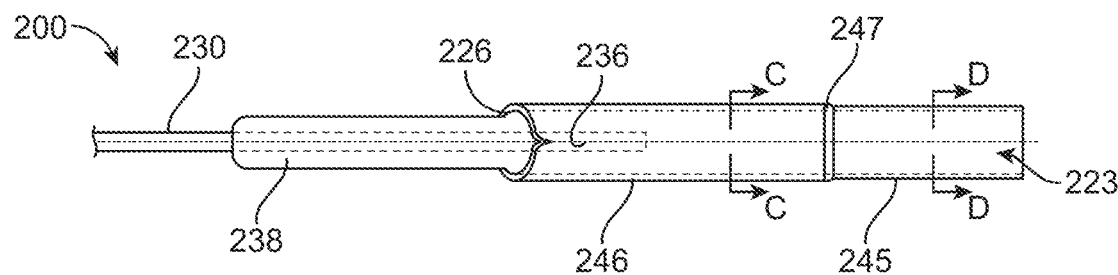
FIG. 5B is a top plan view of the spined distal access catheter of FIG. 5A.
Figure 5C:
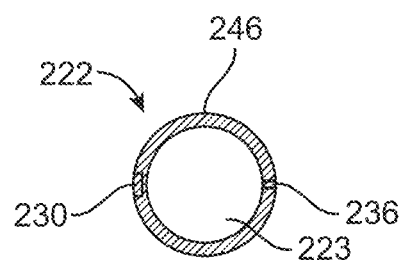
FIG. 5C is a cross-sectional view of the spined distal access catheter taken along line C-C of FIG. 5B.
Figure 5D:
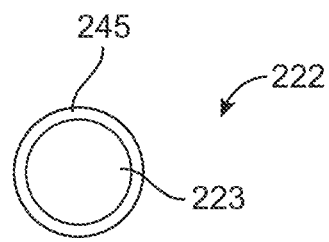
FIG. 5D is a cross-sectional view of the spined distal access catheter taken along line D-D of FIG. 5B.
Figure 5E:
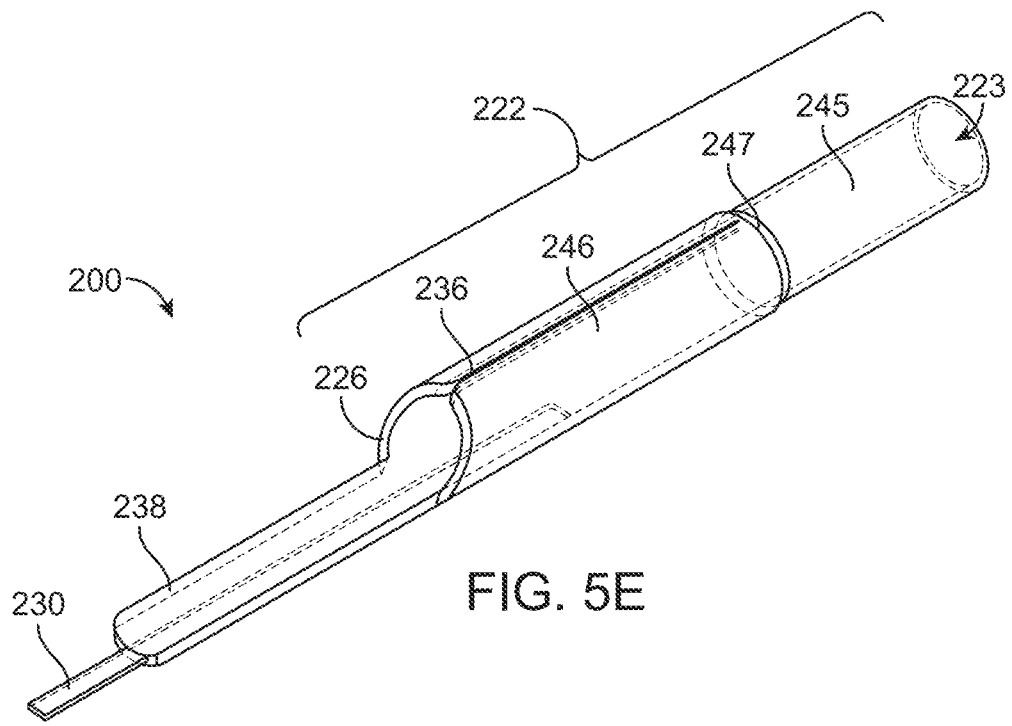
FIGS. 5E-5F are partial perspective views of the spined distal access catheter of FIG. 5A.
Figure 5F:
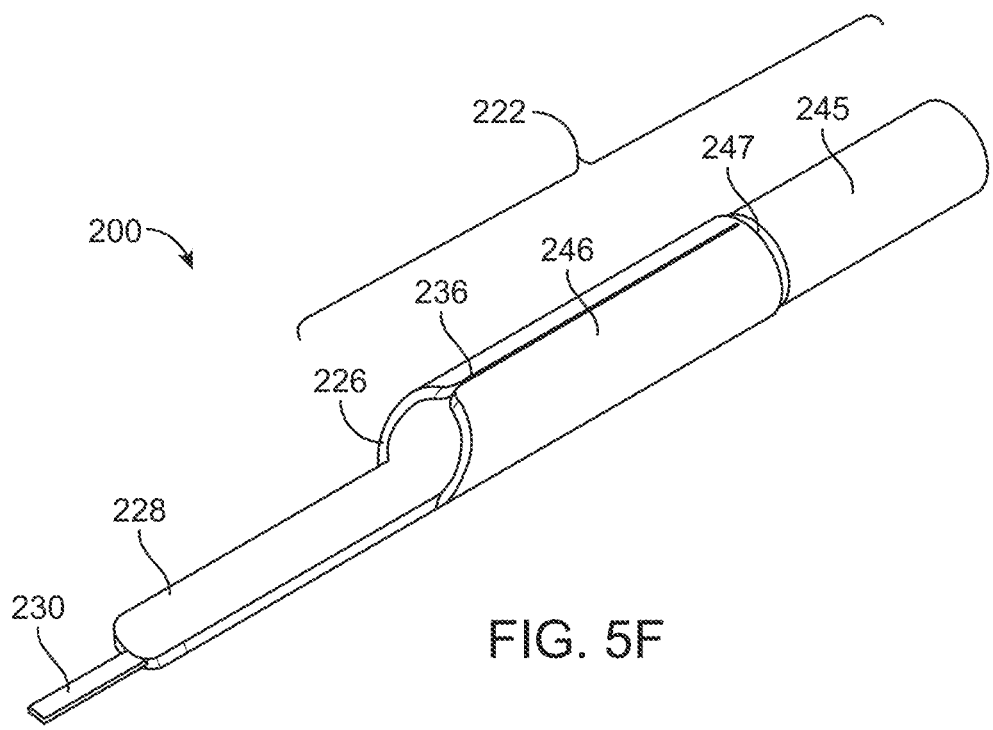
Figure 6A:
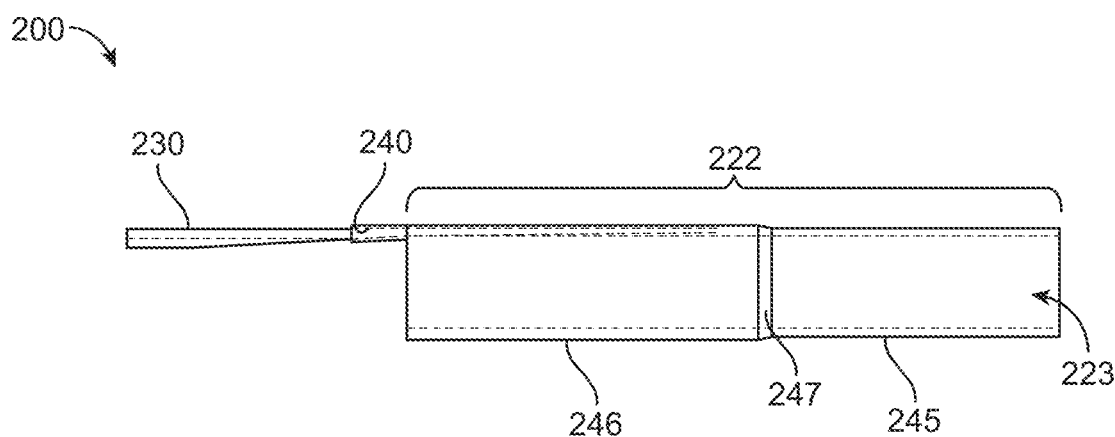
FIG. 6A is a side elevational view of an implementation of a spined distal access catheter.
Figure 6B:
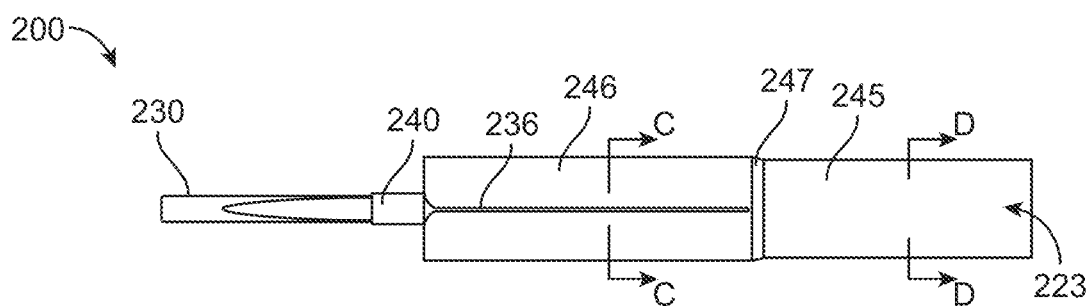
FIG. 6B is a top plan view of the spined distal access catheter of FIG. 6A.
Figure 6C:
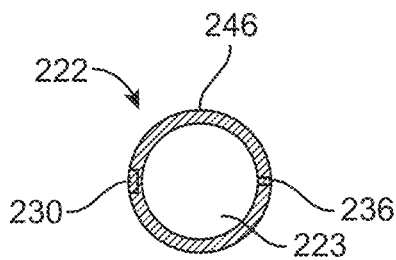
FIG. 6C is a cross-sectional view of the spined distal access catheter taken along line C-C of FIG. 6B.
Figure 6D:
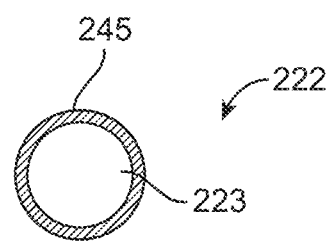
FIG. 6D is a cross-sectional view of the spined distal access catheter taken along line D-D of FIG. 6B.
Figure 6E:
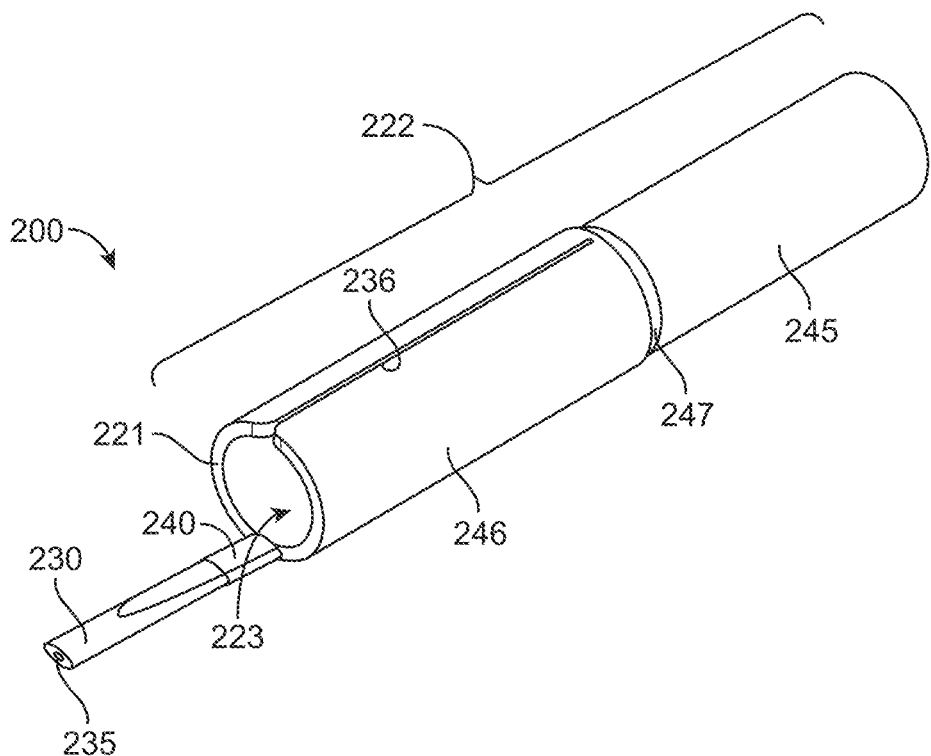
FIGS. 6E-6F are partial perspective views of the spined distal access catheter of FIG. 6A.
Figure 6F:
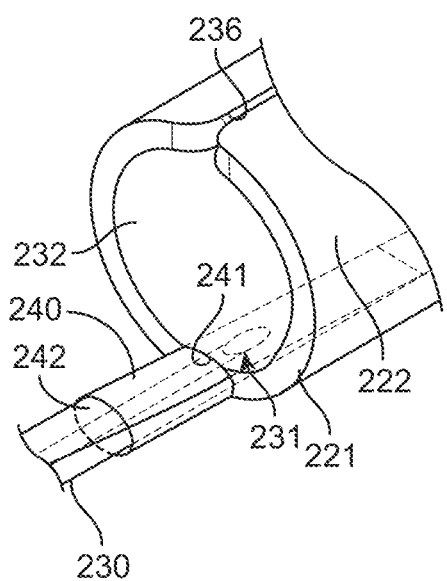

As mentioned above, the luminal portion 222 of the catheter 200 can have a uniform diameter from a proximal end to a distal end or the luminal portion 222 can have different outer diameters along its length. For example, the distal-most end of the distal luminal portion 222 can have a smaller outer diameter compared to a more proximal region of the distal luminal portion 222. FIGS. 5A-5B, 5E-5F as well as FIGS. 6A-6B, 6E-6F show a distal luminal portion 222 having a distal tubular region or distal tube 245 having a smaller outer diameter and a proximal tubular region or proximal tube 246 have a larger outer diameter. The distal tube 245 transitions via a step-up 247 to the proximal tube 246. As best shown in FIGS. 5A and 6A, the inner diameters of distal tube 245 and the proximal tube 246 are substantially the same providing a smooth inner wall surface for the lumen 223. The outer diameter of the distal tube 245 is smaller than the outer diameter of the proximal tube 246. The step-up 247 is formed by a transition in wall thickness between the distal tube 246 and the proximal tube 247. In some implementations, the outer diameter of the distal tube 246 can be about 0.080" to about 0.084" and the outer diameter of the proximal tube 247 can be about 0.087" to about 0.088".

At least a portion of the wall of the larger outer diameter proximal tube 246 can be discontinuous such that it include a slit 236 (see FIGS. 5A-5C, 5E-5F, 6A-6C, and 6E-6F). The slit 236 can extend a distance along the length of the proximal tube 246. The slit 236 can extend from an edge 221 of the proximal tube 246 at least about 2 cm of a length of the proximal tube 247. The slit 236 can, but need not, extend along the entire length of the proximal tube 247 to the location of the step-up 247. Additionally, the proximal tube 247 can include more than one slit 236. The slit 236 can be positioned in the larger diameter proximal tube 246 at a location opposite from where the distal end of the proximal control element 230 couples with the wall of the distal luminal portion 222. As such that distal end of the proximal control element 230 embedded within the wall of the proximal tube 246 lies opposite the slit 236 (see FIGS. 5C and 6C). It should be appreciated that the slit 236 can be positioned around the proximal tube 246 at another location.

The slit 236 can allow for the proximal tube 246 to expand slightly such that the ends of the wall forming the slit 236 separate forming a gap therebetween. For example, upon insertion of the catheter 200 through the working lumen 410 of the sheath 400, the outer diameter can be received in a sliding fit such that at least an overlap region 348 remains. Upon application of an aspirational force through the working lumen 410, for example, by applying suction from an aspiration source coupled to the proximal end 403 of the guide sheath 400, the sealing provided at the overlap region 348 can be enhanced by a slight widening of the gap formed by the slit 236. This slight expansion provides for better sealing between the outer diameter of the proximal tube 246 and the inner diameter of the working lumen 410 of the sheath 400 because the outer surface of the walls of the catheter 200 can press against the inner surface of the working lumen 410 creating a tight fit between the catheter 200 and the sheath 400. This improved sealing between the outer surface of the catheter 200 and the inner surface of the working lumen 410 minimizes the seepage of blood from the vessel into the working lumen 410 directly through the distal opening 408. Thus, the larger outer diameter of the proximal tube 246 in combination with the slit 236 can enhance sealing between the catheter 200 and the sheath 400 by accommodating for variations of sheath inner diameters. The slit 236 can effectively increase the outer diameter of the proximal tube 246 depending on whether the walls forming the slit 236 are separated a distance. The walls forming the slit 236 can separate away from one another and increase a width of slit. The outer diameter of the proximal tube 246 including the increased width upon separation of the walls forming the slit 236 can be the same size or larger than the inner diameter of the sheath through which the proximal tube 246 is inserted. This allows for a single catheter to be compatible with a larger range of inner diameters. In some implementations, the outer diameter of the proximal tube 246 can be 0.081" when the walls forming the slit 236 abut one another and no gap is present. The outer diameter of the proximal tube 246 can increase up to about 0.087" when the walls forming the slit 236 are separated a maximum distance away from one another. Additionally, the increased wall thickness of the proximal tube 246 allows for creating a more robust joint between the distal luminal portion 222 and the proximal control element 230 of the catheter.

Catheter Advancement Element

As mentioned above the distal access system 100 can, but need not, include a catheter advancement element 300 for delivery of the catheter 200 to the distal anatomy. It should be appreciated that where the catheter 200 is described herein as being used together or advanced with the catheter advancement element 300 that the catheter advancement element 200 need not be used to deliver the catheter 200 to a target location. For example, other advancement tools are to be considered herein, such as a microcatheter and/or guidewire as is known in the art. Similarly, the catheter advancement element 300 can be used together to advance other catheters besides the catheter 200 described herein. For example, the catheter advancement element 300 can be used to deliver a 5MAX Reperfusion Catheter (Penumbra, Inc. Alameda, Calif.) for clot removal in patients with acute ischemic stroke or other reperfusion catheters known in the art. Although the catheter advancement element 300 is described herein in reference to catheter 200 it should be appreciated that it can be used to advance other catheters and it is not intended to be limiting to its use.

As described above, the distal access system 100 is capable of providing quick and simple access to distal target anatomy, particularly the tortuous anatomy of the cerebral vasculature. The flexibility and deliverability of the distal access catheter 200 allow the catheter 200 to take the shape of the tortuous anatomy and avoids exerting straightening forces creating new anatomy. The distal access catheter 200 is capable of this even in the presence of the catheter advancement element 300 extending through its lumen. Thus, the flexibility and deliverability of the catheter advancement element 300 is on par or better than the flexibility and deliverability of the distal luminal portion 222 of the distal access catheter 200 in that both are configured to reach the middle cerebral artery (MCA) circulation without straightening out the curves of the anatomy along the way.

The catheter advancement element 300 can include a non-expandable, flexible elongate body 360 coupled to a proximal portion 366. The elongate body 360 can be received within and extended through the internal lumen 223 of the distal luminal portion 222 of the catheter 200 (see FIG. 2B). A distal tip 346 of the catheter advancement element 300 can be extended beyond the distal end of the catheter 200 as shown in FIG. 2B. The proximal portion 366 of the catheter advancement element 300 is coupled to a proximal end region of the elongate body 360 and extends proximally therefrom. The proximal portion 366 can be less flexible than the elongate body 360 and configured for bi-directional movement of the elongate body 360 of the catheter advancement element 300 within the luminal portion 222 of the catheter 200, as well as for movement of the catheter system 100 as a whole. The elongate body 360 can be inserted in a coaxial fashion through the internal lumen 223 of the luminal portion 222. The outer diameter of at least a region of the elongate body 360 can be sized to substantially fill the internal lumen 223 of the luminal portion 222.

The overall length of the catheter advancement element 300 (e.g. between the proximal end through to the distal-most tip) can vary, but generally is long enough to extend through the support catheter 200 plus at least a distance beyond the distal end of the support catheter 200 while at least a length of the proximal portion 366 remains outside the proximal end of the guide sheath 400. In some implementations, the overall length of the catheter advancement element 300 is about 149 cm and a working length of 143 cm from a proximal tab or hub to the distal-most tip. The elongate body 360 can have a length that is at least as long as the luminal portion 222 of the catheter 200 although it should be appreciated the elongate body 360 can be shorter than the luminal portion 222 so long as at least a length remains inside the luminal portion 222 when a distal portion of the elongate body 360 is extended distal to the distal end of the luminal portion 222. In some implementations, the shaft length of the distal luminal portion 222 can be about 39 cm and the insert length of the elongate body 360 can be at least about 48.5 cm, 49 cm, or about 49.5 cm. The proximal portion 366 can have a length that varies as well. In some implementations, the proximal portion 366 is about 94 cm. The distal portion extending distal to the distal end of the luminal portion 222 can include distal tip 346 that protrudes a length beyond the distal end of the luminal portion 222 during use of the catheter advancement element 300. The distal tip 346 of the elongate body 360 that is configured to protrude distally from the distal end of the luminal portion 222 aids in the navigation of the catheter system through the tortuous anatomy of the cerebral vessels, as will be described in more detail below. The proximal portion 366 coupled to and extending proximally from the elongate body 360 can align generally side-by-side with the proximal control element 230 of the catheter 200. The arrangement between the elongate body 360 and the luminal portion 222 can be maintained during advancement of the catheter 200 through the tortuous anatomy to reach the target location for treatment in the distal vessels and aids in preventing the distal end of the catheter 200 from catching on tortuous branching vessels, as will be described in more detail below.

In some implementations, the elongate body 360 can have a region of relatively uniform outer diameter extending along at least a portion of its length and the distal tip 346 tapers down from the uniform outer diameter. When the catheter advancement element 300 is inserted through the catheter 200, this tapered distal tip 346 is configured to extend beyond and protrude out through the distal end of the luminal portion 222 whereas the more proximal region of the body 360 having a uniform diameter remains within the luminal portion 222. As mentioned, the distal end of the luminal portion 222 can be blunt and have no change in the dimension of the outer diameter whereas the distal tip 346 can be tapered providing an overall elongated tapered geometry of the catheter system. The outer diameter of the elongate body 360 also approaches the inner diameter of the luminal portion 222 such that the step-up from the elongate body 360 to the outer diameter of the luminal portion 222 is minimized. Minimizing this step-up prevents issues with the lip formed by the distal end of the luminal portion 222 catching on the tortuous neurovasculature, such as around the carotid siphon near the ophthalmic artery branch, when the distal tip 346 bends and curves along within the vascular anatomy. In some implementations, the inner diameter of the luminal portion 222 can be 0.072" and the outer diameter of the elongate body 360 is 0.070" such that the difference between them is only 2 thousandths of an inch. In other implementations, the outer diameter of the elongate body 360 is 0.062". Despite this, the luminal portion 222 and the elongate body 360 extending through it in co-axial fashion are flexible enough to navigate the tortuous anatomy leading to the level of M1 or M2 arteries without kinking and without damaging the vessel.

The length of the distal tip 346 can vary. In some implementations, the length of the distal tip 346 can be in a range of between about 0.50 cm to about 3.0 cm from the distal-most terminus of the elongate body 360. In other implementations, the length of the distal tip 346 is between 2.0 cm to about 2.5 cm. In some implementations, the length of the distal tip 236 varies depending on the inner diameter of the elongate body 360. For example, the length of the distal tip 236 can be as short as 0.5 cm and the inner diameter can be 0.054". The distal tip 346 can be a constant taper from the outer diameter of the elongate body 360 down to a second smaller outer diameter at the distal-most tip. The constant taper of the distal tip 346 can be from 0.062" outer diameter to about 0.031" outer diameter. The length of the constant taper of the distal tip 346 can vary, for example, between 1 cm and 3 cm, or between 2.0 cm and 2.5 cm.

It should be appreciated that the distal tip 346 need not taper and can achieve its soft, atraumatic and flexible characteristic due to a material property other than due to a change in outer dimension to facilitate endovascular navigation to an embolus in tortuous anatomy. Additionally or alternatively, the distal tip 346 of the elongate body 360 can have a transition in flexibility along its length. The most flexible region of the distal tip 346 can be its distal terminus. Moving along the length of the distal tip 346 from the distal terminus towards a region proximal to the distal terminus, the flexibility can gradually approach the flexibility of the distal end of the luminal portion 222. For example, the distal tip 346 can be formed of a material having a hardness of 35D and transitions proximally towards increasingly harder materials having a hardness of 55D and 72D up to the proximal portion 366, which can be a stainless steel hypotube, or a combination of a material property and tapered shape. The materials used to form the regions of the elongate body 360 can include Pebax (such as Pebax 25D, 35D, 55D, 72D) with a lubricious additive compound. Incorporation of a lubricious additive directly into the polymer elongate body means incorporation of a separate lubricious liner, such as a Teflon liner, is unnecessary. This allows for a more flexible element that can navigate the distal cerebral anatomy and is less likely to kink. Similar materials can be used for forming the distal luminal portion 222 of the catheter 200 providing similar advantages. It should also be appreciated that the flexibility of the distal tip 346 can be achieved by a combination of flexible lubricious materials and tapered shapes. For example, the length of the tip 346 can be kept shorter than 2 cm-3 cm, but maintain optimum deliverability due to a change in flexible material from distal-most tip towards a more proximal region a distance away from the distal-most tip. In an implementation, the elongate body 360 is formed of PEBAX (polyether block amide) embedded silicone designed to maintain the highest degree of flexibility. It should be appreciated that the wall thickness of the distal end of the luminal portion 222 can also be made thin enough such that the lip formed by the distal end of the luminal portion 222 relative to the elongate body 360 is minimized.

As mentioned above, the elongate body 360 can be constructed to have variable stiffness between the distal and proximal ends of the elongate body 360. The flexibility of the elongate body 360 is highest at the distal-most terminus of the distal tip 346 and can gradually transition in flexibility to approach the flexibility of the distal end of the luminal portion 222, which is typically less flexible than the distal-most terminus of the distal tip 346. Upon inserting the catheter advancement element 300 through the catheter 200, the region of the elongate body 360 extending beyond the distal end of the luminal portion 222 can be the most flexible and the region of the elongate body 360 configured to be aligned with the distal end of the luminal portion 222 during advancement in the vessel can have a substantially identical flexibility as the distal end of the luminal portion 222 itself. As such, the flexibility of the distal end of the luminal portion 222 and the flexibility of the body 360 just proximal to the extended portion (whether tapered or having no taper) can be substantially the same. This provides a smooth transition in material properties to improve tracking of the catheter system through tortuous anatomy. Further, the more proximal sections of the elongate body 360 can be even less flexible and increasingly stiffer. It should be appreciated that the change in flexibility of the elongate body 360 can be a function of a material difference, a dimensional change such as through tapering, or a combination of the two. The elongate body 360 has a benefit over a microcatheter in that it can have a relatively large outer diameter that is just 0.003"-0.010" smaller than the inner diameter of the catheter 200 and still maintain a high degree of flexibility for navigating tortuous anatomy.

The elongate body 360 can be formed of various materials that provide a suitable flexibility and lubricity. Example materials include high density polyethylene, 72D PEBAX, 90D PEBAX, or equivalent stiffness and lubricity material. The flexibility of the elongate body 360 can increase towards the distal tip such that the distal region of the elongate body 360 is softer, more flexible, and articulates and bends more easily than a more proximal region. For example, a more proximal region of the elongate body can have a bending stiffness that is flexible enough to navigate tortuous anatomy such as the carotid siphon without kinking.

Figure 7D:
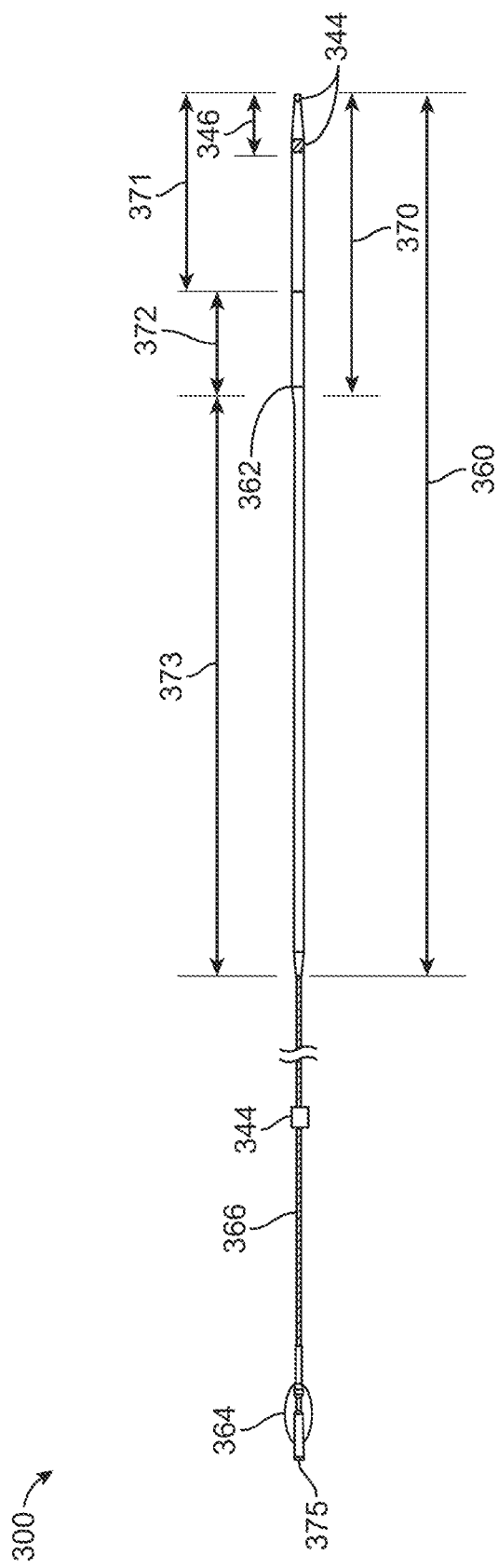
FIG. 7D is a side view of another implementation of a catheter advancement element.

In some implementations, the elongate body 360 can be generally tubular along at least a portion of its length such that it has a lumen 368 extending parallel to a longitudinal axis of the catheter advancement element 300 (see FIG. 7A-7C). In an implementation, the lumen 368 of the elongate body 360 is sized to accommodate a guidewire, however it should be appreciated that use of the catheter advancement element 300 generally eliminates the need for a guidewire lead. The guidewire can extend through the lumen 368 from a proximal opening to a distal opening through which the guidewire can extend. In some implementations, the proximal opening is at the proximal end of the catheter advancement element 300 such that the catheter advancement element 300 is configured for over-the-wire (OTW) methodologies. In other implementations, the proximal opening is a rapid exchange opening 362 such that the catheter advancement element 300 is configured for rapid exchange rather than or in addition to OTW. In this implementation, the proximal opening 362 is located a distance away from a proximal tab 364 and distal to the proximal portion 366 (see FIGS. 7A-7B and 7D). The lumen 368 of the elongate body 360 can be configured to receive a guidewire in the range of 0.014" and 0.018" diameter, or in the range of between 0.014" and 0.022". In this implementation, the inner luminal diameter of the elongate body 360 can be between 0.020" and 0.024". The guidewire, catheter advancement element 300, and the catheter 200 can all be assembled co-axially for insertion through the working lumen 410 of the guide sheath 400. The inner diameter of the lumen 368 of the elongate body 360 can be 0.019" to about 0.021".

FIG. 7D shows another implementation of the catheter advancement element 300 configured for rapid exchange. Rapid exchange configurations can dramatically shorten device length, decreases staffing requirements, and reduces fluoroscopy. As with other implementations described herein, the catheter advancement element 300 can include a non-expandable, flexible elongate body 360 coupled to a proximal portion 366 coupled to a proximal tab 364 or hub 375. As described elsewhere herein, the region near the distal tip 346 can be tapered such that the outer diameter tapers over a length of between 1 cm to about 3 cm. In some implementations, the distal taper length is 2.5 cm. In some implementations, the distal tip 346 tapers from about 0.080" to about 0.031". Also as described elsewhere herein, the distal tip 346 can be formed of a material having a hardness of 35D and transitions proximally towards increasingly harder materials having a hardness of 55D and 72D up to the proximal portion 366. For example, FIG. 7D illustrates segment 371 of the elongate body 360 including the distal tip 346 can have a hardness of 35D and a length of about 10 cm. Segment 372 of the elongate body 360 can have a hardness of 55D and have a length of about 8 cm. Segment 373 of the elongate body 360 can have a hardness of 72D can be about 31 cm in length. The three segments 371, 372, 373 combined can form an insert length of the elongate body 360 from where the proximal portion 366 couples to the elongate body 360 to the terminus of the distal tip 346 that can be about 49 cm in length.

Still with respect to FIG. 7D, an entry port 362 for a procedural guidewire 805 can be positioned a distance away from the distal-most end of the elongate body 360. In some implementations, the entry/exit port 362 can be about 18 cm from the distal-most end creating a rapid exchange wire entry/exit segment 370. The outer diameter of the elongate body 360 within segment 370 (segments 371 and 372) can be about 0.080"-0.082" whereas segment 373 proximal to this rapid exchange wire entry/exit segment 370 can have a step-down in outer diameter such as about 0.062"-0.064".

Figure 7E:
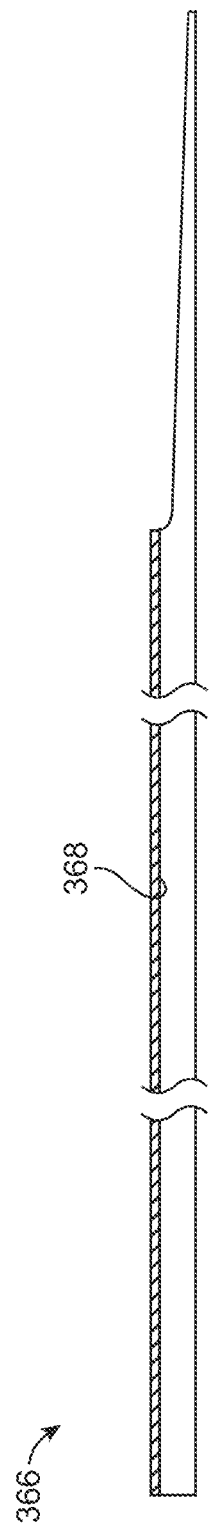
FIG. 7E is cross-sectional view of an implementation of a proximal portion the catheter advancement element of FIG. 7D.

In other implementations, the entire catheter advancement element 300 can be a tubular element configured to receive a guidewire through both the proximal portion 366 as well as the elongate body 360. For example, the proximal portion 366 can be a hypotube or tubular element having a lumen that communicates with the lumen 368 extending through the elongate body 360 (shown in FIG. 3). In some implementations, the proximal portion 366 can be a skived hypotube of stainless steel coated with PTFE having an outer diameter of 0.026". In other implementations, the outer diameter can be between 0.024" and 0.030". In some implementations, such as an over-the-wire version, the proximal portion 366 can be a skived hypotube coupled to a proximal hub 375. The proximal portion 366 can extend eccentric or concentric to the distal luminal portion 222. As best shown in FIG. 7E, the proximal portion 366 can be a stainless steel hypotube as described elsewhere herein. The hypotube can have a lubricious coating such as PTFE. The hypotube can have an inner diameter of about 0.021", an outer diameter of about 0.0275", and an overall length of about 94 cm providing a working length for the catheter advancement element 300 that is about 143 cm. Including the proximal hub 375, the catheter advancement element 300 can have an overall length of about 149 cm. In some implementations, the hypotube can be a tapered part with a length of about 100 mm, starting proximal with a thickness of 0.3 mm and ending with a thickness of 0.10 mm to 0.15 mm. In still further implementations, the elongate body 360 can be a solid element coupled to the proximal portion 366 having no guidewire lumen.

As best shown in FIGS. 7F-7J, the proximal end of the hypotube can be coupled to a proximal hub 375. The proximal hub 375 can be an over-molded component having a luer thread 377 and a luer taper 378 formed on an inside of the proximal hub 375. The proximal hub 375 can incorporate a tab 364 providing for easier gripping by a user. The proximal hub 375 prevents advancement of the catheter advancement element 300 and the catheter 200 beyond the distal tip of the base sheath 400 or guide catheter by limiting insertion into the proximal RHV 434 providing critical functional and safety features for proper operation of the system 10.

At least a portion of the solid elongate body 360, such as the elongate distal tip 346, can be formed of or embedded with or attached to a malleable material that skives down to a smaller dimension at a distal end. The distal tip 346 can be shaped to a desired angle or shape similar to how a guidewire may be used. The malleable length of the elongate body 360 can be at least about 1 cm, 3 cm, 5 cm, and up to about 10 cm, 15 cm, or longer. In some implementations, the malleable length can be about 1%, 2%, 5%, 10%, 20%, 25%, 50% or more of the total length of the elongate body 360. In some implementations, the catheter advancement element 300 can have a working length of about 140 cm to about 143 cm and the elongate body 360 can have an insert length of about 49 cm. The insert length can be the PEBAX portion of the elongate body 360 that is about 49.5 cm. As such that malleable length of the elongate body 360 can be between about 0.5 cm to about 25 cm or more. The shape change can be a function of a user manually shaping the malleable length prior to insertion. Alternatively, the shape change can be a reversible and actuatable shape change such that the tip forms the shape upon activation by a user such that the tip can be used in a straight format until a shape change is desired by the user.

It should be appreciated that the elongate body 360 can extend along the entire length of the catheter 200, including the distal luminal portion 222 and the proximal control element 230 or the elongate body 360 can incorporate the proximal portion 366 that aligns generally side-by-side with the proximal control element 230 of the catheter 200, as described above. The proximal portion 366 of the elongate body 360 can be positioned co-axial with or eccentric to the elongate body 360. The proximal portion 366 of the elongate body 360 can have a lumen extending through it. Alternatively, the portion 366 can be a solid rod or ribbon having no lumen.

Again with respect to FIGS. 7*a*-7D, like the distal luminal portion 222 of the catheter 200, the elongate body 360 can have one or more radiopaque markers 344 along its length. The one or more markers 344 can vary in size, shape, and location. One or more markers 344 can be incorporated along one or more parts of the catheter advancement element 300, such as a tip-to-tip marker, a tip-to-taper marker, an RHV proximity marker, a Fluoro-saver marker, or other markers providing various information regarding the relative position of the catheter advancement element 300 and its components. In some implementations and as best shown in FIG. 7C, a distal end region can have a first radiopaque marker 344*a* and a second radiopaque marker 344*b* can be located to indicate the border between the tapering of the distal tip 346 and the more proximal region of the elongate body 360 having a uniform or maximum outer diameter. This provides a user with information regarding an optimal extension of the distal tip 346 relative to the distal end of the luminal portion 222 to minimize the lip at this distal end of the luminal portion 222 for advancement through tortuous anatomy. In other implementations, for example where the distal tip 346 is not necessarily tapered, but instead has a change in overall flexibility along its length, the second radiopaque marker 344*b* can be located to indicate the region where the relative flexibilities of the elongate body 360 (or the distal tip 346 of the elongate body 360) and the distal end of the luminal portion 222 are substantially the same. The marker material may be a platinum/iridium band, a tungsten, platinum, or tantalum-impregnated polymer, or other radiopaque marker that does not impact the flexibility of the distal tip 346 and elongate body 360. In some implementations, the radiopaque markers are extruded Pebax loaded with tungsten for radiopacity. In some implementations, the proximal marker band can be about 2.0 mm wide and the distal marker band can be about 2.5 mm wide to provide discernable information about the distal tip 346.

As mentioned above, the proximal control element 230 of the catheter 200 can include a proximal tab 234 on the proximal end of the proximal control element 230. Similarly, the proximal portion 366 coupled to the elongate body 360 can include a tab 364. The tabs 234, 364 can be configured to removably and adjustable connect to one another and/or connect to their corresponding proximal portions. The coupling allows the catheter advancement element 300 to reversibly couple with the catheter 200 to lock (and unlock) the relative extension of the distal luminal portion 222 and the elongate body 360. This allows the catheter 200 and the catheter advancement element 300 to be advanced as a single unit. In the locked configuration, the tab 364 or proximal portion 366 can be engaged with the catheter tab 234. In the unlocked configuration, the tab 364 may be disengaged from the catheter tab 234. The tab 364 or proximal portion 366 may attach, e.g., click or lock into, the catheter tab 234 in a fashion as to maintain the relationships of corresponding section of the elongate body 360 and the catheter 200 in the locked configuration. It should be appreciated that the tab 364 can be a feature on the proximal hub 375 such as the hub 375 shown in FIGS. 7F-7J.

Such locking may be achieved by, e.g., using a detent on the tab 364 that snaps into place within a recess formed in the catheter tab 234, or vice versa. For example, the tab 234 of the catheter 200 can form a ring having a central opening extending therethrough. The tab 364 of the body 360 can have an annular detent with a central post sized to insert through the central opening of the tab 234 such that such that the ring of the tab 234 is received within the annular detent of tab 364 forming a singular grasping element for a user to advance and/or withdraw the catheter system through the access sheath. The tabs 234, 364 may be affixed or may be slideable to accommodate different relative positions between the elongate body 360 and the luminal portion 222 of the catheter 200. In some implementations, a proximal end of the proximal control element 230 of the catheter 200 can include a coupling feature 334, such as clip, clamp, c-shaped element or other connector configured to receive the proximal portion 366 of the catheter advancement element 300 (see FIG. 2A). The coupling feature 334 can be configured to snap together with the proximal portion 366 through an interference fit such that a first level of force is needed in order to insert the proximal portion 366 into the clip of the tab 234 and a second, greater level of force is needed to remove the proximal portion 366 from the clip of the tab 234. However, upon inserting the proximal portion 366 into the coupling feature 334 the catheter advancement element 300 and the catheter 200 can still be slideably adjusted relative to one another along a longitudinal axis of the system. The amount of force needed to slideably adjust the relative position of the two components can be such that inadvertent adjustment is avoided and the relative position can be maintained during use, but can be adjusted upon conscious modification. It should be appreciated that the configuration of the coupling between the proximal portion 366 of the catheter advancement element 300 and the proximal extension 360 of the catheter 200 can vary. Generally, however, the coupling is configured to be reversible and adjustable while still providing adequate holding power between the two elements in a manner that is relatively user-friendly (e.g. allows for one-handed use) and organizes the proximal ends of the components (e.g. prevents the proximal extension 360 and proximal portion 366 from becoming twisted and entangled with one another). It should also be appreciated that the coupling feature 334 configured to prevent entanglement and aid in the organization of the proximal portions can be integrated with the tabs or can be a separate feature located along their proximal end region.

The catheter advancement element 300 can be placed in a locked configuration with the catheter 200 configured for improved tracking through a tortuous and often diseased vasculature in acute ischemic stroke. Other configurations are considered herein. For example, the elongate body 360 can include one or more detents on an outer surface. The detents can be located near a proximal end region and/or a distal end region of the elongate body 360. The detents are configured to lock with correspondingly-shaped surface features on the inner surface of the luminal portion 222 through which the elongate body 360 extends. The catheter advancement element 300 and the catheter 200 can have incorporate more than a single point of locking connection between them. For example, a coupling feature 334, such as clip, clamp, c-shaped element or other connector configured to hold together the catheter advancement element 300 and proximal control element 230 or tab 234 of the catheter 200 as described elsewhere herein.

In some implementations, the proximal control element 230 of the catheter 200 can run alongside or within a specialized channel of the proximal portion 366. The channel can be located along a length of the proximal portion 366 and have a cross-sectional shape that matches a cross-sectional shape of the catheter proximal control element 230 such that the proximal control element 230 of the catheter 200 can be received within the channel and slide smoothly along the channel bi-directionally. Once the catheter 200 and elongate body 360 are fixed, the combined system, i.e., the catheter 200-catheter advancement element 300 may be delivered to a target site, for example through the working lumen 410 of the guide sheath 400 described elsewhere herein.

Intracranial Delivery System

Described herein are intracranial delivery systems that allow for the delivery of stent retriever, intracranial stent, flow diverter or other microcatheter-delivered device through a conduit created by the support catheter 200 extending distally from the guide sheath 400. In some implementations, the intracranial delivery system (IDS) is a rapid exchange system that allows for a single operator to perform all steps in the distal access and device delivery. As will be described in more detail below, the intracranial delivery system allows for "pushing" of the interventional device through only a short length (e.g. 10-20 cm) of the microcatheter lumen as opposed to up an entire microcatheter lumen.

Figure 8A:
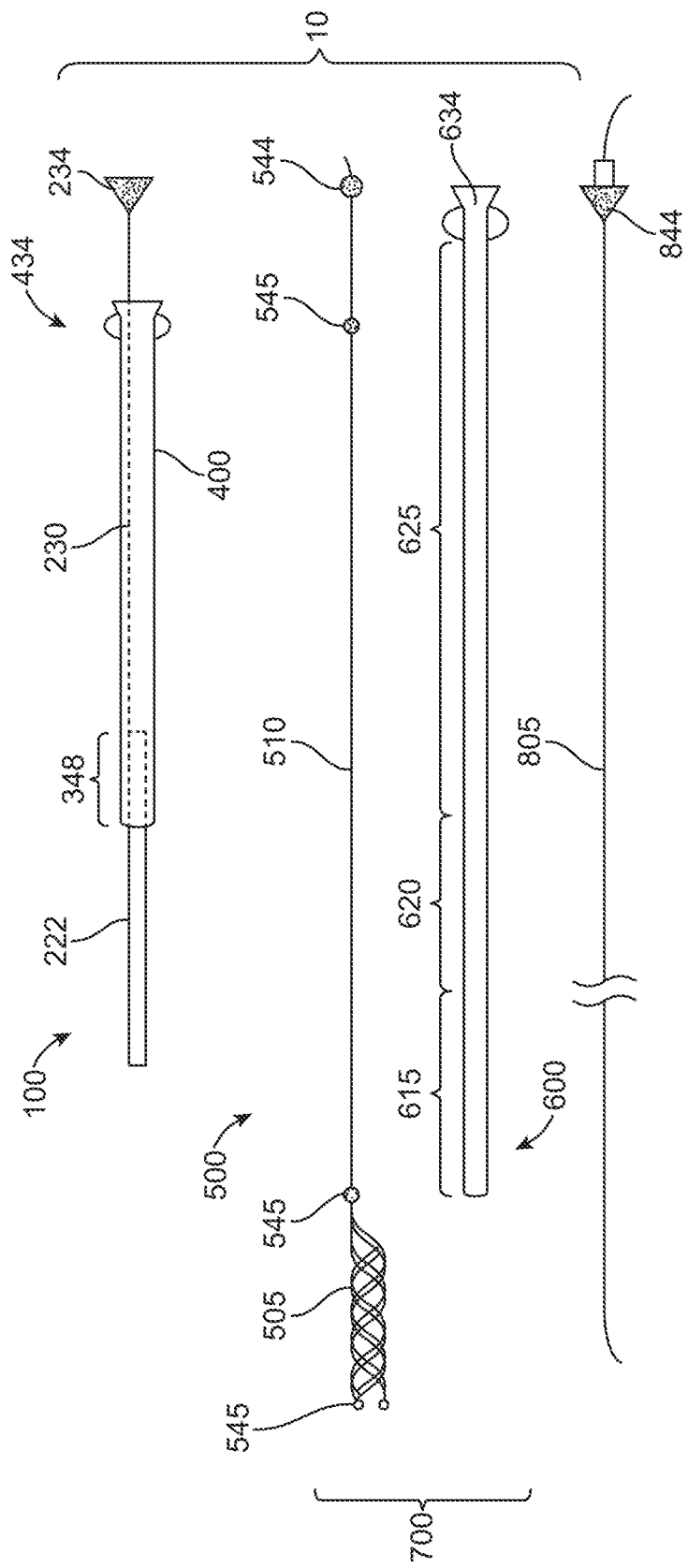
FIGS. 8A-8C illustrate various implementations of single operator working device delivery systems configured to be delivered through a distal access system.
Figure 8B:
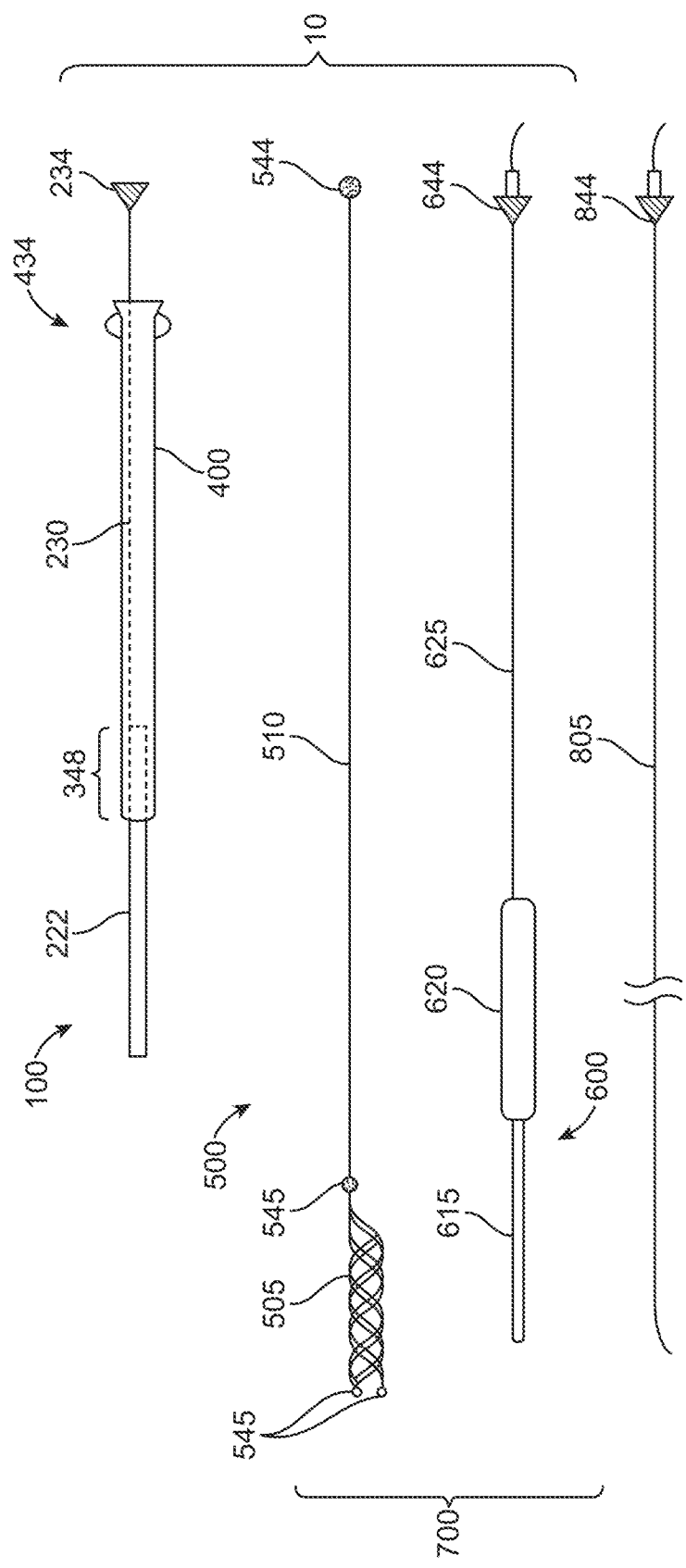
Figure 8C:
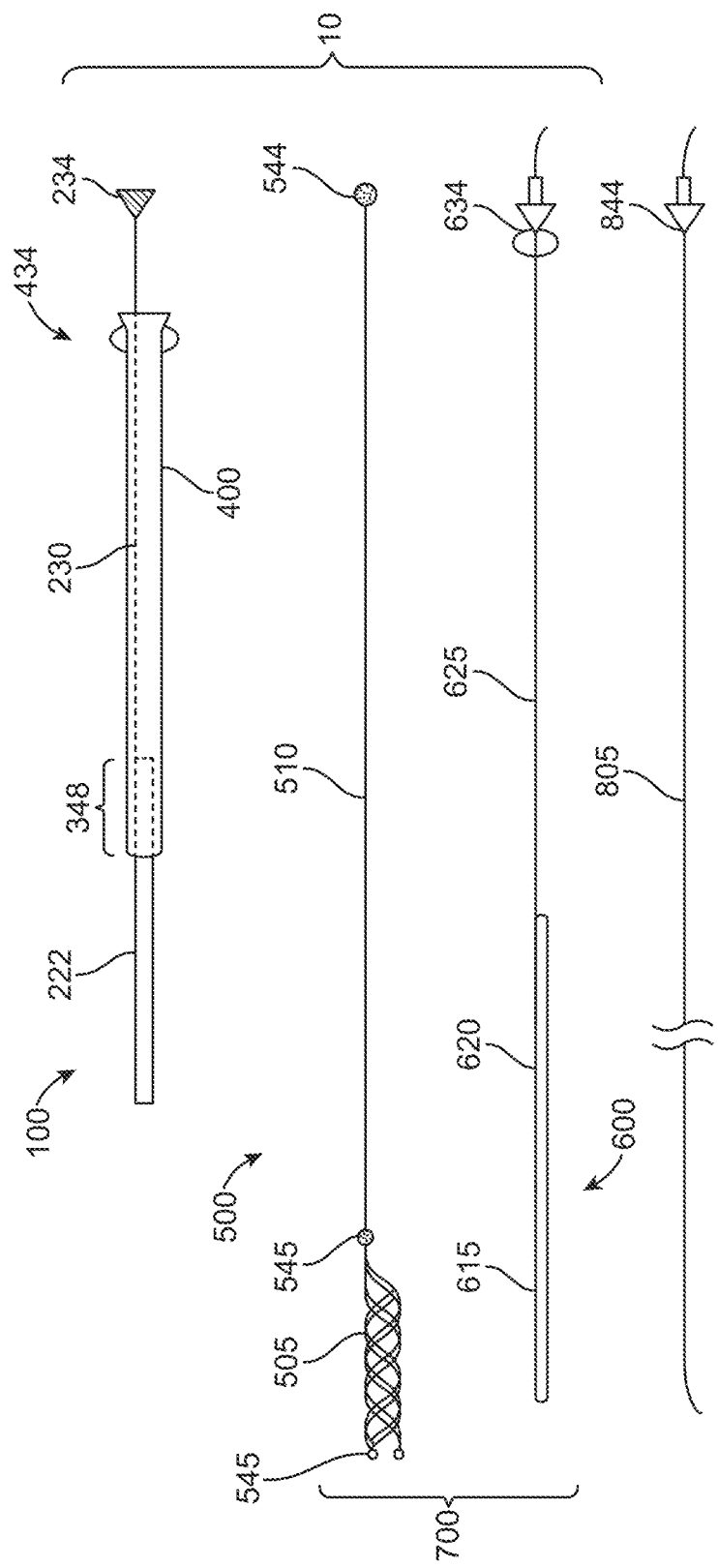

FIGS. 8A-8C illustrate various systems 10 including a single operator intracranial working device delivery system 700 configured to be delivered through a support catheter 200 of a distal access system 100 for accessing and removing a cerebral occlusion to treat acute ischemic stroke. The intracranial delivery system 700 can include a working device 500 for treatment of the cerebral occlusion and configured to be housed within a microcatheter 600. The intracranial delivery system 700 can optionally include a procedural guidewire 805 for delivery of the support catheter 200 extending through the guide sheath 400 of the distal access system 100 as well as for delivery of the microcatheter 600 pre-loaded with a working device 500.

The working device 500 can be a stent retriever (e.g. Solitaire by Medtronic or Trevo by Stryker), stent (e.g. self-expanding or balloon expandable), flow diverter, and other devices known in the art. The working device 500 can include a distal, expandable payload 505 coupled to a proximal control element 510 or push wire coupled to a proximal end of the expandable payload 505. The payload 505 can be collapsed and housed within a portion of the microcatheter 600 as will be described in more detail below. The proximal control element 230 of the catheter 200 and the proximal control element 510 of the working device 500 can extend outside the proximal end of the guide sheath 400 such that they can be used to control the interrelationship of the microcatheter 600 housing the working device 500 with the catheter 200. In some implementations, the proximal control element 510 of the working device 500 can be removable such as when the working device 500 is a stent or other type of interventional device intended to be left in place within the vasculature. The proximal control element 510 can be a spine, push wire, push tube, or other element having any of a variety of configuration that allows for the control element 510 to be used for bi-directional movement of the working device 500 relative to the other components of the IDS 700 and/or the distal access system 100, for example to advance and position an expandable payload 505 relative to the lumen 605 of the microcatheter 600. The proximal control element 510 can be a tubular element that is hollow or can be a solid wire, rod, ribbon or other type of structure. The working device 500 can include one or more markers 545 along its length. In some implementations, the working device 500 includes one or more radiopaque markers 545 positioned near the payload 505, such as at the distal tip, middle regions, and/or just proximal to the expandable payload 505. The working device 500 can also include one or more markers 545 on a region of the proximal control element 510 that are readily visible to an operator outside the RHV 434 that show the position of the payload 505 relative to the microcatheter 600, the guidewire 805, and/or the support catheter 200 without the need for fluoroscopy.

Again with respect to FIG. 8A-8C, the intracranial delivery system 700 also includes a microcatheter 600. The microcatheter 600 is designed such that at least a portion of its length (i.e. the portion extending beyond the distal catheter 200) can navigate independently through the neurovasculature (e.g. the bony petrous portion of the carotid and the carotid siphon) into the anterior circulation of the cerebral vascular anatomy. For example, by incorporating sufficient structural reinforcement without kinking or collapsing during delivery. The microcatheter 600 can have a single lumen configured for rapid exchange delivery.

In some implementations, the microcatheter 600 can have a distal microcatheter portion 615, a payload portion 620 located proximal to the distal portion 615, and a proximal control element 625. As will be described in more detail below, each of these portions of the microcatheter 600 can be designed to have different flexibilities depending on whether the portion will extend outside the distal access system (e.g. the distal portion 615) or remain inside the conduit provided by the distal access system (e.g. the proximal control element 625).

The distal microcatheter portion 615 is designed to be very flexible and deliverable such that it can be extended beyond the distal end of the support catheter 200 and be used to independently navigate the distal tortuosity. For example, the distal portion 615 can be used to navigate the cervical loop portion such as from the petrous carotid to the Circle of Willis with minimal straightening force. The distal portion 615 is designed to be the only portion of the microcatheter 600 that exits the distal access catheter 200 and interacts directly with the cerebrovascular anatomy while the stiffer portions such as the proximal control element 625 of the microcatheter 600 remains within the distal access catheter 200.

The length of the distal portion 615 can vary, but is generally between 10 cm-20 cm long. In some implementations, the distal portion 615 is between 12 cm up to about 15 cm. In some implementations, the distal portion 615 is between 15 cm-18 cm long. In other implementations, the distal portion 615 is at least 18 cm long. This length allows the distal portion 615, which is the most flexible region of the microcatheter 600, to reach the M2 level when, for example, the support catheter 200 is advanced only to the level of the petrous carotid while the remainder of the microcatheter 600, including the stiffer intermediate portion extending between 15 cm-30 cm proximal to the distal portion 615, is shielded by the conduit provided by the distal access system 100 (e.g. within the cervical carotid). Thus, the less deliverable part of the microcatheter 600 remains sheathed and is prevented from causing straightening forces to the tortuous anatomy as described elsewhere herein.

The distal, more flexible region can be about 18 cm in length whereas the stiffer portion can be between 15-30 cm in length. The proximal control element 625 can be much longer such as between 90 cm-115 cm in length. Generally, the length of the microcatheter 600 as well as the working device 500 are relatively short compared to conventional stent retriever systems. The length of the proximal control element 625 can be maintained such that the proximal control element 625 combined with the intermediate stiffness portion of the microcatheter 600 are no longer than the overall length of the spined distal catheter 200. This relative length ensures the only portion of the microcatheter 600 that can extend distal to the distal access system to interact with the artery is the distal-most flexible portion 615. In some implementations, the overall length of the delivery system 700 can be between 120 cm-150 cm.

The collapsed payload 505 of the working device 500 can be housed within the payload portion 620 of the microcatheter 600. The payload portion 620, in comparison to the lengths provided above, can be much shorter. In some implementations, the payload portion 620 can be between 4 cm-8 cm in length. The collapsed working device 500 can be advanced as a unit within the payload portion 620 of the microcatheter 600 to a target location. This prevents the need for advancing a "bare" payload 505 through the entire length of a microcatheter 600 and eliminates friction and push-pull hassle of pushing the working device 500 such a great distance on its own. In some implementations, the payload portion 620 can have an outer diameter that is larger or similar in size to a diameter of a conventional microcatheter, which is typically 3 F. Generally, the outer diameter of the payload portion 620 is sized to be received within the inner diameter of the support catheter 200, which can be 0.054", 0.070", or 0.088". The distal portion 615 can have a reduced outer diameter compared to the payload portion 620 (see FIG. 8B) or can have a similar outer diameter as the payload portion 620 (see FIGS. 8A and 8C). Further, the distal portion 615 can have an inner diameter of between 0.017" to 0.027". The inner diameter of the distal portion 615 can allow for a procedural guidewire 805 to move freely within it as well as the working device 500 when it is deployed from within the payload portion 620 of the microcatheter 600. Generally, the outer diameter of the microcatheter 600 has a maximum size that is less than 0.048 inch and an inner diameter sized to allow passage of a guidewire 805 through it.

Where the distal portion 615 is the most flexible portion of the microcatheter 600, the proximal control element 625 of the microcatheter 600 is generally the stiffest component of the entire system 700. The proximal control element 625 can be used as a separate element for controlling bi-directional movement of the microcatheter 600 relative to the procedural guidewire 805 and to the control element 510. The proximal control element 625 of the microcatheter 600 can provide support to push the distal portion 615 across tortuous anatomies such as the terminal ICA from the less tortuous anatomy from the access puncture site (e.g. common femoral artery) to the proximal common carotid or the great artery takeoff.

As shown in FIGS. 8B-8C, the proximal control element 625 can have a reduced outer diameter compared to one or both the payload portion 620 and the distal portion 615. For example, the proximal control element 625 can be a spine or a hypotube or other rigid component similar to what is described above with respect to the proximal control elements of the support catheter 200 and the catheter advancement element 300. As a hypotube, the proximal control element 625 allows for the guidewire 805 or the control element 510 of the working device 500 to pass through it in an OTW fashion such that they extend through the single RHV 434 of the guide sheath 400 of the distal access system 100, as will be described in more detail below. It should be appreciated, however, that monorail formats in which the microcatheter has two exit ports is considered herein as well and will be described in more detail below.

It should be appreciated that the microcatheter 600 of the delivery system 700 need not be spined or include a hypotube, but instead can be an intact catheter as shown in FIG. 8A. When using an intact microcatheter 600, the control element 510 for the working device 500 may be longer than the distal access system 100. It should be similarly appreciated, the catheter 200 of the distal access system 100 also need not be spined and instead can be an intact catheter that has a uniform inner diameter from a proximal to distal end. The catheter 200 is shown in FIGS. 8A-8C as being spined and having a proximal control element 230. The microcatheter 600 housing the working device 500 also can be advanced through a non-spined, conventional catheter extending from the guide sheath 400.

Figure 21:
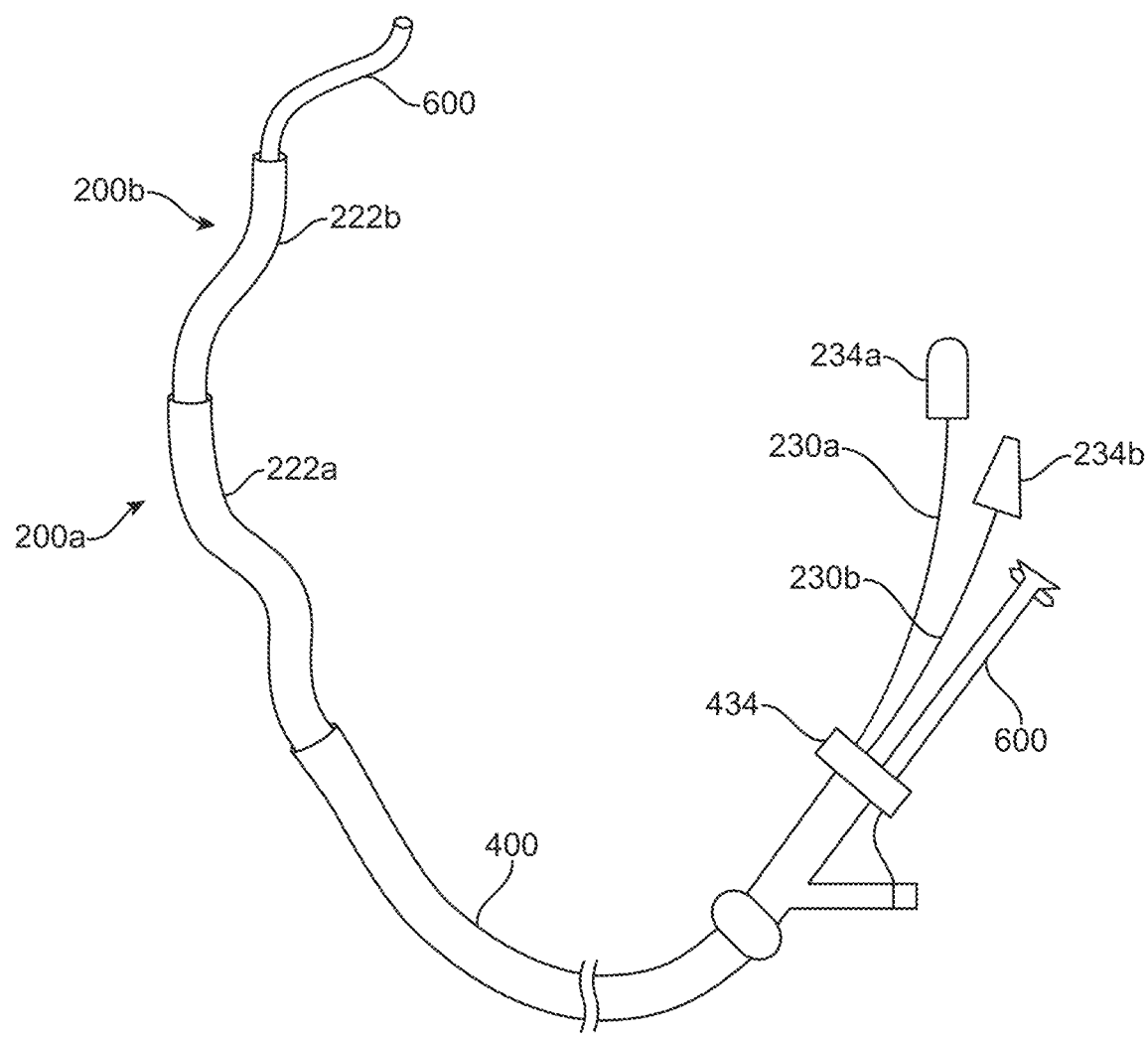
FIG. 21 illustrates an implementation of a nested catheter system.

The delivery system 700 also can be advanced through a series of nested support catheters 200 providing sequential extensions in length for the delivery system 700 to traverse. In an implementation shown in FIG. 21, a guide sheath 400 can be deployed as described elsewhere herein such that the distal end of the sheath 400 is advanced to a location in, for example, the internal carotid artery (ICA). A first catheter 200a can be advanced through the working lumen of the guide sheath 400 and out the distal end. The first catheter 200a can have a distal luminal portion 222a coupled to a proximal control element 230a as described elsewhere herein. The proximal control element 230a can have a smaller outer diameter compared to the outer diameter of the distal luminal portion 222a and can be coupled near a proximal opening from the lumen of the distal luminal portion 222a. The first catheter 200a can be advanced using a catheter advancement element as described elsewhere herein. The catheter advancement element can aid the advancement of the first catheter 200a through the vessel without hanging up on a severe angulation and/or a branching vessel. The first catheter 200a can be advanced through the working lumen of the guide sheath 400 and then through the vessel to a first target location. The catheter advancement element 300 can be removed from the lumen of the first catheter 200a. A second catheter 200b having a second catheter advancement element 300 can be advanced through the lumen of the first catheter 200a. The second catheter 200b can also include a distal luminal portion 222b coupled to a proximal control element 230b near a proximal opening from the lumen of the distal luminal portion 222b. Similar to the first catheter 200a, the proximal control element 230b of the second catheter 200b can have a smaller outer diameter compared to the outer diameter of the distal luminal portion 222b. The distal end of the second catheter 200b can be extended using its proximal control element 230b to extend past the distal end of the first catheter 200a such that the smaller diameter second catheter 200b can reach a target site located to a distal vessel having a narrower dimension than the location of the first catheter 200a. In this implementation, the first spined catheter 200a can act as a support catheter for the second spined catheter 200b. The inner lumen of the second spined catheter 200b can fluidly communicate with the inner lumen of the first spined catheter 200a that fluidly communicates with the working lumen of the guide sheath 400 forming a contiguous lumen formed of three sections of increasingly larger dimensions towards the proximal end of the catheter system. For example, the first catheter 200a can have a distal luminal portion 222a having an inner diameter of about 0.088" and the second catheter 200b can have a distal luminal portion 222b having an inner diameter of about 0.070" as described elsewhere herein. It should be appreciated that more than two nested spined catheters is considered and that their respective inner and outer diameters are sized to receive one another for use together. The corresponding ID and OD of the catheters can be sized such that they slide relative to one another, but still provide sufficient sealing. For example, the contiguous lumens created by the nested arrangement can seal against one another such that aspiration can be drawn through them and an appropriate pressure can be applied through the nested catheters to accomplish, for example, aspiration force sufficient for aspiration thrombectomy of distant clots. The contiguous lumen formed by the nested catheters can be used for advancement of a working device 500 housed within a microcatheter 600 as described elsewhere herein.

The proximal end of the nested catheter system can incorporate various gripping, organizing, and attachment features as described elsewhere herein. For example, the guide sheath 400 can include a proximal end coupled to a rotating hemostatic valve 434 that provides access to the working lumen through which the catheters can be inserted. Each of the components of the catheter system can extend proximally out from the valve 434. For example, the proximal control elements 230a, 230b of the catheters 200a, 200b, and the proximal end of the microcatheter 600 can extend through the valve 434. Proximal extensions of the catheter advancement element (not shown in FIG. 21) can also extend proximally through the valve 434. Each of these components in the nesting or telescoping catheter set can incorporate identifying features at their proximal end regions that distinguish them from one another. For example, each proximal control element 230a, 230b can include a tab 234a, 234b having a distinguishing shape, color, or other visual characteristic that is unique to that particular catheter. Each proximal control element 230a, 230b can include a coupling feature, such as a clip or other connector, that organizes the various control elements and prevents entanglement. Nesting catheters and their respective catheter advancement elements can be incorporated within a kit.

The term "control element" as used herein can refer to a proximal region configured for a user to cause pushing movement in a distal direction as well as pulling movement in a proximal direction. The control elements described herein can include spines, push wires, push tubes, or other elements having any of a variety of configurations. The proximal control element can be a push tube in that it is hollow or tubular. The proximal control element can also be solid and have no inner lumen, such as a solid rod, ribbon or other solid wire type element. Generally, the proximal control elements described herein are configured to move its respective component (to which it may be attached or integral) in a bidirectional manner through a lumen.

As mentioned, the microcatheter 600 can be configured as an over-the-wire (OTW) device or a rapid exchange device. The OTW microcatheter 600 (see FIG. 8A) can allow for the guidewire 805 and/or the control element 510 of the working device 500 (e.g. stent retriever) to enter/exit the lumen 605 of the microcatheter 600 at a proximal luer 634 coupled to the proximal end of the control element 625. In the rapid exchange device, a side opening or distal wire port 604 for the guidewire 805 can be located a distance away from both the distal and proximal ends of the device 600. The distal wire port 604 can be between 5-30 cm away from the distal tip of the microcatheter 600. In some implementations, the distal wire port 604 is positioned 30-38 mm from a distal end of the microcatheter 600. In some implementations, the distal wire port 604 is located a distance between 10 cm and 20 cm from the distal-most tip of the catheter 600.

FIGS. 12A-12B, 13A-13B, and 14A illustrate examples of a rapid exchange version of the microcatheter 600. As described above, the microcatheter 600 can include a payload portion 620 configured to house the working device 500 and a proximal control element 625 configured to manipulate the microcatheter 600 in a bi-directional sliding manner relative to the support catheter 200. The distal wire port 604 for the guidewire 805 (or a side opening 606 for the working device control element 510 to exit the lumen 605) can be located within a portion of the microcatheter 600 near where the working device 500 is housed within the payload portion 620 or can be located further proximal such as within the hypotube proximal control element 625. This is compared to OTW versions in which the guidewire 805 and/or the control element 510 exit the proximal luer 634 of the hypotube 625.

In some implementations, the proximal control element 625 is a hypotube coupled to a proximal luer 634. The lumen of the hypotube and the microcatheter portions can be in fluid communication with the luer 634 such that distal angiographic contrast injections can be performed through the luer 634 out the end of the microcatheter 600. The contrast can flow past the working device 500 housed in the payload portion 620 (past the one or more ports 604, 606 in the case of a rapid exchange device) and primarily into the distal portion 615 of the microcatheter 600.

The microcatheter 600 can transition in stiffness along its length similar to what is described above with respect to the support catheter 200 and the catheter advancement element 300. The distal microcatheter portion 615 (i.e. the portion intended to extend beyond the support catheter 200) is the most flexible and the proximal control element 625 is the stiffest part of the microcatheter 600. The proximal control element 625 of the microcatheter 600 can be stiffer than the stiffness of either the distal 615 and payload portions 620 alone. The guidewire 805 and control element 510 can run "side-by-side" within the proximal control element 625 of the microcatheter 600 and the three components together can be stiffer than even these catheter portions having the procedural guidewire 805 and the working device control element 510 extending therethrough. The stiffer proximal control element 625 can remain enclosed by the conduit formed by the lumens of the support catheter 200 and the guide sheath 400 such that it does not come into contact with anatomy directly.

Because the proximal control element 625 of the microcatheter 600 has the greatest degree of stiffness, this portion of the device can bear the brunt of greater pushing forces, for example, in order to deliver it across expected tortuosity as it approaches the terminal carotid. This can potentially put it at the highest risk of kinking in the system 700. The microcatheter 600 (as well as the other catheters described above having a rapid exchange port) can be designed to avoid kinking and hinging near the distal wire port 604, which could create advancement problems of the microcatheter 600. The risk for kink and bends, especially at the distal wire port 604 weak points can also be minimized by transitioning the flexibility in the microcatheter 600 at or just distal to the distal wire port 604. The flexibility of the microcatheter 600 transitions from the distal portion 615 towards a less flexible "intermediate" catheter portion, which can include the payload portion 620 as well as the distal wire port 604. Or the intermediate catheter portion can transition to the proximal control element 625 before giving rise to the distal wire port 604. The intermediate flexibility portion of the microcatheter 600 can resist kink of the distal wire port 604 of the procedural guidewire 805 and the proximal port 606 for the control element 510 of the working device 500, which will be described in more detail below with respect to FIGS. 15-20. The distal wire port 604 can be positioned within the stiffened intermediate portion between the distal portion 615 and the proximal control element 625. The variable stiffness of the microcatheter 600 can be achieved in a variety of ways.

The stiffer intermediate and proximal portions of the microcatheter 600 would tend to straighten cervical ICA loops and kinds of anatomy that may be encountered if applied directly. Thus, the stiffer portions of the microcatheter 600 are designed to remain within the conduit formed by the distal luminal portion 222 of the distal access catheter 200 during use. As discussed above, only the distal portion 615 is intended to extend distal to the distal access catheter 200. The overall length of the microcatheter 600 and the length of the spined catheter 200 relative to the single RHV 434 can be designed to prevent any other portion of the microcatheter 600 besides the flexible distal portion 615 from exiting the catheter 200 to prevent straightening forces from being imposed on the anatomy. The spined catheter 200 can be long enough that it extends across the entire length of the cervical ICA and terminal ICA in order to reach targets as far distal as the ACA and M2 section of the middle cerebral artery. The distal luminal portion 222 is flexible along that entire distance. Overall length of the microcatheter 600 can also be controlled to ensure the distal wire port 604 and the proximal wire port 606 on either end of the intermediate catheter portion are maintained inside the distal luminal portion 222 of the catheter 200 when expected movements are to occur. For example, when the microcatheter 600 is most distally extended and the microcatheter 600 is traversing the terminal carotid (either with or without the distal access catheter 200) to the level of the ACA, M1 or M2 branches of the MCA. The distal wire port 604 thus, can remain "sleeved" when moved thereby minimizing the risk of kinking or folding of the procedural guidewire 805 and/or control element 510 of the working device 500.

Figure 11A:
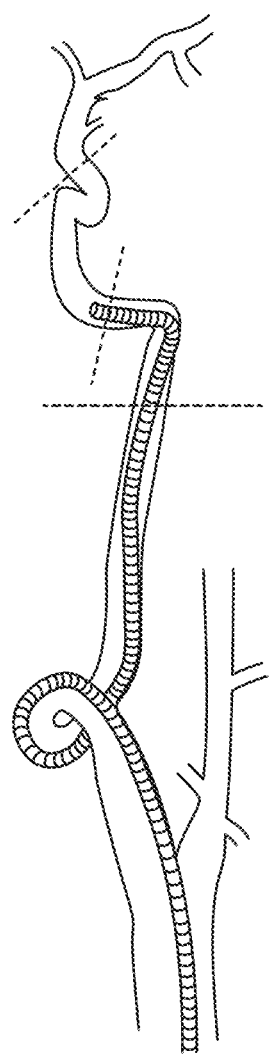
FIGS. 11A-11B illustrate the flexibility of the distal access catheter passing through the cervical carotid and beyond the guide sheath providing a conduit for insertion of less flexible components into the cervical ICA and beyond.
Figure 11B:
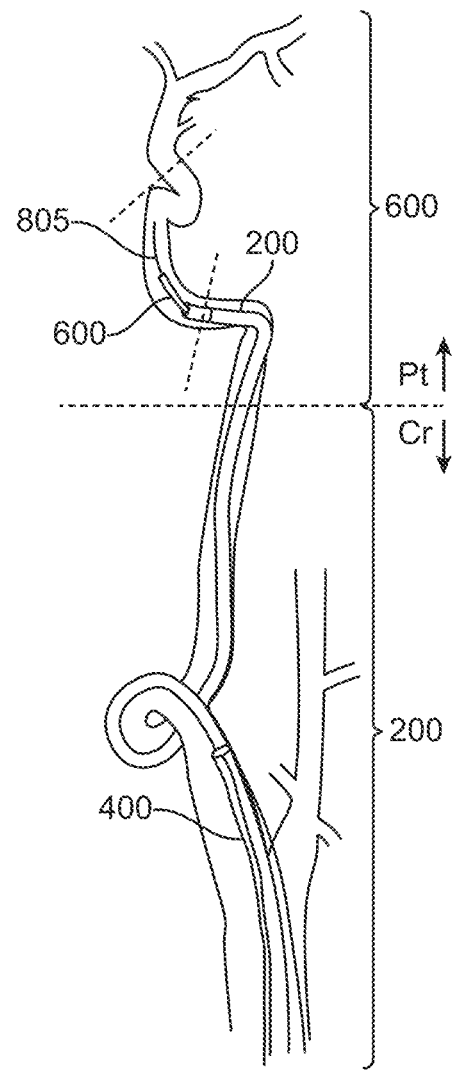

FIGS. 11A-11B show how the spined distal access catheter 200 has extreme flexibility passing through the cervical carotid extending beyond a guide sheath 400 and provides a conduit for insertion of the less flexible components of the working device delivery system 700. On occasion, the tortuosity of the cervical ICA and distal carotid to the carotid terminus can be such that the distal access only reaches the petrous carotid (see FIG. 11B). The spined catheter 200 can be delivered via the guide sheath 400 (see FIG. 11B), which is typically much stiffer and supportive to prevent kinking of the catheter systems from the access point (e.g. common femoral artery) as the takeoff of the great vessels is approached and the carotid anatomy entered. The stiff guide sheath 400 can be placed as high as possible in the ICA. However, when cervical ICA tortuosity is present, which can be common in the elderly population, then the guide sheath 400 is typically positioned below the area of severe kink or looping to avoid straightening that segment. In this implementation, the length of the extremely flexible catheter portion 222 of the spined distal access catheter 200 can be at least 30 cm and may be 38 cm-40 cm in length to provide sufficient overlap with the guide sheath 400 when the catheter 200 is positioned just proximal to a severely kinked or looped cervical ICA. The length of the entire spined catheter 200 can be such that the distal luminal portion 222 is the only portion of the device that exits the guide sheath 400, which can be between 80 cm-90 cm long, which still keeping some length of overlap for sealing. The microcatheter 600 can extend 3-5 cm beyond the distal end of the spined catheter 200. If distal access obtained by the spined catheter 200 is to the proximal carotid, the delivery of a working device 500 to the M2 branch may involve a microcatheter length extending beyond the support catheter 200 that is approximately 12 cm to 15 cm. Thus, the distal portion 615 of the microcatheter 600 can be approximately 18 cm to ensure sufficient length for accessing these sites even if distal access obtained by the spined catheter 200 is limited. The flexibility of the distal portion 615 combined with the kink-resistance of the stiffer proximal portions of the microcatheter 600 allow it to navigate independently through the bony petrous portion of the carotid and the carotid siphon and into the anterior circulation of the cerebral vascular anatomy. Generally, however, the microcatheter 600 need only navigate through the conduit provided by the access catheter lumens.

Components of the distal access system 100 and the working device delivery system 700 can include one or more markers providing information regarding their positions relative to one another as well as relative to the vascular anatomy. As discussed above and shown in FIG. 2A, one or more radiopaque markers 411 can be disposed near a distal tip 406 of the guide sheath 400. One or more radiopaque markers 224 can also be positioned near a distal tip of the distal access catheter 200 and one or more radiopaque markers 344 can be positioned near a distal tip of the catheter advancement element 300. The proximal control element 230 of the distal access catheter 200 can include one or more markers 232 as can the proximal control element 366 of the catheter advancement element 300. The proximal control element 625 of the microcatheter 600, the proximal control element 510 of the working device 500, and the guidewire 805 can each include one or more markers along their lengths to provide information regarding their relative positions to each other as well as to the RHV 434 of the guide sheath 400. The specific markers can minimize fluoroscopy use and accidental advancement of one of the components beyond a desired point (e.g. the microcatheter 600 beyond the distal tip of the catheter 200). The markers can vary in size, shape, and locations as well as be distinct from one another to provide quick and easy information regarding the component on which it is positioned and its overlap with one or more of the other components.

The distal access system 100 and the delivery system 700 can have a working device 500 pre-loaded and housed within the lumen of the microcatheter 600 adjacent a side opening (e.g. on a proximal side of the side opening) and advanced over a procedural guidewire 805. The working device 500 can be pre-loaded by pulling the working device 500 into the distal opening at the distal tip of the microcatheter 600 and guiding the working device control element 510 out a proximal port 606 in the microcatheter 600. The proximal port 606 can be located a distance proximal to where the working device 500 is housed in the payload portion 620. The expandable payload 505 can be positioned outside the distal opening external to the lumen 605 of the microcatheter 600 and the proximal control element 510 extending through the lumen 605 and out through the proximal opening 606. The expandable payload 505 of the working device 500 can be withdrawn or pulled into the payload portion 620 of the microcatheter 600 until the expandable payload of the working device 500 enters the lumen 605 through the distal opening and slides proximally past the side opening for the guidewire 805 (i.e. the distal wire port 604) until the expandable payload 505 is housed within the lumen 605 adjacent to the distal wire port 604 on a proximal side of the port. The procedural guidewire 805 can also be back-loaded into the distal tip of the microcatheter 600 and guided to exit out the distal wire port 604 of the microcatheter 600. The distal wire port 604 through which the procedural guidewire 805 extends can be located distal to the payload portion 620 housing the working device 500 such that the procedural guidewire 805 does not extend through the payload portion 620 and the payload of the working device 500. The procedural guidewire 805 can be loaded within the lumen 605 of the microcatheter 600 after the expandable payload 505 is positioned on the proximal side of the side opening 604 such that the push wire 510 and the procedural guidewire 805 do not extend side-by-side within the lumen 605.

The proximal end of the working device control element 510 can have a wire introducer or torquer 544 applied to it. Similarly, the proximal end of the guidewire 805 can have a wire introducer or torquer 844 applied to it. The torquer 844 for the guidewire 805 can be discernable from the torquer 544 on the control element 510 of the working device 500, such as by color, shape, or other identifier to allow easy identification. The procedural guidewire 805 can be pulled into tip-to-tip position with the distal tip of the microcatheter 600 to facilitate passage into the support catheter 200. The microcatheter 600, guidewire 805, and working device 500 can be prepped and pre-loaded in advance and set aside until needed during a procedure, for example during CT scanning (e.g. after identifying diameter and length of the working device 500 or during patient transport), or when obtaining femoral access. The microcatheter 600, guidewire 805, and working device 500 can also be prepped simultaneously with gaining distal access and obtaining base catheter position in the internal carotid.

The microcatheter 600 pre-loaded with the working device 500 and the procedural guidewire 805 can be advanced until the microcatheter 600 extends across a target located within the intracranial neurovasculature. Pre-assembled stent retriever systems for neurovascular use in stroke treatment have never before been a possibility because the pre-loading of the stent retriever into the microcatheter sacrificed the deliverability of the system to reach the levels of needed to treat the stroke. However, the support catheter 200 of the present system is specifically configured to navigate the tortuous neuroanatomy artificially extending the length of the guide sheath 400 and providing a complete and smooth conduit through to the target anatomy for ease of advancement of the pre-loaded delivery system 700 that does not apply straightening forces and maintains the natural curvatures of the anatomy. The smooth conduit provided by the support catheter 200 and the guide sheath 400 means the delivery system 700 can be pre-loaded with the working device 500.

Figure 9H:
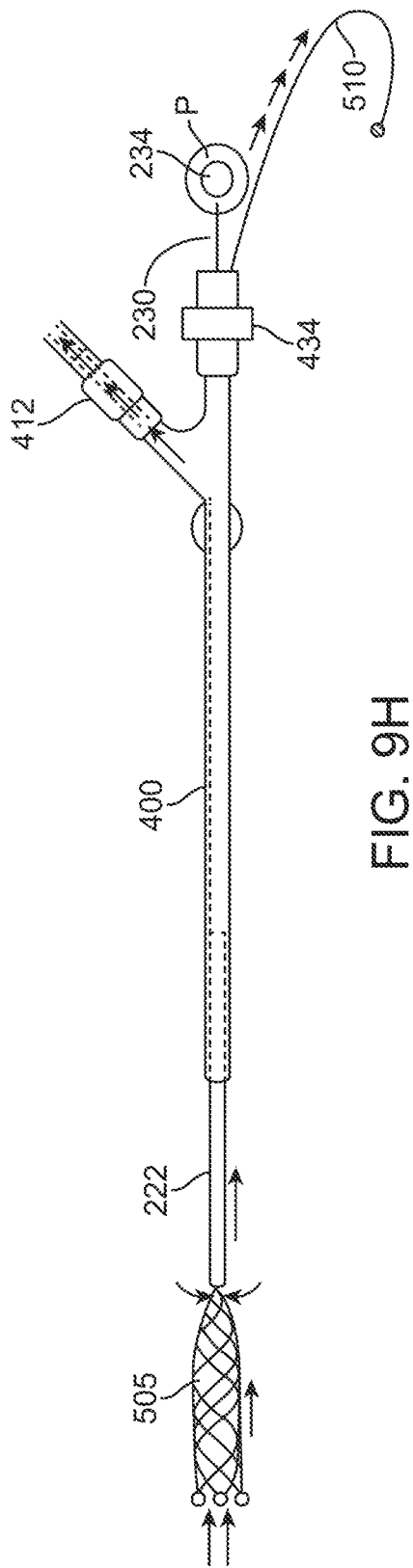

In use and as best shown in FIGS. 9A-9I, the support catheter 200 can be inserted through a single RHV 434 coupled to a proximal end of the guide sheath 400 such that the distal luminal portion 222 extends the length of the catheter conduit to just the length to allow access from the access site entry point (e.g. the common femoral artery) to just proximal to the target for implant delivery. Use of a spined support catheter 200 can allow for the minimum distance to reach the target due to the telescoping of the catheter 200 relative to the guide sheath 400. The RHV 434 can have a single head as shown in FIG. 9A or can include a two-headed RHV as shown in FIGS. 10A-10H). After securing distal access, the operator can fix the distal access point in place with a pinch P creating a control point where the secured catheter 200 provides support for smaller catheters and wires that may be passed through it. FIG. 9B shows the microcatheter 600 having the pre-assembled, unexpanded payload 505 of the working device 500 contained within it inserted together with the procedural guidewire 805 through this single RHV 434 of the distal access system 100. The three components are advanced in unison through the RHV 434 to advance the distal end of the microcatheter 600 very near the target. The microcatheter 600 and the guidewire 805 can be inserted through a single head of the single RHV 434 of the guide sheath 400 or through its own dedicated head if a two-headed RHV is being used. A two-headed RHV allows the support catheter 200 to be inserted through its own dedicated port to eliminate the need to manage the catheter positioning when working with the dedicated working channel for the IDS 700. Regardless of whether the single RHV is single-headed or dual-headed, the system provides a greater ease of use compared to typical tri-axial systems in which each of the microcatheter, the distal access catheter and the guide sheath would be coupled to their respective RHVs resulting in a significantly longer system requiring multiple operator hands to manage the multiple site of interaction. This can be especially cumbersome when a two-handed maneuver is needed at one of the RHVs (e.g. advancement of a microcatheter at an the RHV, advancing the guidewire, etc.). As mentioned above, a torquer 844 can be attached near a proximal end of both the guidewire 805 as well as the control element 510 of the working device 500. In conventional tri-axial systems, the torquers must be removed and replaced to provide grip to the working device control element 510 as the embolus is typically very adherent and a firm pull for movement is often needed. It should be appreciated that although the systems are described herein as being capable of delivery through a single RHV 434 that the more than a single RHV can also be used as in more typical tri-axial systems.

Again with respect to FIG. 9B, advancement of the loaded IDS 700 into the RHV 434 can include a first hand holding the RHV 434 and a second hand grasping the proximal regions of the microcatheter 600, the guidewire 805, and the working device 500 together in a single pinch P. The arrangement of these three components can be prearranged as described elsewhere herein and their juxtaposition maintained with each throw of the advancement through the system. Once the tip of the IDS 700 reaches the distal luminal portion 222 of the spined catheter 200, the guidewire 805 can be isolated from the other components (e.g. control element 510 of the working device 500, proximal control element 625 of the microcatheter, and proximal control element 230 of the support catheter 200), which can be gathered into a single pinch P and held together in a stationary position while the guidewire 805 is advanced independently (see FIG. 9C). The guidewire 805 can be advanced across the embolus to allow for microcatheter 600 placement. Once the guidewire 805 is positioned across the target, it can be held fixed by adding the proximal region of the guidewire 805 to the pinch P holding the support catheter 200 while the microcatheter 600 with the working device 500 housed therein are adjusted to be advanced over the guidewire (see FIG. 9D). The system allows the guidewire 805 to be held fixed while the microcatheter 600 is advanced rather than pistoning back and forth as can occur in conventional systems.

Figure 9I:
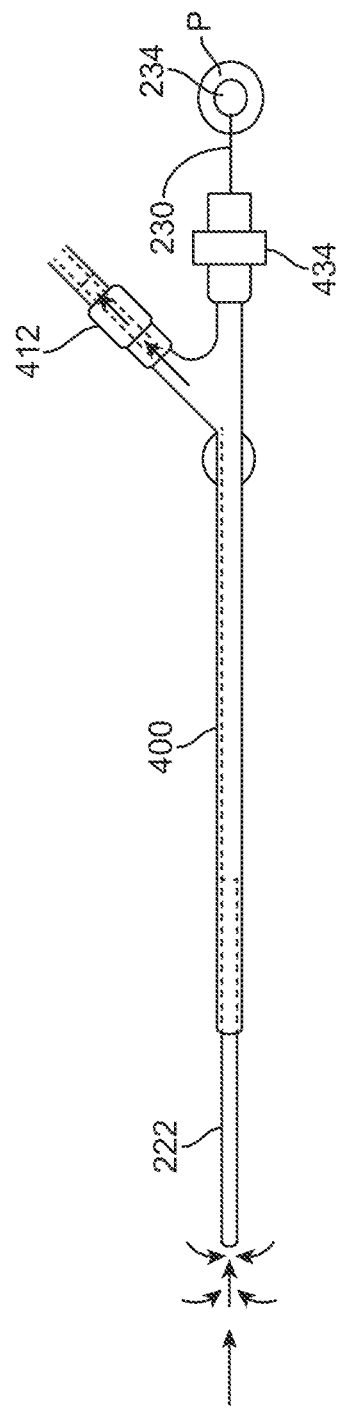

The microcatheter 600 can reach the target across the embolus with minimal to no movement of the distal tip of the guidewire 805. FIG. 9E shows the microcatheter 600 after the guidewire 805 is removed. Upon removal of the guidewire 805, the proximal control element 230 of the support catheter 200 and the microcatheter 600 can be gathered in a single pinch P and the control element 510 of the working device 500 advanced to fix the position of the microcatheter 600 and advance the working device 500 into position to deploy the expandable payload 505 from the lumen 605 of the microcatheter 600 through the distal opening to treat the target. Thus, the working device 500 can be advanced distally through the lumen 605 to the distal end region of the microcatheter 600 while the microcatheter 600 and the support catheter 200 are pinched together and fixed in a stationary position P. Once the expandable payload 505 of the working device 500 is in position, the control element 510 of the working device 500 and the proximal control element 230 of the support catheter 200 can be pinched together P and held substantially fixed in a stationary position as the microcatheter 600 is withdrawn proximally by pulling on its control element 625 at the RHV 434 (see FIG. 9F). The expandable payload 505 of the working device 500 is unsheathed allowing it to deploy or expand the payload 505 at the target (see FIGS. 9F-9G). Once the working device 500 is unsheathed, the single RHV 434 can be tightened. The single RHV 434 is tightened only a single time during the procedure in preparation for initiation of aspiration to create a sealed system. It should also be noted that the torquer 544 on the control element 510 of the working device 500 need not be removed or adjusted. Following delivery of the microcatheter 600 and guidewire 805 withdrawal, aspiration can be turned on at the single RHV 434, for example, in AIS embolectomy procedures. Aspiration can be performed before withdrawal of the working device 500 into the support catheter 200 and removal followed by "SMAT" with aspiration via the catheter 200 to remove embolic debris with aspiration alone or with aspiration while withdrawing the catheter 200 by pulling on the proximal control element 230. In the "Solumbra" approach, the working device 500 and the distal access segment 200 can be withdrawn as a unit by pinching P both control elements 510, 230 and pulling them out of the RHV 434 as a unit. The single RHV aspiration port 412 facilitates this with a single-point of continuous aspiration (FIGS. 9H-9I).

The delivery systems described herein allow advancement and positioning of a triaxial system of catheters through a single RHV to deliver working devices while avoiding the requirement of "pushing" the device payload 505 the entire length of the catheter delivery system 700 as is typical in conventional stent retriever systems and methods. The working device payload 505 of the delivery systems 700 described herein can be pre-loaded within the microcatheter 600 such that they can be advanced in unison to the target and avoids the need for advancing the payload "bare" through the entire microcatheter length. Further, the microcatheter 600 of the delivery systems 700 described herein can be shorter than conventional stent retriever microcatheters, which are typically about 145 cm or longer and configured to accept stent retrievers having a push wire of 180 cm in length. For example, the microcatheter 600 of the delivery system 700 described herein can be about 130 cm in working length compared to conventional stent retriever systems and in some cases between 30-50 cm shorter than conventional systems. This shortened length allows for the operator to work with a working device 500 having a proximal control element 510 that is significantly shorter than the typical stent retriever push wires and be used with a distal access system 100 that is shorter. For example, the distal luminal portion 222 of the support catheter 200 can be between 20-40 cm long and the proximal control element 230 can be between 90-100 cm long. The guide sheath 400 through which the support catheter extends can be between 80-90 cm long. When the support catheter 200 extends beyond the distal end of the guide sheath 400 while maintaining the overlap 348, a channel can be created that is approximately 115 cm long for device delivery.

A single operator can use the systems described herein by inserting the delivery system 700 through the support catheter 200 artificially extending the length of the guide sheath 400 because rather than the delivery system 700 and the support catheter 200 each having their own RHV in addition to the RHV of the guide sheath, they are both inserted through the single RHV 434 on the guide sheath 400. It should be appreciated that the catheter 200 and microcatheter 600 housing the working device payload 505 can be advanced through the same port of the single RHV 434 or can be advanced through separate ports of the single RHV 434, for example, if the RHV 434 is a dual-headed RHV as shown in FIG. 10A-10H. In either scenario, whether a single channel RHV or a dual-headed RHV is used, the extra RHVs are eliminated as are the extra length and extra hand movements needed to deliver the interventional devices. The shorter lengths of the systems described herein in combination with their insertion through a single RHV on the guide sheath provide an ease of use advantage for any operator or team of operators and can change a procedure from being a two-person procedure to a one-person single operator procedure. In the setting of conventional, long stent retrievers and microcatheters, the distance the stent retriever microcatheter extends down the table and the distance the RHV of the microcatheter extends away from a first operator requires a second operator to manage the position of the microcatheter to maintain hemostasis and manage any manipulations at the RHV of the microcatheter. Conventional triaxial or quadraxial or pentaxial systems used in stroke intervention require at least two operators.

FIGS. 10A-10H illustrate an implementation of a method using a dual-headed RHV. The RHV 434 allows for the introduction of devices through the sheath 400 while preventing or minimizing blood loss and preventing air introduction into the sheath 400. The dual-headed RHV 434 can include two working ports 435, 436 configured to receive one or more components of the system 10. The dual-headed RHV 434 can include an arm 412 that can be used as a point of aspiration during portions of the procedure or as a line to flush the sheath 400 with saline or radiopaque contrast. In an implementation, the first port 435 is dedicated to receive and lock into position the control element 230 of the catheter 200 and a second port 436 dedicated to receive components of the delivery system 700 including the procedural guidewire 805. This avoids the need for doing this manually by a pinch during the remainder of the procedure steps as described above. This configuration provides for betting organization and handling of the components in the system 10 while still maintaining them well within the reach of a single operator. The RHV 434 can be integral to the sheath 400 or the sheath 400 can terminate on the proximal end in a female Luer adaptor to which a separate hemostasis valve component, such as a passive seal valve, a Tuohy-Borst valve or RHV may be attached. It should be appreciated that the arrangement of the RHV can vary. FIGS. 10A-10H show the upper head is the "working" head and the second head is dedicated to securing the distal access spined catheter 200 as shown elsewhere herein. This allows the operator to fix the distal access point in place with a "pinch" from the locked RHV 434. As described previously, this becomes a "control point" where the secured catheter 200 provides support for smaller catheters and wires that are passed through it.

The support catheter 200 can be inserted through a port of a single RHV 434 coupled to a proximal end of the guide sheath 400 such that the distal luminal portion 222 extends the length of the catheter conduit to just the length to allow access from the access site entry point (e.g. the common femoral artery) to just proximal to the target for implant delivery. The proximal control element 230 of the spined catheter 200 can be locked in position by the dedicated RHV 434 (see FIG. 10A). The guidewire 805, working device 500 and microcatheter 600 can be advanced into a separate port of the RHV 434, the "working RHV", as a unit and advanced to the tip of the distal access catheter 200 (see FIG. 10B). Once positioned at the distal tip of the catheter 200, the guidewire 805 can be advanced independently by adjusting the "pinch" to capture both the working device 500 and microcatheter 600 as the guidewire 805 advanced across the target (see FIG. 10C).

Figure 10D:
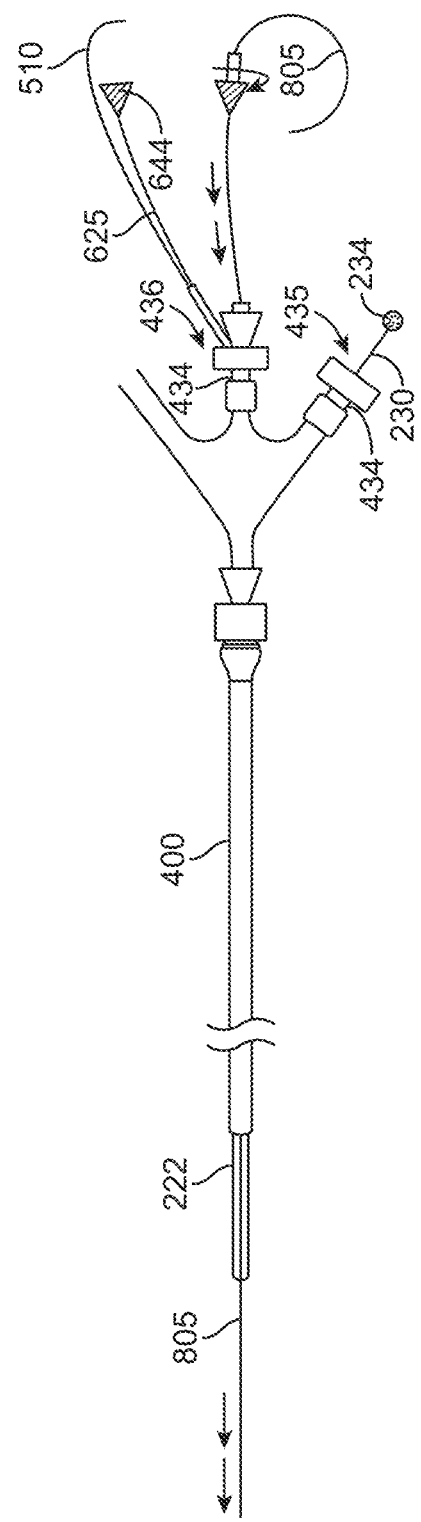
Figure 10G:
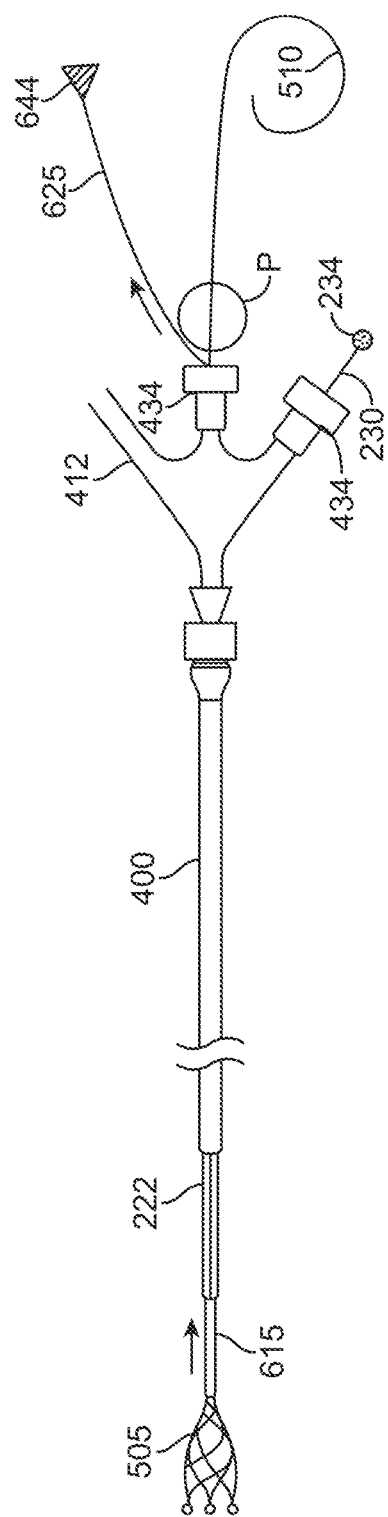
Figure 10H:
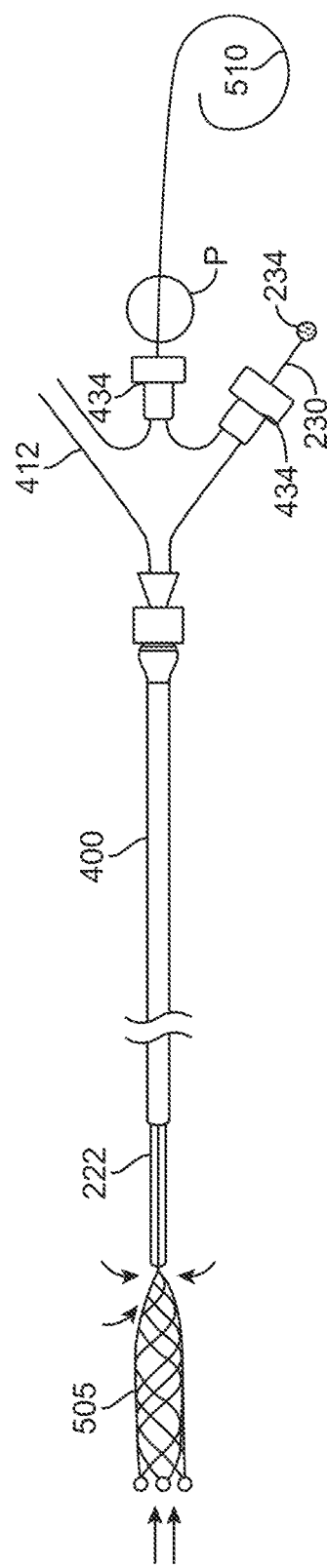

In some implementations, a wire introducer or torquer can be placed that allows the RHV port 436 for the working device delivery system 700 to be locked down fixing the microcatheter 600, the working device 500 and the wire introducer 644 in place. FIG. 10D shows how the wire introducer 644 can be placed that allows the microcatheter 600 and working device 500 to be locked down which fixed them into place. The wire introducer 644 can protect the guidewire 805 from being fixed by the RHV 434 and allow for maneuvering of the guidewire 805 using a traditional torque/guidewire advancement with free delivery of torque to the tip of the guidewire 805, which can be a pre-shaped tip. The wire introducer 644 can also allow advancement and withdrawal of the guidewire 805 with the RHV 434 fixing the microcatheter 600 and the working device 500. Once the guidewire 805 is positioned across the target, it can be held fixed by adjusting and pinching the proximal guidewire 805 and loosening the working RHV 434 to allow advancement of the control element 625 of the microcatheter 600 and the control element 510 of the working device 500 together as a unit (see FIG. 10E). The action of the pinch can fix the guidewire 805 and allows the microcatheter control element 625 and the working device control element 510 to advance over the guidewire 805. Again, any back-and-forth piston movements of the guidewire 805 during delivery system 700 advancement is prevented. The microcatheter 600 can be advanced safely without concern for distal guidewire trauma. The guidewire 805 can be removed once the working device 500 is in position. The working device 500 position is fixed by pinching the control element 510 together with the proximal element 230 of the support catheter 200 (see FIG. 10F) and unsheathed by pulling on the microcatheter 600 (see FIG. 10G). The microcatheter 600 can be removed while keeping the working device 500 in place with a pinch and then short exchange. When the microcatheter 600 is completely removed, the RHV 434 can be tightened at both heads 436 and aspiration initiated through arm 412 (FIG. 10H).

Standard stent retriever techniques call for the stent portion to be fully released allowing for the struts to integrate into the embolus for a few minutes. The operator can then choose to perform a "Solumbra" or "SMAT" procedure. For example, the stent retriever can be withdrawn into the distal access catheter 200 and removed followed by "SMAT" with aspiration via the distal catheter 200 to remove embolic debris with aspiration alone or with aspiration while withdrawing the distal access segment by pulling on the spined catheter 200. The SMAT approach is particularly useful with the dual-head RHV configuration shown in FIGS. 10A-10H. With the "Solumbra" approach, the stent retriever and distal access segment are withdrawn simultaneously by pinching both pull wires. Both pull wires can be approximated and pulled out of their closed RHVs as a unit. The Solumbra approach is particularly useful with the single-head RHV configuration shown in FIGS. 9A-9I.

It should be appreciated that the torquer 544 on the working device 500 need not be removed or adjusted. Rather, the torquer 544 can be positioned to be tightened should pulling of the working device 500 upon being embedded in the embolus require additional grip on the control element 510.

Figure 12A:
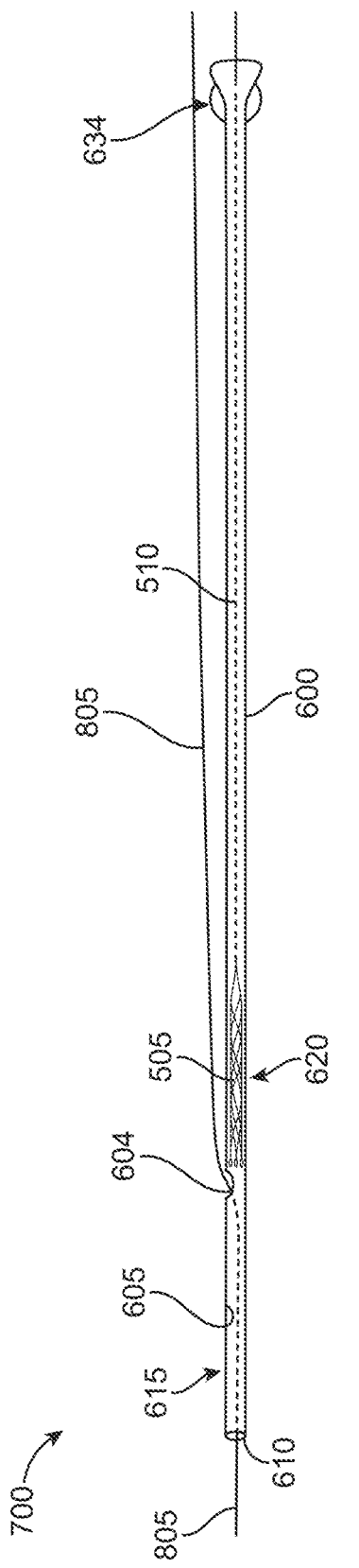
FIGS. 12A-12B illustrate implementations of single operator working device delivery systems in a side-by-side arrangement with a procedural guidewire.
Figure 12B:
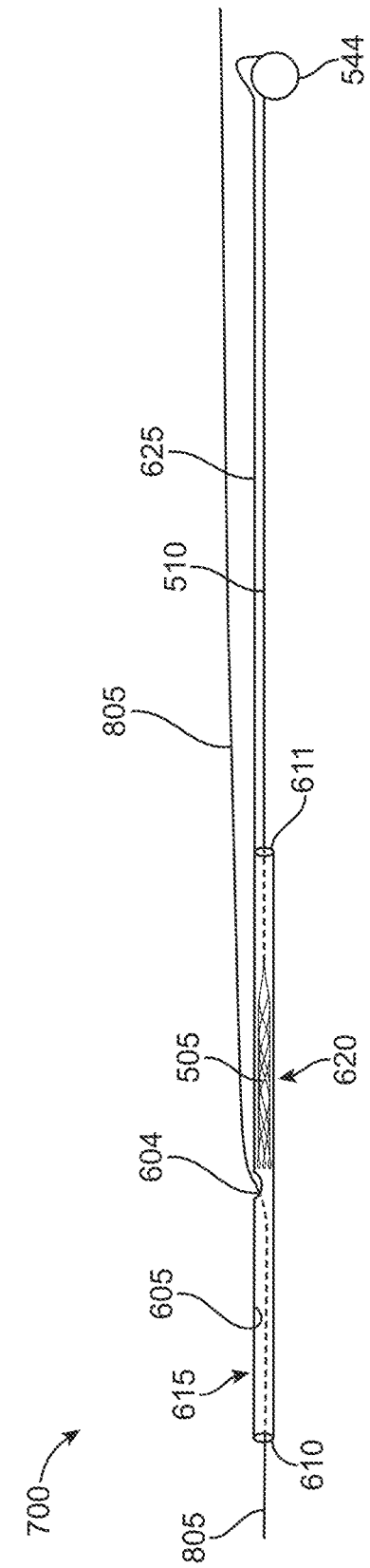
Figure 14A:
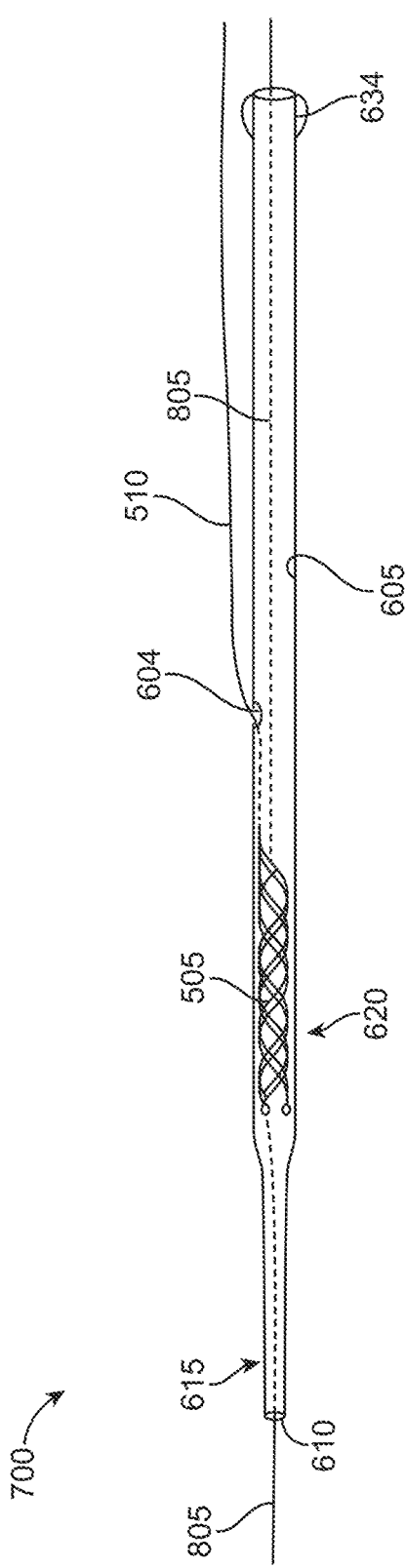
FIGS. 14A-14B illustrate implementations of single operator working device delivery systems having a microcatheter with a step-up in outer diameter.
Figure 14B:
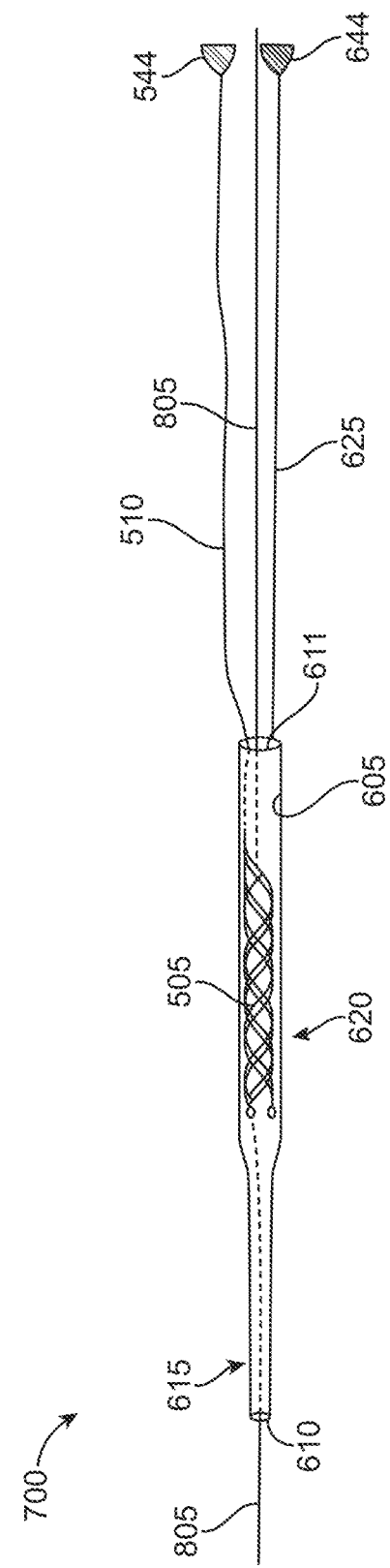
Figure 15A:
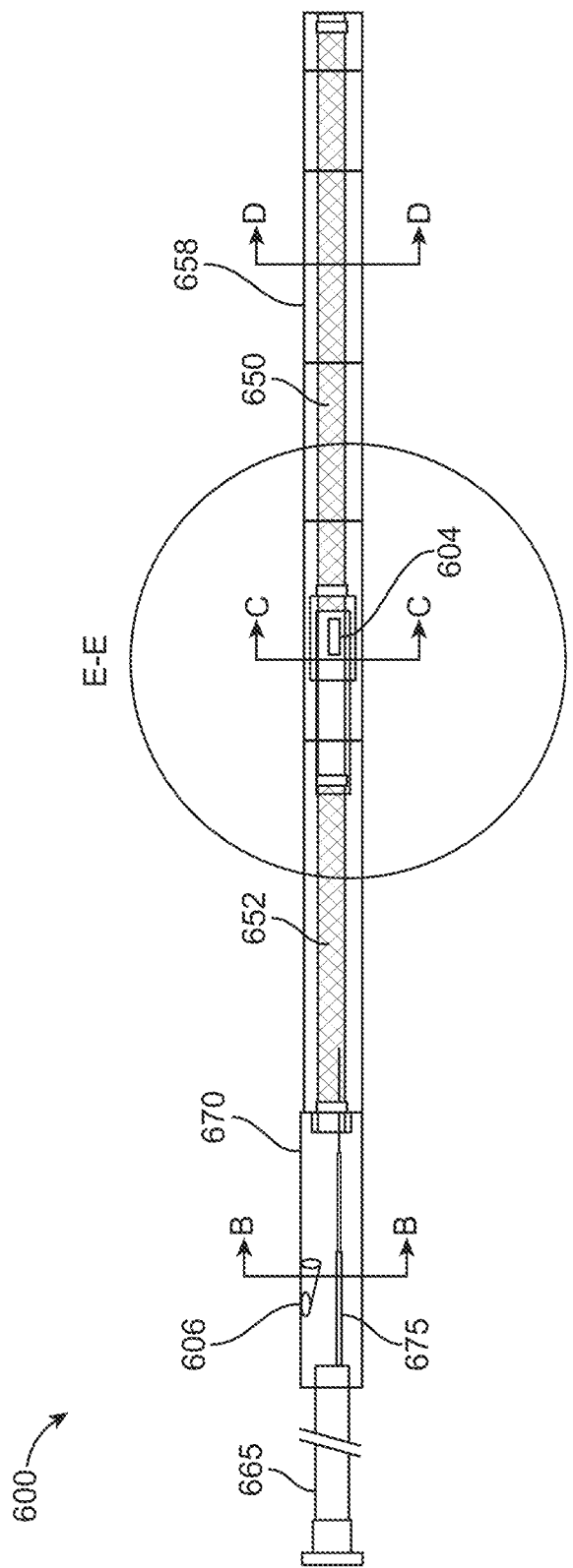
FIG. 15A illustrates a schematic view of an implementation of a rapid exchange microcatheter for delivering a working device to the neurovasculature for the treatment of stroke.
Figure 17C:
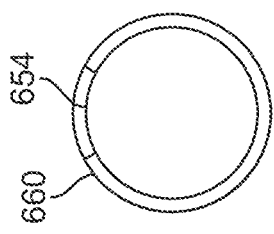
FIGS. 17A-17D illustrate top, side, and cross-sectional views of an implementation of a coupler for the microcatheter of FIGS. 16A-16C.
Figure 17B:
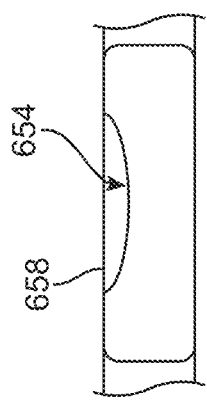
Figure 17A:
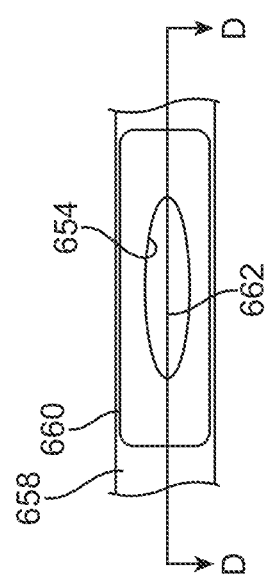
Figure 17D:
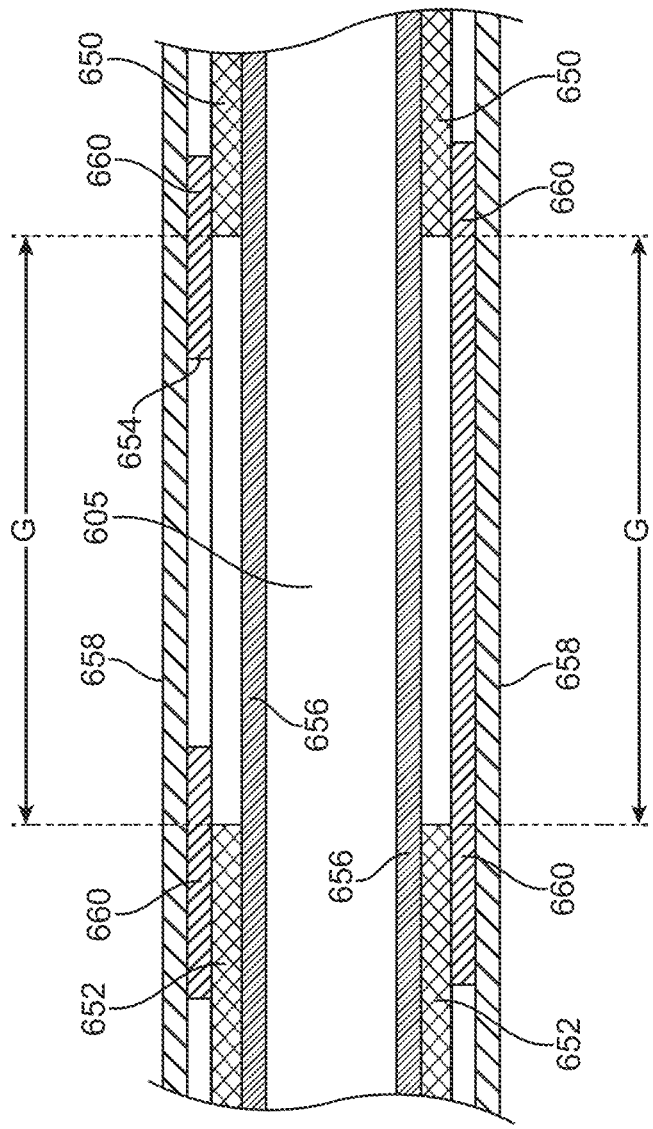
Figure 19A:
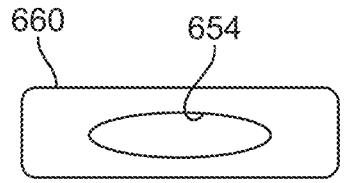
FIGS. 19A-19C illustrate top, side, and cross-sectional views of an implementation of a coupler for the microcatheter of FIG. 16A-16C.
Figure 19B:
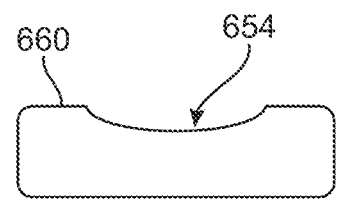

The relative relationships of the intact catheter delivery system 700 with a stent retriever as the self-expanding payload 505 are illustrated in FIGS. 12A, 13A, and 14A. The relative relationships of the spined delivery system 700 with a stent retriever as the self-expanding payload 505 are illustrated in FIGS. 12B, 13B, and 14B. Although the working device 500 is illustrated as a stent retriever it should be appreciated that any of a number of working devices are considered herein (e.g. flow diverter, intracranial stent, etc.).

FIGS. 12A-12B illustrate implementations of a single operator delivery system 700 having an intact microcatheter 600 (FIG. 12A) or a spined microcatheter 600 (FIG. 12B) for delivering the working device 500 having a self-expanding payload 505. The procedural guidewire 805 can run side-by-side with the catheter delivery system 700 and enter the lumen 605 of the microcatheter 600 at a skive or entry port 604 located just distal to a point where the payload 505 is garaged within the payload portion 620. The guidewire 805 can extend through the microcatheter 600 near the distal region 615 and exit out the distal opening 610 of the microcatheter 600. The unexpanded payload 505 can itself be controlled in its positioning within the microcatheter 600 by the control element 510. The control element 510 can run through the lumen 605 of the proximal length of the microcatheter 600 and out of the proximal luer 634 of the intact microcatheter 600 as shown in FIG. 12A or exit out the proximal opening 611 from the microcatheter lumen 605 of the spined microcatheter 6000 as shown in FIG. 12B. The guidewire 805 can enter the microcatheter 600 through the port 604 located just distal to the payload portion 620 housing the payload 505. The guidewire 805 can be used to navigate across the target distal to the distal opening from the lumen 223 of the catheter 200 of the access system 100 and held in place as the microcatheter 600 housing the payload 505 is advanced up to the target. In the case of the spined microcatheter 600 shown in FIG. 12B, the control element 510 of the working device 500 and the control element 625 of the microcatheter 600 can be advanced together. The microcatheter 600 of the delivery system 700 can be advanced across the target as is typical for placement of intracranial working devices 500 such as a stent retriever. The delivery system 700 can be held in place while the guidewire 805 is withdrawn. After guidewire 805 removal, the lumen 605 of the microcatheter 600 is free for the advancement of the payload 505 into position across the target site. The payload 505 can be advanced by its control element 510 while holding the microcatheter 600 fixed through the lumen 605 of the microcatheter 600 from the payload portion 620 towards the distal opening 610 and across the cerebral target. Once the payload 505 is visualized to be in position, the microcatheter 600 can be removed. The payload 505 can be held fixed in position with the control element 510 while the microcatheter 600 is withdrawn by retracting at the RHV 634 as shown in FIG. 12A or if the microcatheter 600 is spined as shown in FIG. 12B, at the control element 625. The payload 505 is then unsheathed and allowed to self-expand as the microcatheter 600 is removed from the system. The above sequence of delivery and deployment can avoid the requirement of pushing the payload 505 through the entire length of a microcatheter, which runs the entire length of the distal access system 100 having the support catheter 200 extending through the guide sheath 400. Rather, the payload 505 traverses only the distal portion 615 of the microcatheter 600 before the microcatheter 600 is withdrawn.

FIGS. 13A-13B illustrate implementations of a single operator delivery system 700 having an intact microcatheter 600 (FIG. 13A) or a spined microcatheter 600 (FIG. 13B) for delivering a working device 500 having a self-expanding payload 505. The procedural guidewire 805 can run the entire length of the delivery system 700. In the implementation of FIG. 13A, the guidewire 805 can enter the lumen 605 of the microcatheter 600 at the proximal luer 634. In the implementation of FIG. 13B, the guidewire 805 can enter the lumen 605 of the microcatheter 600 at a proximal opening 611 into the payload portion 620 of the microcatheter 600 housing the expandable payload 505 in a collapsed configuration. The guidewire 805 can extend through the self-expanding payload 505 housed within the payload portion 620 and exit out the distal opening 610 of the microcatheter. This can allow the coaxial movement of the guidewire 805 through the microcatheter 600 rather than the side-by-side positioning seen in FIGS. 12A-12B providing better wire torque and responsiveness. The unexpanded payload 505 can be controlled in its positioning within the microcatheter 600 by the control element 510. The control element 510 can exit the payload portion 620 at the port 604 located just proximal to the position of the expanding payload 505. The guidewire 805 can be used to navigate across the target distal to the distal opening from the lumen 223 of the catheter 200 of the access system 100 and held in place as the microcatheter 600 housing the payload 505 is advanced up to the target. In the case of a spined microcatheter 600 shown in FIG. 13B, the control element 510 of the working device 500 and the control element 625 of the microcatheter 600 can be advanced together. The microcatheter 600 of the delivery system 700 can be advanced across the target as is typical for placement of intracranial working devices 500 such as a stent retriever. The guidewire 805 can then be removed or the payload 505 advanced over the guidewire 805. The payload 505 can be advanced through the lumen 605 of the microcatheter 600 from the payload portion 620 towards the distal opening 610 after delivery of the distal microcatheter 600 across the target. The payload 505 can be advanced by holding the microcatheter 600 fixed and advancing the payload 505 by the proximal control element 510 under fluoroscopic guidance to the target. Once the payload 505 is visualized to be in position, the microcatheter 600 can be withdrawn. The expanding payload 505 can be held fixed via the control element 510 and a monorail exchange performed as the control element 510 exits the RHV 634.

FIGS. 14A-14B illustrate implementations of a single operator delivery system 700 having an intact microcatheter 600 (FIG. 14A) or a spined microcatheter 600 (FIG. 14B) for delivering a working device 500 having a self-expanding payload 505. The microcatheter 600 in each of these implementations has a step-up in outer diameter from the distal portion 615 to the payload portion 620. As with previous implementations, the procedural guidewire 805 can run the entire length of the delivery system 700 and in the case of FIG. 14A can enter the lumen 605 of the microcatheter 600 at the proximal luer 634 or in the case of FIG. 14B enter the lumen 605 of the microcatheter 600 at a proximal opening 611 into the payload portion 620 of the microcatheter 600 housing the expandable payload 505 in a collapsed configuration. The guidewire 805 can extend through the self-expanding payload 505 housed within the payload portion 620 and exit out the distal opening 610 of the microcatheter. This can allow the coaxial movement of the guidewire 805 through the microcatheter 600 rather than the side-by-side positioning seen in FIGS. 12A-12B. The distal portion 615 of the microcatheter can have a smaller outer diameter such that the payload portion 620 creates a step-up. The step-up of the payload portion 620 can allow for the control element 510 that controls the positioning of the unexpanded payload 505 within the microcatheter 600 to extend inside the lumen 605 of the microcatheter 600 alongside the procedural guidewire 805 for at least a portion or the entirety of the length of the payload portion 620. In the implementation of FIG. 14A, the control element 510 can exit the payload portion 620 at a port 604 located just proximal to the position of the expanding payload 505. In the implementation of FIG. 14B, the control element 510 can exit the payload portion 620 at the proximal opening 611. When a working device such as a stent retriever is released into an embolus, the expanding payload 505 embeds into the embolus and is, in turn, fixed in place. The microcatheter 600 and the guidewire 805 can be withdrawn in sequence or as a unit over the control element 510 with a rapid pull with minimal risk of pulling the expanding payload 505 out of the embolus.

As mentioned above, the guidewire 805 can run through the self-expanding payload 505 within the microcatheter 600 (see for example FIGS. 13A-13B and 14A-14B) providing the operator the sense of a coaxial relationship and providing better wire torque and responsiveness. This coaxial relationship can include a tool or consideration of features to the payload 505 that would avoid catching or ensnaring the guidewire 805 tip as the system 700 is "loaded" with the guidewire 805. The tool may be a simple small tube sized to fit within the garaged payload 505 inside the microcatheter 600 that can be removed once the guidewire 805 passage within the system has been confirmed. A step-up in the catheter diameter may allow for easier loading and may improve guidewire interaction.

FIGS. 12B, 13B, and 14B each illustrate the control element 510 for the working device 500 as having a proximal wire introducer, torquer, or other gripping feature 544 making the proximal control element 510 easy to grasp, advance and/or retract. The gripping feature 544 can be easily identifiable or discernable from other components of the delivery system 700 and/or the distal access system 100 in color and/or shape or other identifier or characteristic. The gripping feature 544 of the control element 510 can be removed prior to withdrawing the delivery system 700 over the control element 510 after deployment of the working device 500. Alternatively, the control element 510 for the working device 500 need not include any proximal gripping features allowing for a more rapid deployment and removal such as shown in FIGS. 12A, 13A, and 14A. Thus, after placement of the distal access system 100 including the guide sheath 400 and the catheter 200 extending through the guide sheath 400 and securing distal access, the operator can fix the distal access point in place with a single hand with a pinch forming a control point where the secured catheter 200 provides support for the smaller catheters and wires that are passed through it. Keeping the distal catheter 200 fixed with a pinch, the guidewire 805 can be advanced through the single operator delivery system 700 having the working device 500, which can be housed pre-loaded within the microcatheter 600. The guidewire 805 extending through the delivery system 700 can be loaded as a unit into the RHV 434 of the guide sheath 400 and advanced toward the end of the distal tip of the catheter 200, the position of the catheter 200 being held fixed by the pinch. Once positioned at a distal tip of the catheter 200, the guidewire 805 can be advanced independently by adjusting the "pinch" to capture the proximal control element 230 of the catheter 200, the proximal control element 510 of the working device 500, and the proximal control element 625 of the microcatheter 600. The systems can all be fixed with a single hand by pinching across their respective proximal control elements gathered together near a proximal end. The guidewire 805 can be advanced across the target while all the control elements are kept fixed. The guidewire 805 can then be held fixed by adding the proximal guidewire 805 to the pinch and adjusting the control element 625 and the control element 510 to be advanced over the guidewire 805. This sort of fixation prevents inadvertent movement of the guidewire tip as the delivery system 700 is advanced to the target, particularly back-and-forth piston movements, avoiding trauma and extravascular bleeding. Each of the single operator systems can be used while applying distal aspiration through the support catheter 200 and the guide sheath 400, for example, as the withdrawal of clot material ensues. In acute ischemic stroke embolectomy procedures, following delivery of the system 700 and withdrawal of the guidewire 805 aspiration is applied at the RHV 434. Fixing the working device 500 in place allows the payload 505 to be unsheathed by pinching the control element 510 and pulling on the microcatheter control element 625. Aspiration can be initiated and then an operator can choose to do a "Solumbra" or "SMAT" procedure. For example, under continuous aspiration, an operator can begin withdrawal of the working device 500 by pulling on the control element 510 while keeping the catheter 200 in a fixed position therein resheathing the payload 505 into the lumen of the catheter 200. The working device 500 can then be removed under continuous aspiration with catheter 200 remaining in place or the working device 500 and the catheter 200 can be removed together as a unit. They can be withdrawn as a unit by pinching both proximal control elements 510 and 230. The single RHV 434 facilitates this by providing a single-point of continuous aspiration.

It should be appreciated that the methods described herein can be performed using a "wire first" approach wherein the guidewire is initially placed across the target once distal access is obtained similar to how coronary procedures may be performed where the guidewire leads and is preserved during the procedure. Once the guidewire is placed across the target, the delivery system 700 having the working device 500 can be prepped with the payload 505 within the proximal portion of the catheter 200 and the guidewire 805 front-loaded onto the distal tip of the microcatheter 600 exiting a port near the distal tip. The guidewire 805 can traverse the payload 505 as well, for example, through an internal channel designed to receive the guidewire 805.

FIGS. 15A-15E illustrate various views of an implementation of a rapid exchange microcatheter for delivering a working device to the neurovasculature for the treatment of stroke. A single inner lumen 605 extends through the distal end region of the microcatheter 600 from the distal opening 610 of the microcatheter 600 to a distal guidewire port 604 and further to a proximal port 606. As such, the procedural guidewire 805 as well as the working device 500 utilize the same inner lumen 605 of the microcatheter 600. The guidewire port 604 can be a side opening from the lumen 605 located a distance proximal to the distal opening 610. The distal guidewire port 604 can be between 5-30 cm from the distal tip of the microcatheter 600. In some implementations, the distal guidewire port 604 is located about 18 cm from the distal tip of the microcatheter 600. The proximal port 606 can be positioned proximal to the distal guidewire port 604 such as for example, about 30 cm to about 45 cm from the distal tip. The distal guidewire port 604 is designed to receive the procedural guidewire 805 to pass through it whereas the proximal port 606 is designed to receive the proximal control element 510 of the working device 500. As such, both the guidewire 805 and the working device 500 extend through the same inner lumen 605 of the microcatheter 600, but utilizing their own ports out from the lumen 605 located in an arrangement that prevents the guidewire 805 and payload 505 of the working device 500 from interfering with one another.

The guidewire 805 can extend through the lumen 605 of the microcatheter 600 from the distal opening 610 to the distal guidewire port 604. The working device 500 (e.g. a cerebral treatment device such as a stent retriever) can be loaded within the lumen 605 of the microcatheter 600, for example by withdrawing the payload 505 proximally pulling it into the lumen 605 through the distal opening 610, such that the payload 505 is garaged at a location just proximal to the side opening or distal guidewire port 604. The expandable payload 505, when loaded in the microcatheter 600, can be housed within the lumen 605 adjacent to the distal guidewire port 604 on a proximal side of the port 604. The procedural guidewire 805 can extend through the same lumen 605 of the microcatheter 600 such that a distal end of the procedural guidewire 805 extends out the distal opening 610 and a proximal end of the procedural guidewire 805 exits the lumen 605 through the distal guidewire port 604 in the wall of the microcatheter 600. The proximal control element 510 of the working device 500 can extend proximally from the payload 505 through the lumen 605 and exit out the proximal port 606. This prevents the proximal control element 510 of the working device 500 and the guidewire 805 from running next to one another within the single lumen 605 or needing to pass through the same entry port, which would be incompatible with rapid exchange systems.

Again with respect to FIGS. 15A-15E, the proximal port 606 can be located near where the proximal control element 625 couples with the intermediate portion of the microcatheter 600. In some implementations, the proximal control element 625 can be a hypotube having a lumen. However, the hypotube lumen truncates to the single lumen 605 at a location near the proximal port 606. Outer shaft tubing 670 can connect the proximal control element 625 and a reinforced portion 652 of the microcatheter as will be described in more detail below. A tapered mandrel extension 675 can bridge and support the outer shaft tubing 670 that connects the proximal control element 625 and the reinforced portion 652 of the microcatheter.

FIGS. 16A-16C are detail views near the distal wire port 604 of different implementations of a rapid exchange microcatheter for delivering a working device to the neurovasculature for the treatment of stroke. The microcatheter 600 includes reinforcement that allows the microcatheter 600 to be advanced independently through the neurovasculature to reach target treatment locations. Without this reinforcement, the microcatheter 600 tubing would be incapable of navigating through such tortuous anatomy. However, the reinforcement required for the microcatheter 600 to navigate the tortuous neuroanatomy presents a challenge for rapid exchange delivery in which ports through the wall of the microcatheter 600 are needed for the guidewire 805 and the control element 510 to exit the lumen 605 as discussed above. To resolve this issue, the microcatheter 600 can have a reinforcement layer formed by two independent reinforcement structures 650, 652 spaced a distance away from one another along the length of the microcatheter 600. A gap G is formed between the reinforcement structures 650, 652 near the location of the distal guidewire port 604. Thus, the microcatheter 600 includes a distal, reinforced catheter portion extending between a distal end region of the catheter body to a point near the side opening 604 and a proximal, reinforced catheter portion extending a distance from a point near the side opening 604 towards the proximal end of the catheter body. The catheter body has a distal opening from the internal lumen near the distal-most tip and a side opening 604 through the sidewall of the catheter body that is located a distance proximal to the distal-most tip of the catheter body. The side opening 604 is positioned within the gap G between the proximal end of the distal reinforced catheter portion and a distal end of the proximal, reinforced catheter portion. The payload of a device housed within the lumen can be positioned proximal to the side opening 604. The proximal, reinforced catheter portion can be less flexible than the distal, reinforced catheter portion. The distal, reinforced catheter portion can have a first reinforcement structure and the proximal, reinforced catheter portion can have a second reinforcement structure. The coupler 660 can formed another reinforcement structure. The first and second reinforcement structures can be similar or different in structure to one another as well as to the coupler 660. The first reinforcement structure can be less rigid than the second reinforcement structure and the second reinforcement structure can be less rigid than the coupler 660.

The size of the gap between the reinforcement structures 650, 652 can vary, but is generally between 3 mm-4 mm wide. The reinforcement structures 650, 652 can be coupled together by a short, relatively rigid coupler 660. The coupler 660 can be sized to span the gap G such that the elongate window of the coupler is aligned with the gap G while at least a first portion of the coupler 660 is positioned over a proximal end of the first reinforcement structure and at least a second portion of the coupler 660 is positioned over the distal end of the second reinforcement structure. The coupler 660 can include a side opening extending through its sidewall, such as an elongate window 654, a slit 655 extending along a length of the coupler 660, or other discontinuity in its sidewall configured to align with the gap between the reinforcement structures 650, 652. The window 654 within the coupler 660 forms the distal wire port 604 located within the gap G between the adjacent reinforcement structures 650, 652 of the microcatheter 600.

Generally, the microcatheter 600 can have an inner liner 656 formed of a flexible material typical of catheters, such as PTFE. The inner liner 656 can be covered by the reinforcement structures 650, 652 and the reinforcement structure 650, 652, in turn, can be encased at least in part by an outer jacket 658 formed of PEBAX or other suitable material (see FIG. 17D). The inner liner 656 and the outer jacket 658 form a dual-laminate membrane encasing the coupler 660, and thus the window 654. The distal wire port 604 is created by forming a slit 662 through the dual-laminate membrane encasing the coupler 660 at a location of the window 654, which will be described in more detail below.

Again with respect to FIGS. 16A-16C, the reinforcement structures 650, 652 can be braided reinforcements, coiled reinforcements, or other reinforcement structure. The structures 650, 652 can be formed of a wire having a particular diameter and formed into a particular pitch or PPI, as is described elsewhere herein. In some implementations, both reinforcement structures 650, 652 are braids having a diameter/PPI that can be the same or different. For example, the distal reinforcement structure 650 can be a braid having 70 PPI and the proximal reinforcement structure 652 can be a braid having 40 PPI. In other implementations, both reinforcement structures 650, 652 are coils having a diameter/pitch that can be the same or different. In still further implementations, a first of the reinforcement structures 650, 652 is a coil and a second of the reinforcement structures 650, 652 is a braid (see FIG. 16B). For example, the distal reinforcement structure 650 can be a coil having a wire diameter of 0.001" and a pitch of 0.010" and the proximal reinforcement structure 652 can be a braid having a braid wire size of 0.0005"×0.0025" and a PPI of 75. In some implementations, at least a first of the reinforcement structures 650, 652 has a wire size of 0.0005"×0.0015" at a PPI of 150 along the entire length of the reinforcement. The wire size, pitch, and PPIs considered herein for the braided or coiled reinforcement structures can vary, but are generally suitable for transmitting sufficient torque typical for neuroaccess microcatheters. The reinforcement structures 650, 652 of the microcatheter 600 can provide a tailored amount of flexibility and torquability to achieve a balance in deliverability and accessibility. The side opening aligned with the gap G between the proximal and distal reinforcement structures 650, 652 allows for the microcatheter 600 to be delivered in a rapid exchange manner as will be described in more detail below.

As mentioned, the reinforcement structures 650, 652 are coupled together by a relatively rigid coupler 660 having a side opening or discontinuity extending through its sidewall, such as an elongate window 654 or slit 655 extending along a length of the coupler that is aligned with the gap G between the reinforcement structures 650, 652. The coupler 660 provides a localized stiff portion that allows for the translation of torque forces from the proximal reinforced end of the microcatheter 600 to the distal reinforced end of the microcatheter 600 while mitigating kinking in this area. The coupler 660 provides stiffness, but not too much stiffness that would also lead to kinking during the navigation of these tortuous regions of the neurovasculature.

The configuration of the coupler 660 can vary. In some implementations, the coupler 660 is a short tube-like structure of relatively rigid material including polymers such as polyimide or PET as well as metallic materials such as stainless steel or the like. The length of the coupler 660 can vary, but is generally between about 3 mm to about 15 mm, preferably between 8 mm-12 mm. In some implementations, the coupler 660 is 7 mm long. The length of the coupler 660 is sufficient to cover at least an end of each of the reinforcement structures 650, 652 while leaving enough length to create the distal wire port 604 via the window 654 or a slit 655 aligned with the gap G. Thus, the coupler 660 can cover at least about 1-2 mm of each reinforcement structures 650, 652 on either end of the coupler 660 and have a region of about 3-4 mm within which the window 654 or slit 655 can be located that aligns with the gap between the reinforcement structures 650, 652 creating the distal wire port 604. The window 654 can have a shape and dimension that varies. In some implementations, the window 654 is about 0.015" wide and is oval in shape. In other implementations, the coupler 660 is a discontinuous tube and has a slit 655 extending along its length from a first end to a second end forming a c-shaped cross-section. The coupler 660 can have only a window 654 (see FIGS. 17A-17D), only a slit 655 (see FIGS. 18A-18C), or both a window 654 and a slit 655 (see FIGS. 19A-19C). The coupler 660 can additionally include one or more cut-outs 657 (e.g. radially) to provide additional flexibility to the region between the reinforcement structures 650, 652 (see FIG. 20). Depending on whether the coupler 660 has a window 654, slit 655, cut-outs 657, or a combination of these features, the dimensions of the material can vary. For example, in some implementations, the coupler 660 is formed of a 7 mm long tube of polyimide having a single slit 655 extending along one side, an inner diameter of about 0.023" and a wall thickness of about 0.001". In another implementation, the coupler 660 is formed of a 7 mm long tube of polyimide having a 3 mm window 654, a slit 655 extending along a backside, an inner diameter of about 0.027" and a wall thickness of about 0.001". The wall thickness of the coupler 660 can be between about 0.005"-about 0.002", preferably around 0.001". The length of the coupler 660 and the wall thickness is selected to ensure the coupler 660 is thick enough to transfer torque from the proximal reinforcement structure 652 to the distal reinforcement structure 650 while mitigating a kink-prone site along the length of the microcatheter 600.

Figure 18A:
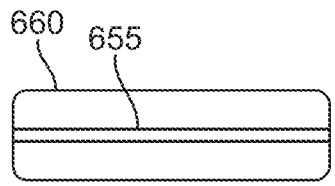
FIGS. 18A-18C illustrate top, side, and cross-sectional views of an implementation of a coupler for the microcatheter of FIG. 16A-16C.
Figure 18B:
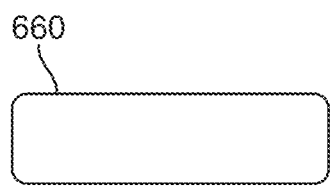
Figure 18C:
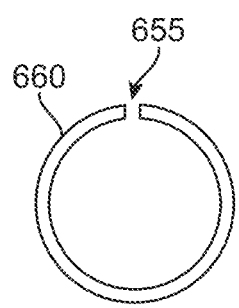
Figure 19C:
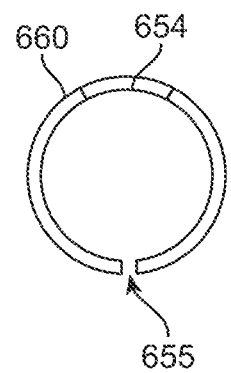

As mentioned above, the coupler 660 can include a slit 655 that extends along its length creating a c-shaped cross-section (see FIGS. 18C and 19C). The c-shaped cross-section of the coupler 660 can provide an additional coupling effect in that it snaps down onto the end portions of each of the reinforcement structures 650, 652 providing additional radial compression or squeezing force down onto the components of the microcatheter 600. The reinforcement structures 650, 652, particularly where they are formed of a braid, can additionally be sealed with a polymer during manufacturing that keeps the ends from unraveling (see FIG. 16C). The polymer dabbed onto their ends aids in the melding together of the components that, in combination with the radial compression provided by the c-shaped coupler 660, provides a better seal with the outer jacket 658.

The outer jacket 658 can be formed of a material as is known in the art such as a PEBAX having a Shore hardness in the range of 25D, 35D, 45D, 55D, 72D depending on what part of the length of the microcatheter 600 the jacket 658 covers. For example, a segment of the outer jacket 658 located proximal to the coupler 660 can be formed of PEBAX having a hardness of about 72D that transitions distally to a segment of the outer jacket 658 formed of PEBAX having a hardness of about 25D. In some implementations, the region of the microcatheter 600 distal to the coupler 660 has an outer jacket 658 formed of PEBAX having a hardness ranging from approximately 25D to 45D, the region of the microcatheter 600 proximal to the coupler 660 has an outer jacket 658 formed of PEBAX having a hardness of about 72D, and the region of the outer jacket 658 covering the coupler 660 (and thus, the window 654) is formed of PEBAX having a hardness of about 55D. In some implementations, the distal most region of the outer jacket 658 is formed of PEBAX having a hardness of about 25D and can be about 5 cm in length. This distal most region can transition proximally to a second region of the outer jacket 658 formed of PEBAX having a hardness of about 35D and can be about 6 cm in length. This second region can transition proximally to a third region of the outer jacket 658 formed of PEBAX having a hardness of about 45D and can be about 5 cm in length. This third region can transition proximally to a fourth region of the outer jacket 658 covering the coupler 660 and the window 654 that is formed of PEBAX having a hardness of about 55D and is about 6 cm in length. This fourth region can transition proximally to additional regions of the outer jacket 658 proximal to the coupler 660 that are formed of PEBAX having a hardness of about 72D.

As mentioned above, the microcatheter 600 can have an inner liner 656 formed of a flexible material that is covered by a reinforcement layer cut into a distal reinforcement structure 650 and a proximal reinforcement structure 652 separated a distance from the distal reinforcement structure 650 forming a gap G. The reinforcement structures 650, 652, in turn, are encased, at least in part, by the outer jacket 658. The reinforcement structures 650, 652 are coupled together by the coupler 660 having a side opening or discontinuity extending through its sidewall, such as the window 654 or the slit 655, that aligns with the gap G between the reinforcement structures 650, 652. The inner liner 656 and the outer jacket 658 encase the coupler 660 and also the side opening (e.g. window 654 and/or slit 655). Thus, at least at the location of the discontinuity in the coupler 660 and the gap G between the reinforcement structures 650, 652, the inner liner 656 and the outer jacket 658 are in contact with one another. Where the inner liner 656 and the outer jacket 658 meet they are fused together forming the dual-laminate membrane at the location of the discontinuity. The distal guidewire port 604 is created by forming a slit 662 through the dual-laminate membrane encasing the discontinuity (e.g. window 654 or slit 655 along a backside of the coupler 660). The slit 662 in the dual-laminate membrane can extend along at least a length of the discontinuity. The distal guidewire port 604 is not merely a hole through which devices enter and exit the lumen 605. Rather, the distal guidewire port 604 is created by the slit 662 in the dual-laminate membrane at the location of the window 654 (or other discontinuity like the slit 655) of the coupler 660. The distal guidewire port 604 forms a flap valve that can remain closed when not in use and that allows for the guidewire 805 to be pushed through it. The presence of the dual-laminate membrane at the distal guidewire port 604 mitigates fluid loss from the lumen 605, for example, during injections and/or aspiration through the lumen of the catheter 600.

The flap valve-like configuration of the distal guidewire port 604 in combination with the coupler 660 also mitigates issues with the working device 500 (e.g. a stent retriever) deployed from the microcatheter lumen 605 getting caught, snagged, or partially exiting the lumen 605 at this location. Some working devices 500 such as stent retrievers having open-ended elements at their distal end region are likely to snag on certain features of the microcatheter delivering the working device, such as these openings, when urged through the lumen 605 of a microcatheter 600. The distal guidewire port 604 is selective for the guidewire 805 to exit the lumen 605 and makes these open-ended elements of the working device 500 being delivered by the microcatheter 600 less likely to get caught during deployment, for example to the level of the ICA to M3 anatomy. The rigidity of the coupler 660 prevents the microcatheter 600 from bending near the location of the side opening 604 making it less likely the working device 500 being delivered through the lumen of the microcatheter 600 would be urged towards the side opening 604. The rigidity of the coupler 660 aided by the dual-laminate membrane encapsulating the coupler 660 mitigate risks of the open-ended devices snagging on or being urged through the guidewire port 604 during distal advancement.

The microcatheter 600 can be packaged having a working device 500 at least partially inserted within the lumen 605. For example, the proximal control element 510 of the working device 500 can extend through the lumen 605 and out the proximal port 606 while the payload 505 of the working device 500 can remain outside the distal opening 610 of the microcatheter 600. Thus, the payload 505 of the working device 500 can remain sticking out the distal end of the microcatheter 600 until the user is ready to "garage" the payload 505 in the lumen 605 of the microcatheter 600 at a location proximal to the distal wire port 604. Once "garaged", the procedural guidewire 805 can freely extend through the lumen 605 and out the distal guidewire port 604 distal to the garaged payload 505. It should be appreciated that the working device 500 need not be pre-inserted in this manner. Additionally, the working device 500 can be back-loaded into position prior to use. The procedural guidewire 805 can be front-loaded or back-loaded prior to use as well.

The lumen 605 of the microcatheter 600 can include additional features to improve the likelihood that only the guidewire 805 exits the distal wire port 604 and working devices 500 garaged in the lumen 605 do not. The payload 505 of the working device 500 can be an expandable element configured to change shape from a compressed configuration into an expanded configuration after deployment from the lumen 605. A deflector or localized thickening can be formed on an inner surface of the lumen 605 just proximal to the distal guidewire port 604 such that a working device 500 being deployed from the lumen 605 such as by advancing in a distal direction through the lumen 605 can be urged into a further compressed configuration as it is pushed past the thickening. This reduces the risk that open-ended components on the distal end of the working device 500 would snag or exit out through the distal guidewire port 604. Another way to prevent open-ended stent-like working devices from snagging or escaping through the window 654 is to reduce the width of the window 654 or discontinuity in the coupler 660 to make the flaps on either side of the discontinuity stiffer. The visibility in and around the region of the distal guidewire port 604 allows the user to easily confirm the location of the payload 505 of the working device 500 relative to the port 604. For example, the working device 500 can be garaged in the microcatheter lumen 605 at a location just proximal to the distal wire port 604. The payload 505 can be withdrawn using the proximal control element 510 thereby pulling the payload 505 into the distal opening 610 of the microcatheter 600. The payload 505 can be further withdrawn through the lumen 605 of the microcatheter 600 until a user visually confirms the payload 505 has been retracted proximal to the distal guidewire port 604. This ensures the payload 505 is clear of the distal guidewire port 604 such that the guidewire 805 can exit/enter the port 604 without interference with the working device 500. In some implementations, the materials in and around the distal guidewire port 604, such as the coupler 660 and the dual-laminate membrane having the slit, can be generally translucent such that a visibility region is formed. In other implementations, the color of the coupler 660 can be selected to provide high contrast between the coupler 660 and its discontinuity. In some implementations, the coupler 660 is black or yellow in color.

In some implementations, the microcatheter 600 can have a translucent region near the gap G. As best shown in FIG. 15E, the coupler 660 can be coupled to just one of the reinforcement structures (in this case, the distal reinforcement structure 650) and to the second reinforcement structure by virtue of a translucent coupler layer 661. The translucent coupler layer 661 can be formed by two layers of PEBAX. The layers 661 in combination with the coupler 660 can compensate for the gap in reinforcement between the reinforcement structures 650, 652 and prevent kinking near the distal wire port 604. At the same time, the coupler layer 661 can provide visualization for a working device loaded in a region of the microcatheter lumen just proximal to the distal wire opening 604. It should be appreciated that where the microcatheter 600 is described as having a coupler spanning the gap G between the reinforcement structures 650, 652 that this can include implementations in which the gap G is spanned by the coupler 660 in combination with the translucent coupler layer 661.

As described herein, the microcatheter 600 can be a rapid exchange microcatheter that is part of a system configured for accessing the intracranial neurovasculature. The microcatheter 600 can include a catheter body having an outer diameter, an inner diameter, and a distal-most tip. The catheter body can include an internal lumen 605 defined by the inner diameter and can be adapted to carry a payload 505 within the internal lumen 605. The payload 505 can be delivered from the internal lumen 605 to a target location in the intracranial neurovasculature. The inner diameter of the internal lumen 605 can be sized to allow passage of a guidewire 805 and the outer diameter can have a maximum size of less than 0.048 inches. The guidewire side opening 604 into the internal lumen 605 is sized to allow passage of the guidewire 805 and can be located a distance between 10 cm to 20 cm from the distal-most tip of the catheter 600. A proximal opening 606 into the internal lumen 605 that is different and distinct from the guidewire side opening 604 can be located a distance greater than 20 cm from the distal-most tip. The microcatheter 600 can include a distal, reinforced catheter portion extending between a distal end region of the catheter body to a point near the guidewire side opening 604 and a proximal, reinforced catheter portion extending a distance from a point near the guidewire side opening 604 towards the proximal end of the catheter body. The guidewire side opening 604 is positioned within a gap between a proximal end of the distal reinforce catheter portion and a distal end of the proximal, reinforced catheter portion. The system can additionally include instructions for use that instruct a user that the payload 505 be loaded in the internal lumen 605 at a location proximal to the guidewire side opening 604 prior to use of the catheter body. The payload 505 loaded in the internal lumen 605 can be at a location proximal to the guidewire side opening 604 such that the payload 505 can be carried within and delivered from the internal lumen 605 to a target location in the intracranial neurovasculature.

Materials

One or more components of the catheters and delivery systems described herein may be made from a metal, metal alloy, polymer, a metal-polymer composite, ceramics, combinations thereof, and the like, or other suitable materials. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

Implementations describe catheters and delivery systems and methods to deliver catheters to target anatomies. However, while some implementations are described with specific regard to delivering catheters to a target vessel of a neurovascular anatomy such as a cerebral vessel, the implementations are not so limited and certain implementations may also be applicable to other uses. For example, the catheters can be adapted for delivery to different neuroanatomies, such as subclavian, vertebral, carotid vessels as well as to the coronary anatomy or peripheral vascular anatomy, to name only a few possible application. It should also be appreciated that although the systems described herein are described as being useful for treating a particular condition or pathology, that the condition or pathology being treated may vary and are not intended to be limiting. Use of the terms "embolus," "embolic," "emboli," "thrombus," "occlusion," etc. that relate to a target for treatment using the devices described herein are not intended to be limiting. The terms may be used interchangeably and can include, but are not limited to a blood clot, air bubble, small fatty deposit, or other object carried within the bloodstream to a distant site or formed at a location in a vessel. The terms may be used interchangeably herein to refer to something that can cause a partial or full occlusion of blood flow through or within the vessel.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of the catheters and/or delivery systems to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A rapid exchange microcatheter system for accessing the intracranial neurovasculature, the microcatheter system comprising:
   (i) a catheter body having:
      (a) an outer diameter, an inner diameter, and a distal-most tip;
      (b) an internal lumen defined by the inner diameter, the catheter body adapted to carry a payload within the internal lumen and deliver the payload from the internal lumen to a target location in the intracranial neurovasculature, wherein (i) the inner diameter is sized to allow passage of a guidewire and (ii) the outer diameter has a maximum size of less than 0.048 inch;
      (c) a guidewire side opening into the internal lumen, the guidewire side opening sized to allow passage of a guidewire, the guidewire side opening located a distance between 10-20 cm from the distal-most tip of the catheter body;
      (d) a proximal opening into the internal lumen, the proximal opening different and distinct from the guidewire side opening, the proximal opening located a distance greater than 20 cm from the distal-most tip;
      (e) a distal, reinforced catheter portion extending between a distal end region of the catheter body to a point near the guidewire side opening; and
      (f) a proximal, reinforced catheter portion extending a distance from a point near the guidewire side opening towards the proximal end of the catheter body;
   wherein the guidewire side opening is positioned within a gap between a proximal end of the distal reinforced catheter portion and a distal end of the proximal, reinforced catheter portion,
   wherein a sidewall of the catheter body comprises:
      a lubricious, tubular liner;
      a reinforcement layer positioned over the tubular liner that is more rigid than the tubular liner, the reinforcement layer comprising:
         a first reinforcement structure extending within the distal, reinforced catheter portion, the first reinforcement structure having a proximal end; and
         a second reinforcement structure extending within the proximal, reinforced catheter portion, the second reinforcement structure having a distal end, wherein the proximal end of the first reinforcement structure is separated from the distal end of the second reinforcement structure creating the gap;
      a short, tubular rigid coupler positioned over the proximal end of the first reinforcement structure and over the distal end of the second reinforcement structure, the coupler having an elongate window extending through a sidewall of the coupler; and
      an outer jacket positioned over the coupler and the reinforcement layer; and
   (ii) instructions for use that instruct that the payload be loaded in the internal lumen at a location proximal to the guidewire side opening prior to use of the catheter body.

2. The rapid exchange microcatheter system of claim 1, wherein the proximal, reinforced catheter portion is less flexible than the distal, reinforced catheter portion.

3. The rapid exchange microcatheter system of claim 1, wherein the distal, reinforced catheter portion has a first reinforcement structure.

4. The rapid exchange microcatheter system of claim 3, wherein the proximal, reinforced catheter portion has a second reinforcement structure.

5. The rapid exchange microcatheter system of claim 4, wherein the first reinforcement structure is coupled to the second reinforcement structure by a rigid coupler.

6. The rapid exchange microcatheter system of claim 4, wherein the first and second reinforcement structure are different in structure to one another.

7. The rapid exchange microcatheter system of claim 4, wherein the first reinforcement structure is a coil and the second reinforcement structure is a coil, wherein a pitch of the coil of the first reinforcement structure is greater than a pitch of the coil of the second reinforcement structure.

8. The rapid exchange microcatheter system of claim 5, wherein the coupler has a window aligned with the side opening.

9. A rapid exchange microcatheter system for accessing the intracranial neurovasculature, the microcatheter system comprising:
   (i) a catheter body having:
      (a) an outer diameter, an inner diameter, and a distal-most tip;
      (b) an internal lumen defined by the inner diameter, the catheter body adapted to carry a payload within the internal lumen and deliver the payload from the internal lumen to a target location in the intracranial neurovasculature, wherein (i) the inner diameter is sized to allow passage of a guidewire and (ii) the outer diameter body has a maximum size of less than 0.048 inch;
      (c) a guidewire side opening into the internal lumen, the guidewire side opening sized to allow passage of a guidewire, the guidewire side opening located a distance between 10-20 cm from the distal-most tip of the catheter body;
      (d) a proximal opening into the internal lumen, the proximal opening different and distinct from the guidewire side opening, the proximal opening located a distance greater than 20 cm from the distal-most tip;
      (e) a distal, reinforced catheter portion extending between a distal end region of the catheter body to a point near the guidewire side opening; and
      (f) a proximal, reinforced catheter portion extending a distance from a point near the guidewire side opening towards the proximal end of the catheter body;
   wherein the guidewire side opening is positioned within a gap between a proximal end of the distal reinforced catheter portion and a distal end of the proximal, reinforced catheter portion,
   wherein a sidewall of the catheter body comprises:
      a lubricious, tubular liner;
      a reinforcement layer positioned over the tubular liner that is more rigid than the tubular liner, the reinforcement layer comprising:
         a first reinforcement structure extending within the distal, reinforced catheter portion, the first reinforcement structure having a proximal end; and
         a second reinforcement structure extending within the proximal, reinforced catheter portion, the second reinforcement structure having a distal end, wherein the proximal end of the first reinforcement structure is separated from the distal end of the second reinforcement structure creating the gap;

a short, tubular rigid coupler positioned over the proximal end of the first reinforcement structure and over the distal end of the second reinforcement structure, the coupler having an elongate window extending through a sidewall of the coupler; and an outer jacket positioned over the coupler and the reinforcement layer; and (ii) the payload loaded in the internal lumen at a location proximal to the guidewire side opening such that the payload can be carried within and delivered from the internal lumen to a target location in the intracranial neurovasculature.

10. The rapid exchange microcatheter system of claim 9, wherein the proximal, reinforced catheter portion is less flexible than the distal, reinforced catheter portion.

11. The rapid exchange microcatheter system of claim 9, wherein the distal, reinforced catheter portion has a first reinforcement structure.

12. The rapid exchange microcatheter system of claim 11, wherein the proximal, reinforced catheter portion has a second reinforcement structure.

13. The rapid exchange microcatheter system of claim 12, wherein the first reinforcement structure is coupled to the second reinforcement structure by a rigid coupler.

14. The rapid exchange microcatheter system of claim 12, wherein the first and second reinforcement structure are different in structure to one another.

15. The rapid exchange microcatheter system of claim 12, wherein the first reinforcement structure is a coil and the second reinforcement structure is a coil, wherein a pitch of the coil of the first reinforcement structure is greater than a pitch of the coil of the second reinforcement structure.

16. The rapid exchange microcatheter system of claim 13, wherein the coupler has a window aligned with the side opening.

* * * * *